US012269822B2

(12) United States Patent
Long et al.

(10) Patent No.: US 12,269,822 B2
(45) Date of Patent: Apr. 8, 2025

(54) ANTHELMINTHIC HETEROCYCLIC COMPOUNDS

(71) Applicants: BOEHRINGER INGELHEIM ANIMAL HEALTH USA INC., Duluth, GA (US); BOEHRINGER INGELHEIM PHARMA GMBH & CO. KG, Ingelheim am Rhein (DE)

(72) Inventors: Alan Long, Flowery Branch, GA (US); Hyoung Lee, Alpharetta, GA (US); Hannes Fiepko Koolman, Biberach an der Riss (DE)

( * ) Notice: Subject to any disclaimer, the term of this patent is extended or adjusted under 35 U.S.C. 154(b) by 850 days.

(21) Appl. No.: 17/142,877

(22) PCT Filed: Jul. 3, 2019

(86) PCT No.: PCT/US2019/040509
§ 371 (c)(1),
(2) Date: Jan. 6, 2021

(87) PCT Pub. No.: WO2020/014068
PCT Pub. Date: Jan. 16, 2020

(65) Prior Publication Data
US 2022/0048903 A1    Feb. 17, 2022

Related U.S. Application Data

(60) Provisional application No. 62/695,656, filed on Jul. 9, 2018.

(51) Int. Cl.
*C07D 471/04* (2006.01)
*A61P 33/10* (2006.01)

(52) U.S. Cl.
CPC ............ *C07D 471/04* (2013.01); *A61P 33/10* (2018.01)

(58) Field of Classification Search
CPC ...... C07D 471/04; A61P 33/10; A61K 31/437
See application file for complete search history.

(56) References Cited

U.S. PATENT DOCUMENTS

| | | |
|---|---|---|
| 4,464,372 A | 8/1984 | Bristol et al. |
| 5,434,150 A | 7/1995 | Austel et al. |
| 6,900,208 B2 | 5/2005 | Salvati et al. |
| 6,911,543 B2 | 6/2005 | Walker et al. |
| 7,030,112 B2 | 4/2006 | Salvati et al. |
| 7,153,854 B2 | 12/2006 | Abe et al. |
| 7,300,932 B2 | 11/2007 | Fox et al. |
| 7,306,631 B2 | 12/2007 | Glenn, Jr. et al. |
| 7,420,056 B2 | 9/2008 | Kuehnert et al. |
| 7,456,192 B2 | 11/2008 | Imbert et al. |
| 7,476,685 B2 | 1/2009 | Araki et al. |
| 7,723,336 B2 | 5/2010 | Vaccaro et al. |
| 7,893,085 B2 | 2/2011 | Savy et al. |
| 7,919,628 B2 | 4/2011 | Hachtel et al. |
| 7,956,068 B2 | 6/2011 | Carson et al. |
| 7,964,204 B2 | 6/2011 | Lahm et al. |
| 8,030,327 B2 | 10/2011 | Sato et al. |
| 8,252,795 B2 | 8/2012 | Fink et al. |
| 8,431,593 B2 | 4/2013 | Hutchison et al. |
| 8,450,354 B2 | 5/2013 | Mjalli et al. |
| 8,772,301 B2 | 7/2014 | Hardy et al. |
| 9,023,850 B2 | 5/2015 | Lahm et al. |
| 9,556,169 B2 | 1/2017 | Chatterjee et al. |
| 9,718,816 B2 | 8/2017 | Chesworth et al. |
| 9,802,961 B2 | 10/2017 | Clark et al. |
| 9,868,749 B2 | 1/2018 | Alexander et al. |
| 9,873,703 B2 | 1/2018 | Ali et al. |
| 10,138,248 B2 | 11/2018 | Buesking et al. |
| 2004/0242587 A1 | 12/2004 | Fu |
| 2006/0074102 A1 | 4/2006 | Cusack et al. |
| 2007/0027093 A1 | 2/2007 | Ogawa et al. |
| 2007/0275962 A1 | 11/2007 | Koul et al. |
| 2011/0105457 A1 | 5/2011 | Taniyama et al. |
| 2011/0195933 A1 † | 8/2011 | Katz |
| 2011/0206607 A1 | 8/2011 | Olsson et al. |
| 2011/0245274 A1 | 10/2011 | Nanchen et al. |
| 2012/0065200 A1 | 3/2012 | Barbosa et al. |
| 2012/0083476 A1 | 4/2012 | Breitenbucher et al. |
| 2012/0219500 A1 | 8/2012 | Sakurai et al. |
| 2013/0071415 A1 | 3/2013 | Babu et al. |
| 2013/0203692 A1 | 8/2013 | Soll et al. |
| 2014/0045826 A1 | 2/2014 | Shakespeare et al. |
| 2014/0066434 A1 | 3/2014 | Shakespeare |

(Continued)

FOREIGN PATENT DOCUMENTS

| | | |
|---|---|---|
| CA | 3117343 A1 | 4/2020 |
| CL | 202100033 | 7/2021 |

(Continued)

OTHER PUBLICATIONS

Meanwell, N. A. Synopsis of Some Recent Tactical Application of Bioisosteres in Drug Design. Journal of Medicinal Chemistry, 54(8), 2529-2591. https://doi.org/10.1021/jm1013693 (Year: 2011).*

Database Registry [Online], May 1, 2020 (May 1, 2020), Life Chemicals Inc.: "Imidazo[I,2-b]pyridazine-6-carboxamide, N-(1,2,3,4-tetrahydro-1-naphthalenyl)-", XP055837558, Database accession No. 2415490-08-1 compound with the Registry No. 2415490-08-1.

Database Registry (Online) Chemical Abstracts Service, Columbus, Ohio, US; Jul. 17, 2016, XP002799055, Database accession No. 1953874-77-5, 2-Benzofurancarboxamide,3,4,7-trimethyl-N-(octahydro-4-benzofuranyl)-.

Database Registry (Online) Chemical Abstracts Service, Columbus, Ohio, US; Oct. 15, 2017, XP002799056, Database accession No. 2134947-60-5, 2-Benzofurancarboxamide,3,4,7-trimethyl-N-(4,5,6,7-tetrahydro-1-methyl-1H-indazol-4-yl)-.

(Continued)

*Primary Examiner* — Yih-Horng Shiao
*Assistant Examiner* — Hoi Yan Nmn Lee

(57) ABSTRACT

A compound of formula (I), (IA) or formula (II) or a composition comprising the compound of formula (I), (IA) or formula (II) in association with a veterinarily acceptable carrier are described. A method of controlling helminths using same is described.

17 Claims, No Drawings

(56) References Cited

U.S. PATENT DOCUMENTS

| | | |
|---|---|---|
| 2015/0126523 A1 | 5/2015 | Meng |
| 2016/0106102 A1 | 4/2016 | Kuebbeler et al. |
| 2016/0333012 A1 | 11/2016 | Chatterjee et al. |
| 2017/0369486 A1 | 12/2017 | Acharya et al. |
| 2018/0230157 A1 | 8/2018 | Bacon et al. |
| 2019/0071447 A1 | 3/2019 | Kohler et al. |
| 2019/0233425 A1 | 8/2019 | Bayly et al. |
| 2019/0352275 A1 | 11/2019 | Meldrum et al. |
| 2020/0024264 A1 | 1/2020 | Hubsch et al. |
| 2020/0237771 A1 | 7/2020 | Hallur et al. |
| 2022/0047569 A1 | 2/2022 | Kazmi et al. |

FOREIGN PATENT DOCUMENTS

| | | | |
|---|---|---|---|
| CL | 202201662 | | 2/2023 |
| CL | 202201739 | | 3/2023 |
| CL | 202202346 | A | 4/2023 |
| EP | 1277754 | B1 | 7/2005 |
| EP | 3078664 | A1 | 10/2016 |
| EP | 3643711 | A1 | 4/2020 |
| JP | 2009203214 | A | 9/2009 |
| JP | 2011140452 | A | 7/2011 |
| JP | 2012012299 | A | 1/2012 |
| JP | 2016505529 | A | 2/2016 |
| RU | 2004136978 | A | 6/2005 |
| WO | 2000053602 | A1 | 9/2000 |
| WO | 2005066177 | A1 | 7/2005 |
| WO | 2006004191 | A1 | 1/2006 |
| WO | 2007123855 | A2 | 11/2007 |
| WO | 2008019309 | A1 | 2/2008 |
| WO | 2010017046 | A1 | 2/2010 |
| WO | 2011058109 | A1 | 5/2011 |
| WO | 2011075591 | A1 | 6/2011 |
| WO | 2011137587 | A1 | 11/2011 |
| WO | 2011146401 | A1 | 11/2011 |
| WO | 2012100342 | A1 | 8/2012 |
| WO | 2012107533 | A1 | 8/2012 |
| WO | 2014078802 | A1 | 5/2014 |
| WO | 2015066277 | A1 | 5/2015 |
| WO | 2017093180 | A1 | 6/2017 |
| WO | WO-2017125898 | A1 * | 7/2017 ........... A61K 31/437 |
| WO | 2017/178416 | A1 | 10/2017 |
| WO | 2018/087036 | A1 | 5/2018 |
| WO | 2018/197401 | A1 | 11/2018 |
| WO | 2019/002132 | A1 | 1/2019 |
| WO | 2019/025341 | A1 | 2/2019 |
| WO | 2019/115768 | A1 | 6/2019 |
| WO | 2019/215182 | A1 | 11/2019 |
| WO | 2020002124 | A1 | 1/2020 |
| WO | 2020012336 | A1 | 1/2020 |
| WO | 2020014068 | A1 | 1/2020 |
| WO | 2020083971 | A2 | 4/2020 |
| WO | 2020131629 | A1 | 6/2020 |
| WO | 2020131631 | A1 | 6/2020 |
| WO | 2020191091 | A1 | 9/2020 |
| WO | 2020219871 | A1 | 10/2020 |
| WO | 2020247747 | A1 | 12/2020 |
| WO | 2021018839 | A1 | 2/2021 |
| WO | 2021030379 | A1 | 2/2021 |
| WO | 2021032934 | A1 | 2/2021 |
| WO | 2021/127443 A1 | | 6/2021 |
| WO | 2021122906 | A1 | 6/2021 |
| WO | 2021122911 | A1 | 6/2021 |
| WO | 2021/130731 | A1 | 7/2021 |
| WO | 2021173713 | A1 | 9/2021 |
| WO | 2021204930 | A1 | 10/2021 |
| WO | 2021231571 | A1 | 11/2021 |
| WO | 2021242581 | A1 | 12/2021 |
| WO | 2022106469 | A2 | 5/2022 |
| WO | 2022117783 | A1 | 6/2022 |
| WO | 2022122987 | A1 | 6/2022 |
| WO | 2022122988 | A1 | 6/2022 |
| WO | 2022152918 | A1 | 7/2022 |

OTHER PUBLICATIONS

Database Registry (Online) Chemical Abstracts Service, Columbus, Ohio, US; Aug. 15, 2011, XP002799057, Database accession No. 1318005-39-8, 2-Benzofurancarboxamide, N-(6-bromo-3,4-dihydro-2H-1-benzopyran-4-yl)-3,7-dimethyl-.

Database Registry (Online) Chemical Abstracts Service, Columbus, Ohio, US; Dec. 23, 2015, XP002799058, Database accession No. 1835595-46-4, 2-Benzofurancarboxamide, N-(6-amino-1,2,3,4-tetrahydro-1-naphthalenyl)-3,4,7-trimethyl-, hydrochloride (1:1).

Database Registry (Online) Chemical Abstracts Service, Columbus, Ohio, US; Nov. 18, 2018, XP002799059, Database accession No. 2249355-47-1, 2-Benzofurancarboxamide, N-(6,7-dihydro-5H-pyrrolo[1,2-a]imidazol-7-yl)-3,7-dimethyl-.

Database Registry (Online) Chemical Abstracts Service, Columbus, Ohio, US; Jul. 4, 2016, XP002799060, Database accession No. 1944784-28-4, 2-Benzofurancarboxamide, 5-bromo-7-methyl-N-(4,5,6,7-tetrahydro-2-methyl-2H-indazol-4-yl)-.

Preston, "Low cost whole-organism screening of compounds for anthelmintic activity", International Journal for Parasitology, vol. 45, pp. 333-343.

Database Registry (Online) Chemical Abstracts Service, Columbus, Ohio, US; Nov. 15, 2018, Database accession No. 2248503-07-1, 2-Benzofurancarboxamide, 7-methyl-N-[(8R)-5,6,7,8-tetrahydro-8-quinolinyl]- (CA Index Name).

Database Registry (Online) Chemical Abstracts Service, Columbus, Ohio, US; Dec. 23, 2015, Database accession No. 1835595-45-3, 2-Benzofurancarboxamide, N-(6-amino-1,2,3,4-tetrahydro-1-naphthalenyl)-3,4,7-trimethyl- (CA Index Name).

Database Registry (Online) Chemical Abstracts Service, Columbus, Ohio, US; Dec. 23, 2015, Database accession No. 1835526-11-8, 2-Benzofurancarboxamide, N-(6-amino-1,2,3,4-tetrahydro-1-naphthalenyl)-3,7-dimethyl-, hydrochloride (1:1) (CA Index Name).

Database Registry (Online) Chemical Abstracts Service, Columbus, Ohio, US; Dec. 23, 2015, Database accession No. 1835526-10-7, 2-Benzofurancarboxamide, N-(6-amino-1,2,3,4-tetrahydro-1-naphthalenyl)-3,7-dimethyl- (CA Index Name).

Database Registry (Online) Chemical Abstracts Service, Columbus, Ohio, US; Feb. 7, 2012, Database accession No. 1355505-50-8, 2-Benzofurancarboxamide, N-(1,2,5,6,7,8-hexahydro-2-oxo-5-quinolinyl)-3,7-dimethyl- (CA Index Name).

Database Registry (Online) Chemical Abstracts Service, Columbus, Ohio, US; May 24, 2011, Database accession No. 1299845-91-2, 2-Benzofurancarboxamide, N-[1-(1, 1-dimethylethyl)-4,5,6,7-tetrahydro-1H-indazol-4-yl]-3,7-dimethyl- (CA Index Name).

Koyanagi, T. & Haga, T. Bioisosterism in Agrochemicals. 15-24 (1995).

INPADOC Patent Family for WO 2021/173713 A1 accessed from https://worldwide.espacenet.com/patent/search/family/077491553/publication/WO2021173713A1?q=WO2021173713 on Sep. 20, 2024.

\* cited by examiner

† cited by third party

ANTHELMINTHIC HETEROCYCLIC COMPOUNDS

CROSS REFERENCE TO RELATED APPLICATIONS

This application is a divisional of U.S. patent application Ser. No. 17/142,877, filed Jan. 6, 2021, which is a national stage entry of PCT/US2019/040509 filed on Jul. 3, 2019, which claims the benefit of U.S. Provisional Patent Application No. 62/695,656, filed Jul. 9, 2018, both of which are incorporated herein by reference in their entirety, and relied upon for any purpose.

This patent application relates to new anthelmintic compounds, compositions comprising the compounds, and methods of using the compounds to control helminths.

FIELD

The present application is directed to new anthelmintic heterocyclic compounds with improved activity against endoparasites and/or ectoparasites. The application is also directed to compositions comprising the compounds, methods and uses of the compounds for eradicating, controlling, and preventing a parasite infestation and/or infection in animals. The compounds may be administered to animals, particularly mammals, fish and birds, to prevent or treat parasitic infections.

BACKGROUND

Animals, such as mammals and birds, are often susceptible to parasite infestations. These parasites may be ectoparasites, such as fleas and ticks. Animals and humans also suffer from endoparasitic infections including, for example, helminthiasis which is most frequently caused by a group of parasitic worms described as nematodes or roundworms. These parasites cause severe economic losses in pigs, sheep, horses, and cattle as well as affecting companion animals (e.g. cats and dogs) and poultry. Other parasites include those which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides* and *Trichinella*.

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period". L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet.* Parasitol. 2005 Oct. 24 133(2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al., (*Vet. Parasitol.* 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. Heartworm Preventive Resistance. Is it Possible, vol. 37. Bulletin of the American Heartworm Society, pp. 5.). Thus, there is an ongoing need to develop new anthelmintic agents with improved activity against *Dirofilaria immitis* and other endoparasites.

It is expressly noted that citation or identification of any document in this application is not an admission that such document is available as prior art to the present description. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the description.

SUMMARY

In one embodiment, the invention provides a compound, e.g., of formula (I):

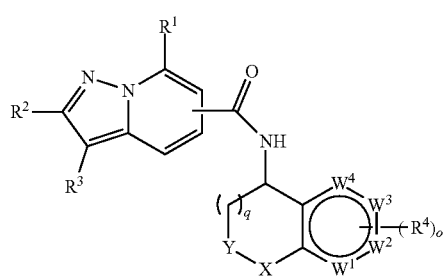

(I)

wherein:
$W^1$, $W^2$, $W^3$ and $W^4$ are independently C—H or N;
$R^1$ is hydrogen, cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted haloalkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$SO_n$, amino, NH-optionally substituted alkyl, or $NR^aR^b$ wherein $R^a$ and $R^b$ are independently optionally substituted $C_1$-$C_4$ alkyl; or $R^a$ and $R^b$ may form, with the nitrogen to which they are attached, a 3, 4, 5, 6, 7, or 8 membered-heterocyclyl group, which may be optionally substituted;
$R^2$ is hydrogen, halogen, cyano, optionally substituted alkoxy, optionally substituted aryloxy, optionally substituted alkyl, optionally substituted $C_3$-$C_8$-cycloalkyl, or $SO_m$(optionally substituted alkyl);
$R^3$ is selected from the group consisting of 6- or 10-membered aryl and 5- to 10-membered heteroaryl, each of which may be optionally substituted with 1, 2, 3, 4 or 5 substituents;
Each $R^4$ is independently hydrogen, halogen, cyano, nitro, —OH, optionally substituted alkyl, optionally substituted alkoxy, optionally substituted cycloalkyl, -amino, NH-optionally substituted alkyl, $SF_5$, or $NR^cR^d$ wherein $R^c$ and $R^d$ are independently optionally substituted alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted $C_1$-$C_4$-alkyl);
o is 0, 1, 2, 3, or 4;
m, n, and p are independently 0, 1, or 2;
q is 0 or 1;
X and Y are independently $CR^5R^6$, O, S, or N—$R^7$, wherein at least one of X and Y is $CR^5R^6$;
$R^5$ and $R^6$ are independently hydrogen, fluorine or $C_1$-$C_4$-alkyl;
$R^7$ is hydrogen or $C_1$-$C_4$-alkyl; or
a stereoisomer, tautomer, N-oxide, hydrate, solvate, or salt thereof.

In another embodiment, the invention provides a compound of formula (IA) shown below, wherein the definition of variables $R^1$, $R^2$, $R^3$, $R^4$, X, Y, q and o is the same as for formula (I) and $W^5$, $W^6$ and $W^7$ are independently CH, N or S.

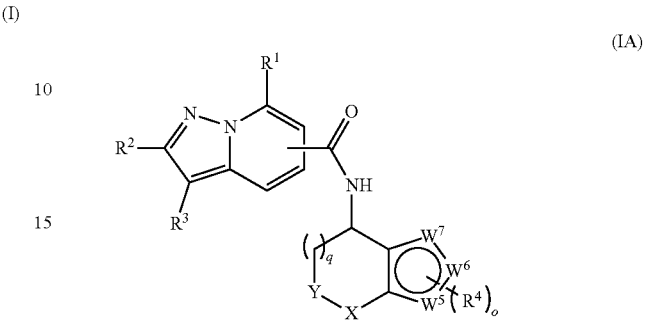

(IA)

The description includes a compound, e.g., a compound of formula (I-1):

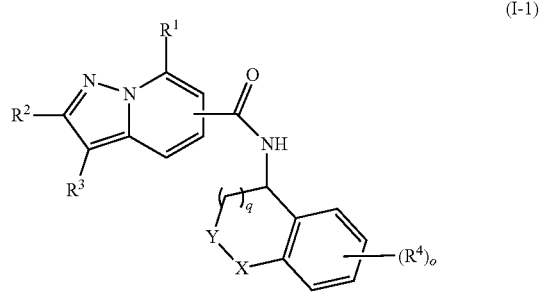

(I-1)

wherein:
$R^1$ is hydrogen, cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted haloalkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$SO_n$, amino, NH-optionally substituted alkyl, or $NR^aR^b$ wherein $R^a$ and $R^b$ are independently optionally substituted $C_1$-$C_4$ alkyl; or $R^a$ and $R^b$ may form, with the nitrogen to which they are attached, a 3, 4, 5, 6, 7, or 8 membered-heterocyclyl group, which may be optionally substituted;
$R^2$ is hydrogen, halogen, cyano, optionally substituted alkoxy, optionally substituted aryloxy, optionally substituted alkyl, optionally substituted $C_3$-$C_8$-cycloalkyl, or $SO_m$(optionally substituted alkyl);
$R^3$ is selected from the group consisting of 6- or 10-membered aryl and 5- to 10-membered heteroaryl, each of which may be optionally substituted with 1, 2, 3, 4 or 5 substituents;
Each $R^4$ is independently hydrogen, halogen, cyano, nitro, —OH, optionally substituted alkyl, optionally substituted alkoxy, optionally substituted cycloalkyl, -amino, NH-optionally substituted alkyl, SF$_5$, or NR$^c$R$^d$ wherein R$^c$ and R$^d$ are independently optionally substituted alkyl; or R$^c$ and R$^d$ may form, with the nitrogen to which they are attached, a 3, 4, 5, 6, 7, or 8 membered-heterocyclyl group, which may be optionally substituted, SO$_p$(optionally substituted C$_1$-C$_4$-alkyl);

o is 0, 1, 2, 3, or 4;

m, n, and p are independently 0, 1, or 2;

q is 0 or 1;

X and Y are independently CR$^5$R$^6$, O, S, or N—R$^7$, wherein at least one of X and Y is CR$^5$R$^6$;

R$^5$ and R$^6$ are independently hydrogen, fluorine or C$_1$-C$_4$-alkyl;

R$^7$ is hydrogen or C$_1$-C$_4$-alkyl; or a stereoisomer, tautomer, N-oxide, hydrate, solvate, or salt thereof.

The description also includes a veterinarily acceptable composition comprising the compound and a veterinarily acceptable carrier and a method of controlling helminths comprising administering the compound, or the veterinarily acceptable composition thereof, to an animal in need thereof. The application is also and uses of the compound for eradicating, controlling, and preventing a parasite infestation and/or infection in animals. The compound may be administered to animals, particularly mammals, fish and birds, to prevent or treat parasitic infections.

The compound and compositions comprising the compound are highly effective for the treatment and prophylaxis of internal parasites in mammals, fish and birds, and in particular, cats, dogs, horses, chickens, pigs, sheep and cattle, with the aim of substantially ridding these hosts of endoparasites.

In an embodiment, the compound and compositions are substantially effective against endoparasites, such as filariae (e.g. heartworm), hookworms, whipworms and roundworms of the digestive tract of animals and humans. In certain embodiments, the compound and compositions of the description are effective against *Dirofilaria immitis* (heartworm) isolates that are less sensitive to treatment with macrocyclic lactones. In another embodiment, compound and compositions are effective for treating and preventing infections of animals with nematodes that are less sensitive to treatment with commercially available or known active agents.

In an embodiment, the description includes a combination of the compound with at least a second active agent, which may broaden the scope of protection afforded to animals against endoparasites and/or ectoparasites.

The description may include a method for the treatment and prevention of a parasitic infection or infestation in an animal comprising administering a compound, e.g., a compound of formula (I), to the animal. The description includes a use of the compound, e.g., the compound of formula (I) for the treatment and/or prevention of a parasitic infections and infestations in animals and the use of the compounds in the preparation of a medicament for the treatment and/or prevention of a parasitic infection in an animal.

Thus, the description includes at least the following features:

(a) In one embodiment, a compound, e.g., a compound of formula (I) or (IA), etc., or a pharmaceutically or a veterinarily acceptable salt thereof, which is an active endoparasiticide and in some cases also active against ectoparasites;

(b) a veterinary composition comprising a parasiticidally effective amount of the compound, e.g., a compound of formula (I) or (IA), etc., or a pharmaceutically or veterinarily acceptable salt thereof, in combination with a pharmaceutically or veterinarily acceptable carrier or diluent;

(c) a veterinary composition comprising a parasiticidally effective amount of the compound, e.g., a compound of formula (I) or (IA), etc., or a pharmaceutically or veterinarily acceptable salt thereof, in combination with one or more other active agents and a pharmaceutically or veterinarily acceptable carrier or diluent;

(d) a method for treating a parasitic infestation/infection in or on an animal comprising administering a parasiticidally effective amount of the compound e.g., a compound of formula (I) or (IA), etc., or a pharmaceutically or veterinarily acceptable salt thereof, optionally with one or more additional active agents, to the animal in need thereof;

(e) a method for the prevention of a parasitic infestation/infection of an animal, which comprises administering a parasiticidally effective amount of a compound, e.g., a compound of formula (I) or (IA), etc., or a pharmaceutically or a veterinarily acceptable salt thereof, optionally with one or more additional active agents, to the animal in need thereof;

(f) a use of the compound, e.g., a compound of formula (I) or (IA), etc., or a pharmaceutically or a veterinarily acceptable salt thereof, for the treatment or prevention of a parasitic infection and possibly also a parasitic infestation in an animal;

(g) a use of the compound, e.g., the compound of formula (I) or (IA), etc., or a pharmaceutically or veterinarily acceptable salt thereof, for the manufacture of a veterinary medicament for the treatment or prevention of a parasitic infection in an animal; and (h) a process for the preparation of the compound, e.g., the compound of formula (I) or (IA), etc.

DEFINITIONS

Terms used herein will have their customary meanings in the art unless otherwise specified. The organic moieties mentioned in the definitions of the variables of the compounds e.g, the compound of formula (I) are like the term halogen—i.e., collective terms for individual listings of the individual group members—fluoro, chloro, bromo and iodo with respect to halogen. The prefix C$_n$-C$_m$ indicates in each case the possible number of carbon atoms in the group from an integer n to another integer m.

In the present specification and claims the term "including but not limited to" is equivalent to "included".

By the term "optionally substituted" is meant a radical that is optionally substituted by one or more of the following moieties: halogen, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, aryl, and heteroaryl, or any other viable functional group that does not inhibit the biological activity of the compounds of the description, either unprotected, or protected as necessary, as known to those skilled in the art, for example, as taught in Greene and Wuts, Protective Groups in Organic Synthesis, John Wiley and Sons, Third Edition, 1999, hereby incorporated by reference.

Unless otherwise stated, "alkyl" means, either alone or in combination with a heteroatom, e.g., alkoxy, thioalkyl, alkylamino, and the like, saturated straight, branched, primary, secondary or tertiary hydrocarbons, including those having 1 to 12 atoms. In some embodiments, alkyl groups will include $C_1$-$C_{10}$, $C_1$-$C_8$, $C_1$-$C_6$, $C_1$-$C_4$ or $C_1$-$C_3$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

Carbocyclic groups are cyclic groups composed exclusively of carbon. The carbocyclic groups include both aromatic rings such as phenyl and non-aromatic rings such cyclohexyl and include those with 3 to 14 carbon atoms having single or multiple fused rings.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$, $C_2$-$C_4$, or $C_3$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples of alkenyl or a specific range thereof include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example C1-C4-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

The term "alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, —$SF_5$, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above. The term "heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Examples of heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl, or pyrrolopyrimidyl. Heteroaryl rings may be unsubstituted or substituted by one or more moieties as described for aryl above.

The term "heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

The term "alkylthio" refers to alkyl-S—, where "alkyl" is as defined above. In some embodiments, the alkyl component of the alkylthio group will include $C_1$-$C_{10}$, $C_1$-$C_8$, $C_1$-$C_6$ $C_1$-$C_4$ or $C_1$-$C_3$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$, $C_1$-$C_4$ or $C_1$-$C_3$ alkyl groups. Examples include, but are not limited to, —SO—$CH_3$, —SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylsulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above.

The term "alkylsulfonyl" refers to the group alkyl-S(=O)$_2$ —, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —$SO_2$—$CH_3$, —$SO_2$—$C_2H_5$, n-propylsulfonyl, —$SO_2$—$CH(CH_3)_2$, n-butylsulfonyl, 1-methylpropylsulfonyl, 2-methylpropylsulfonyl, —$SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2- dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The terms "alkenylfulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$ —, and haloalkyl-S(=O)$_2$—, haloalkenyl-S(=O)$_2$—, and haloalkynyl-S(=O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

The term "compound", unless otherwise specified, means a compound of formula (I) or compound of formula (II), or another compound that may be an anthelminthic heterocyclic compound.

DETAILED DESCRIPTION

In an embodiment, the description includes a compound of formula (I):

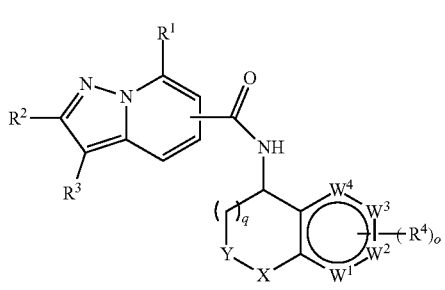

(I)

$W^1$ $W^2$, $W^3$ and $W^4$ are independently C—H or N;

$R^1$ is hydrogen, cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted haloalkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-SO$_n$, haloalkyl-SO$_n$, amino, NH-optionally substituted alkyl, or NR$^a$R$^b$ wherein R$^a$ and R$^b$ are independently optionally substituted $C_1$-$C_4$ alkyl; or R$^a$ and R$^b$ may form, with the nitrogen to which they are attached, a 3, 4, 5, 6, 7, or 8 membered-heterocyclyl group, which may be optionally substituted;

$R^2$ is hydrogen, halogen, cyano, optionally substituted alkoxy, optionally substituted aryloxy, optionally substituted alkyl, optionally substituted $C_3$-$C_8$-cycloalkyl, or SO$_m$(optionally substituted alkyl);

$R^3$ is selected from the group consisting of 6- or 10-membered aryl and 5- to 10-membered heteroaryl, each of which may be optionally substituted with 1, 2, 3, 4 or 5 substituents;

Each $R^4$ is independently hydrogen, halogen, cyano, nitro, —OH, optionally substituted alkyl, optionally substituted alkoxy, optionally substituted cycloalkyl, -amino, NH-optionally substituted alkyl, SF$_5$, or NR$^c$R$^d$ wherein R$^c$ and R$^d$ are independently optionally substituted alkyl; or R$^c$ and R$^d$ may form, with the nitrogen to which they are attached, a 3, 4, 5, 6, 7, or 8 membered-heterocyclyl group, which may be optionally substituted, SO$_p$(optionally substituted $C_1$-$C_4$-alkyl);

o is 0, 1, 2, 3, or 4;

m, n, and p are independently 0, 1, or 2;

q is 0 or 1;

X and Y are independently CR$^5$R$^6$, O, S, or N—R$^7$, wherein at least one of X and Y is CR$^5$R$^6$;

$R^5$ and $R^6$ are independently hydrogen, fluorine or $C_1$-$C_4$-alkyl;

$R^7$ is hydrogen or $C_1$-$C_4$-alkyl; or a stereoisomer, tautomer, N-oxide, hydrate, solvate, or salt thereof.

In another embodiment, the description includes a compound of formula (IA) shown below, wherein the definition of variables $R^1$, $R^2$, $R^3$, $R^4$, X, Y, q and o is the same as for formula (I) and $W^5$, $W^6$ and $W^7$ are independently CH, N or S.

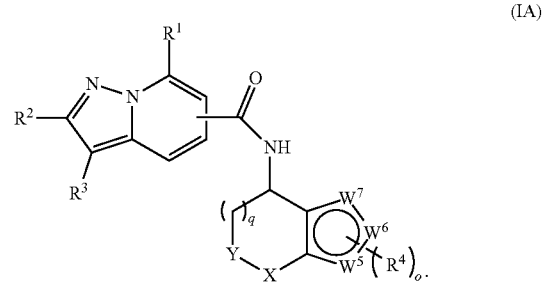

(IA)

In an embodiment, the description includes a compound of formula (I-1):

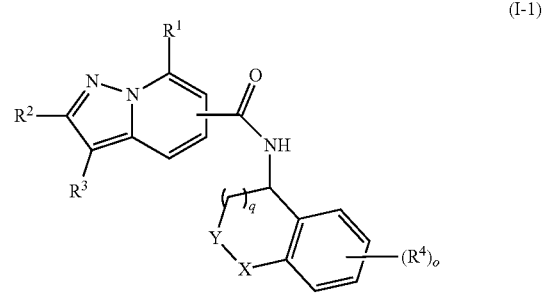

(I-1)

wherein:

$R^1$ is hydrogen, cyano, optionally substituted alkoxy, optionally substituted haloalkoxy optionally substituted aryloxy, optionally substituted alkyl, optionally substituted haloalkyl, optionally substituted $C_3$-$C_8$cycloalkyl, optionally substituted alkenyl, optionally substituted haloalkenyl, optionally substituted alkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$S(O)_n$, amino, NH-optionally substituted alkyl, or $NR^aR^b$ wherein $R^a$ and $R^b$ are independently optionally substituted alkyl; or $R^a$ and $R^b$ may form, with the nitrogen to which they are attached, a 3, 4, 5, 6, 7, or 8 membered-heterocyclyl group, which may be optionally substituted;

$R^2$ is hydrogen, halogen, cyano, optionally substituted alkoxy, optionally substituted aryloxy, optionally substituted alkyl, optionally substituted $C_3$-$C_8$-cycloalkyl, or $SO_m$(optionally substituted alkyl);

$R^3$ is selected from the group consisting of 6- or 10-membered aryl and 5- to 10-membered heteroaryl, each of which may be optionally substituted with 1, 2, 3, 4 or 5 substituents;

Each $R^4$ is independently hydrogen, halogen, cyano, nitro, —OH, optionally substituted alkyl, optionally substituted alkoxy, optionally substituted cycloalkyl, -amino, NH-optionally substituted alkyl, $SF_5$, or $NR^cR^d$ wherein $R^c$ and $R^d$ are independently optionally substituted alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted);

o is 0, 1, 2, 3, or 4;

m, n, and p are independently 0, 1, or 2;

q is 0 or 1;

X and Y are independently $CR^5R^6$, O, S, or N—$R^7$, wherein at least one of X and Y is $CR^5R^6$;

$R^5$ and $R^6$ are independently hydrogen, fluorine or $C_1$-$C_4$-alkyl;

$R^7$ is hydrogen or $C_1$-$C_4$-alkyl; or a stereoisomer, tautomer, N-oxide, hydrate, solvate, or salt thereof.

In some embodiments $R^1$ is hydrogen, cyano, optionally substituted $C_1$-$C_4$-alkoxy, optionally substituted $C_1$-$C_4$-haloalkoxy, optionally substituted aryloxy, optionally substituted $C_1$-$C_4$-alkyl, optionally substituted $C_1$-$C_4$-haloalkyl, optionally substituted $C_3$-$C_8$cycloalkyl, optionally substituted $C_1$-$C_4$-alkenyl, optionally substituted $C_1$-$C_4$-haloalkenyl, optionally substituted $C_1$-$C_4$-alkynyl, optionally substituted aryl; optionally substituted $C_1$-$C_4$-alkylcarbonyl, optionally substituted $C_1$-$C_4$-alkoxycarbonyl, optionally substituted aminocarbonyl, optionally substituted $C_1$-$C_4$-alkylaminocarbonyl, optionally substituted $C_1$-$C_4$-dialkylaminocarbonyl, optionally substituted alkyl-$SO_n$, halo-$C_1$-$C_4$-alkyl-$S(O)_n$, amino, NH-optionally substituted $C_1$-$C_4$-alkyl, or $NR^aR^b$ wherein $R^a$ and $R^b$ are independently optionally substituted alkyl; or $R^a$ and $R^b$ may form, with the nitrogen to which they are attached, a 3, 4, 5, 6, 7, or 8 membered-heterocyclyl group, which may be optionally substituted;

$R^2$ is hydrogen, halogen, cyano, optionally substituted $C_1$-$C_4$-alkoxy, optionally substituted aryloxy, optionally substituted $C_1$-$C_4$-alkyl, optionally substituted $C_3$-$C_8$-cycloalkyl, or $SO_m$(optionally substituted $C_1$-$C_4$-alkyl);

$R^3$ is selected from the group consisting of 6- or 10-membered aryl and 5- to 10-membered heteroaryl, each of which may be optionally substituted with 1, 2, 3, 4 or 5 substituents;

Each $R^4$ is independently hydrogen, halogen, cyano, nitro, —OH, optionally substituted $C_1$-$C_4$-alkyl, optionally substituted $C_1$-$C_4$-alkoxy, optionally substituted $C_3$-$C_8$-cycloalkyl, -amino, NH-optionally substituted $C_1$-$C_4$-alkyl, $SF_5$, or $NR^cR^d$ wherein $R^c$ and $R^d$ are independently optionally substituted $C_1$-$C_4$-alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted $C_1$-$C_4$-alkyl);

o is 0, 1, 2, 3, or 4;

m, n, and p are independently 0, 1, or 2;

q is 0 or 1;

X and Y are independently $CR^5R^6$, O, S, or N—$R^7$, wherein at least one of X and Y is $CR^5R^6$;

$R^5$ and $R^6$ are independently hydrogen, fluorine or $C_1$-$C_4$-alkyl;

$R^7$ is hydrogen or $C_1$-$C_4$-alkyl; or a stereoisomer, tautomer, N-oxide, hydrate, solvate, or salt thereof.

In some embodiments, $R^1$ is $C_1$-$C_4$-alkyl, $C_1$-$C_4$-haloalkyl, amino, $C_1$-$C_4$-alkyl alkylamino, or di-($C_1$-$C_4$alkyl) amino.

In some embodiments, $R^1$ is optionally substituted $C_1$-$C_4$-alkylthio.

In some embodiments, $R^1$ is optionally substituted $C_1$-$C_4$-alkylsulfinyl.

In some embodiments, $R^1$ is optionally substituted $C_1$-$C_4$-alkylsulfonyl.

In some embodiments, $R^1$ is optionally substituted $C_1$-$C_4$-haloalkylthio.

In some embodiments, $R^1$ is optionally substituted $C_1$-$C_4$-haloalkylsulfinyl.

In some embodiments, $R^1$ is optionally substituted $C_1$-$C_4$-haloalkylsulfonyl.

In some embodiments, $R^1$ is optionally substituted $C_1$-$C_4$-haloalkynyl.

In some embodiments, $R^1$ is hydrogen, cyano, optionally substituted $C_1$-$C_4$-alkoxy, optionally substituted $C_1$-$C_4$-haloalkoxy, optionally substituted aryloxy, optionally substituted $C_1$-$C_4$-alkyl, optionally substituted $C_1$-$C_4$-haloalkyl, optionally substituted $C_3$-$C_8$cycloalkyl, optionally substituted $C_1$-$C_4$-alkenyl, optionally substituted $C_1$-$C_4$-haloalkenyl, optionally substituted $C_1$-$C_4$-alkynyl, optionally substituted aryl; optionally substituted $C_1$-$C_4$-alkylcarbonyl, optionally substituted $C_1$-$C_4$-alkoxycarbonyl, optionally substituted aminocarbonyl, optionally substituted alkylaminocarbonyl, optionally substituted dialkylaminocarbonyl, optionally substituted alkyl-$SO_n$, haloalkyl-$S(O)_n$, amino, NH-optionally substituted alkyl, or $NR^aR^b$ wherein $R^a$ and $R^b$ are independently optionally substituted alkyl; or $R^a$ and $R^b$ may form, with the nitrogen to which they are attached, a 3, 4, 5, 6, 7, or 8 membered-heterocyclyl group, which may be optionally substituted;

In some embodiments $R^1$ is secondary $C_1$-$C_4$-alkyl.

In some embodiments, $R^1$ is heterocyclyl.

In some embodiments, $R^1$ is aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^1$ is aziridinyl, azetidinyl, oxetanyl, pyrrolidinyl, pyrrolyl, or morpholinyl, all of which are optionally substituted by one or more halogen.

In some embodiments, $R^2$ is hydrogen, alkyl, or haloalkyl.

In some embodiments, $R^2$ is alkyl or haloalkyl.

In some embodiments, $R^2$ is alkyl.

In some embodiments, $R^2$ is optionally substituted $C_1$-$C_4$-alkylthio.

In some embodiments, $R^2$ is optionally substituted $C_1$-$C_4$-alkylsulfinyl.

In some embodiments, $R^2$ is optionally substituted $C_1$-$C_4$-alkylsulfonyl.

In some embodiments, $R^2$ is optionally substituted $C_1$-$C_4$-haloalkylthio.

In some embodiments, $R^2$ is optionally substituted $C_1$-$C_4$-haloalkylsulfinyl.

In some embodiments, $R^2$ is hydrogen, halogen, cyano, optionally substituted $C_1$-$C_4$-alkoxy, optionally substituted aryloxy, optionally substituted $C_1$-$C_4$-alkyl, optionally substituted $C_3$-$C_8$-cycloalkyl, or $SO_m$(optionally substituted $C_1$-$C_4$-alkyl).

In some embodiments, $R^2$ is optionally substituted $C_1$-$C_4$-haloalkylsulfonyl. In some embodiments, $R^3$ is 6- or 10-membered aryl optionally substituted with 1, 2, 3, 4 or 5 substituents.

In some embodiments, $R^3$ is 5- to 10-membered heteroaryl optionally substituted with 1, 2, 3, 4 or 5 substituents.

In some embodiments, $R^3$ is phenyl substituted with 1 substituent which is halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is para-substituted phenyl.

In some embodiments, $R^3$ is meta-substituted phenyl.

In some embodiments, $R^3$ is ortho-substituted phenyl.

In some embodiments, $R^3$ is halophenyl.

In some embodiments $R^3$ is haloalkylphenyl.

In some embodiments, $R^3$ is haloalkoxyphenyl.

In some embodiments, $R^3$ is phenyl substituted with 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2,3-disubstituted phenyl.

In some embodiments, $R^3$ is 2,4-disubstituted phenyl.

In some embodiments, $R^3$ is 2,5-disubstituted phenyl.

In some embodiments, $R^3$ is dihalophenyl, e.g., dichloro; difluoro; or chloro, fluoro.

In some embodiments $R^3$ is phenyl substituted with halo and haloalkyl.

In some embodiments $R^3$ is phenyl substituted with halo and haloalkoxy.

In some embodiments $R^3$ is phenyl substituted with haloalkyl and haloalkoxy.

In some embodiments, $R^3$ is phenyl substituted with 3 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is trihalophenyl, e.g., trichloro; trifluoro; or chloro, chloro, fluoro, or fluoro, fluoro, chloro.

In some embodiments $R^3$ is phenyl substituted with 2 halo and haloalkyl.

In some embodiments $R^3$ is phenyl substituted with 2 halo and haloalkoxy.

In some embodiments $R^3$ is phenyl substituted with 1 haloalkyl, 1 halo, and 1 haloalkoxy.

In some embodiments $R^3$ is phenyl substituted with 1 halo and 2 haloalkyl.

In some embodiments, $R^3$ is 5-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 6-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 3-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 4-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, q is 0.

In some embodiments, q is 1.

In some embodiments, X is $CH_2$.

In some embodiments, X is O.

In some embodiments, X is S.

In some embodiments, X is S=O.

In some embodiments, X is $SO_2$.

In some embodiments, X is NH.

In some embodiments, X is NCOalkyl

In some embodiments, X is N aryl

In some embodiments, Y is $CH_2$.

In some embodiments, Y is CHalkyl.

In some embodiments, Y is CHaryl.

In some embodiments, the compound of formula (I) is the compound of formula (Ia):

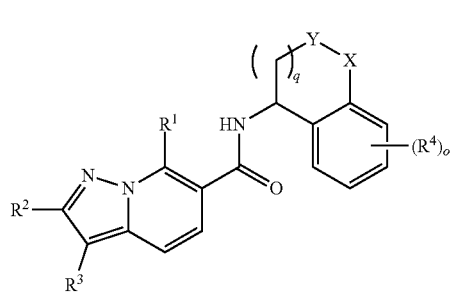

(Ia)

wherein the definition of variables R¹, R², R³, R⁴, X, Y, q and o is the same as for formula (I).

In some embodiments, the compound of formula (I) is the compound of formula (Ib):

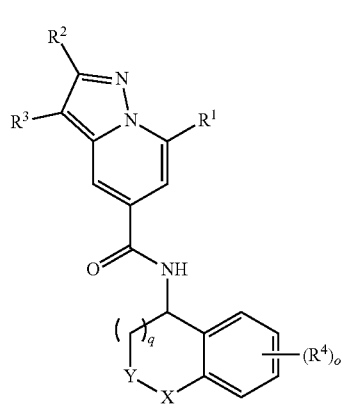

(Ib)

wherein the definition of variables R¹, R², R³, R⁴, X, Y, q and o is the same as for formula (I).

In some embodiments, the compound of formula (I) is the compound of formula (Ic):

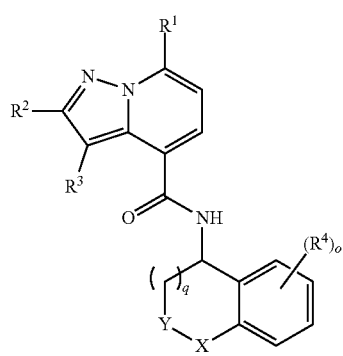

(Ic)

wherein the definition of variables R¹, R², R³, R⁴, X, Y, q and o is the same as for formula (I).

In some embodiments, the compound of formula (I) is the compound of formula (Id):

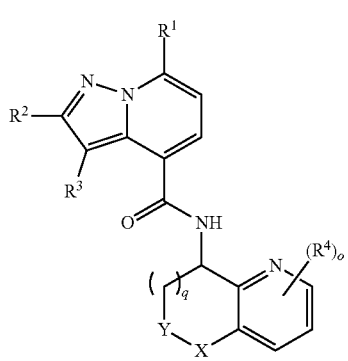

(Id)

wherein the definition of variables R¹, R², R³, R⁴, X, Y, q and o is the same as for formula (I).

In some embodiments, the compound of formula (I) is the compound of formula (Ie):

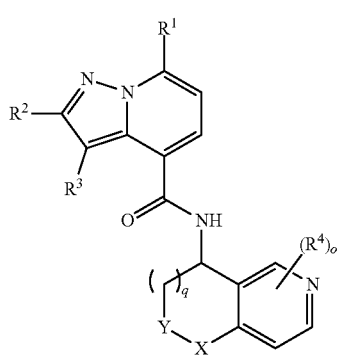

(Ie)

wherein the definition of variables R¹, R², R³, R⁴, X, Y, q and o is the same as for formula (I).

In some embodiments, the compound of formula (I) is the compound of formula (If):

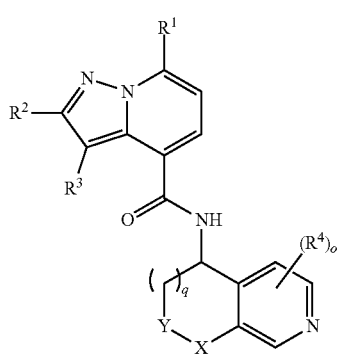

(If)

wherein the definition of variables R¹, R², R³, R⁴, X, Y, q and o is the same as for formula (I).

In some embodiments, the compound of formula (I) is the compound of formula (Ig):

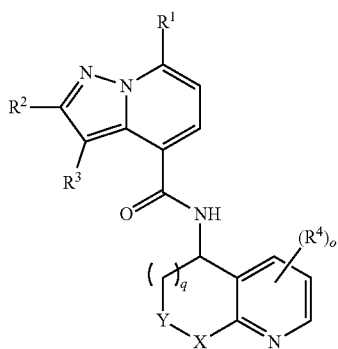

(Ig)

wherein the definition of variables $R^1$, $R^2$, $R^3$, $R^4$, X, Y, q and o is the same as for formula (I).

In some embodiments, the compound of formula (I) is the compound of formula (Ih):

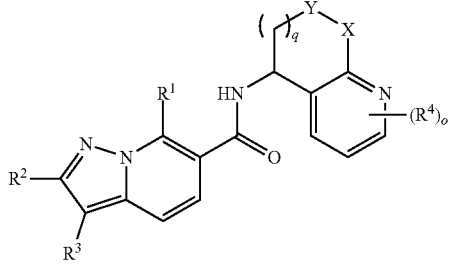

(Ih)

wherein the definition of variables $R^1$, $R^2$, $R^3$, $R^4$, X, Y, q and o is the same as for formula (I).

In some embodiments, the compound of formula (I) is the compound of formula (Ii):

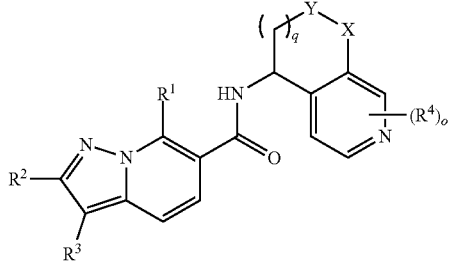

(Ii)

wherein the definition of variables $R^1$, $R^2$, $R^3$, $R^4$, X, Y, q and o is the same as for formula (I).

In some embodiments, the compound of formula (I) is the compound of formula (Ij):

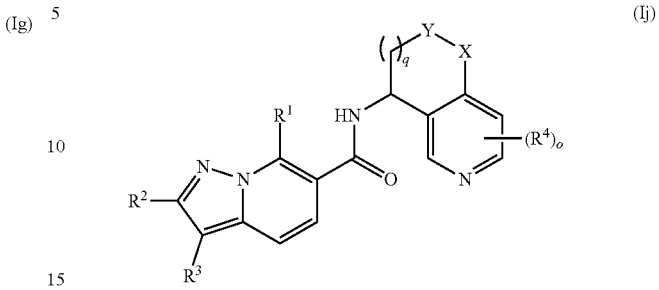

(Ij)

wherein the definition of variables $R^1$, $R^2$, $R^3$, $R^4$, X, Y, q and o is the same as for formula (I).

In some embodiments, the compound of formula (I) is the compound of formula (Ik):

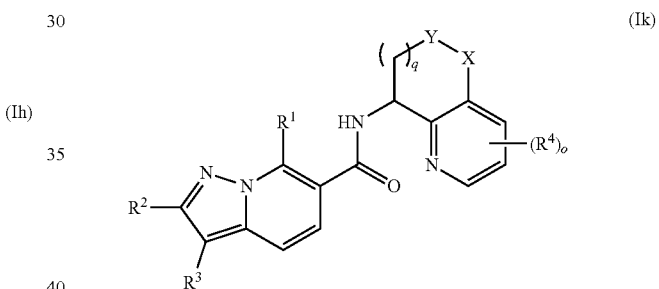

(Ik)

wherein the definition of variables $R^1$, $R^2$, $R^3$, $R^4$, X, Y, q and o is the same as for formula (I).

In some embodiments, the compound of formula (I) is the compound of formula (Il):

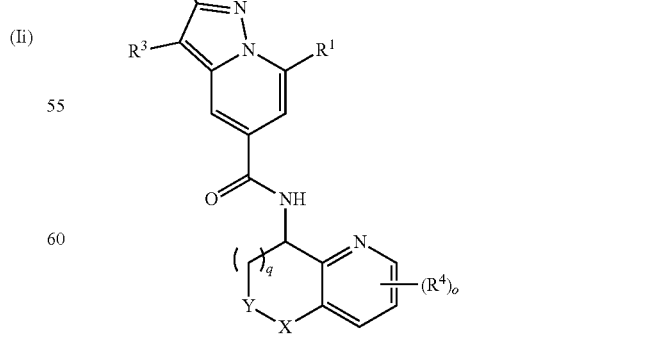

(Il)

wherein the definition of variables $R^1$, $R^2$, $R^3$, $R^4$, X, Y, q and o is the same as for formula (I).

In some embodiments, the compound of formula (I) is the compound of formula (Im):

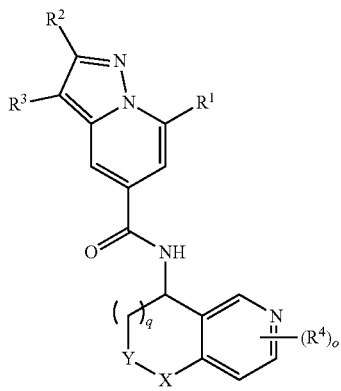

(Im)

wherein the definition of variables $R^1$, $R^2$, $R^3$, $R^4$, X, Y, q and o is the same as for formula (I).

In some embodiments, the compound of formula (I) is the compound of formula (In):

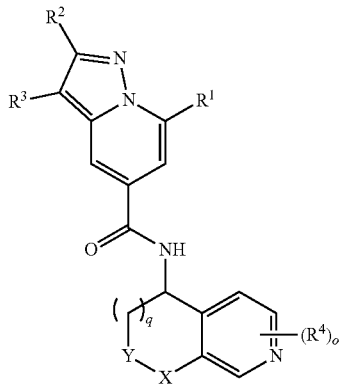

(In)

wherein the definition of variables $R^1$, $R^2$, $R^3$, $R^4$, X, Y, q and o is the same as for formula (I).

In some embodiments, the compound of formula (I) is the compound of formula (Io):

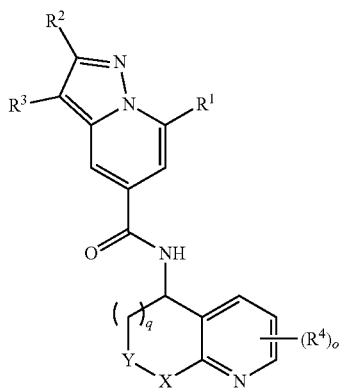

(Io)

wherein the definition of variables $R^1$, $R^2$, $R^3$, $R^4$, X, Y, q and o is the same as for formula (I).

In some embodiments, the compound of formula (I) is the compound of formula (Ip), (Iq) or (Ir):

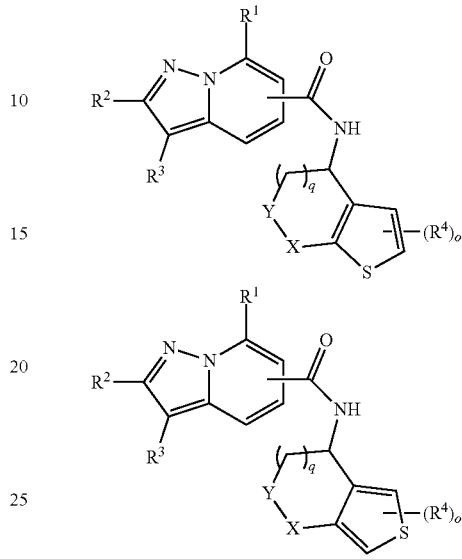

wherein the definition of variables $R^1$, $R^2$, $R^3$, $R^4$, X, Y, q and o is the same as for formula (IA)

In some embodiments, o is 0.
In some embodiments, o is 1.
In some embodiments, o is 2.
In some embodiments, o is 3.
In some embodiments, o is 4.
In some embodiments, an $R^4$ is, independently of other $R^4$, a halogen.
In some embodiments, an $R^4$ is, independently of other $R^4$, optionally substituted $C_1$-$C_4$ alkyl.
In some embodiments, $R^4$ is, independently of other $R^4$, haloalkyl.

In an embodiment, the description includes the compound of formula (II):

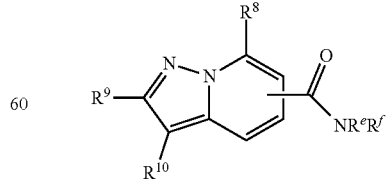

(II)

wherein:
$R^8$ is hydrogen, cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$S(O)_n$, amino, NH-optionally substituted alkyl, or $NR^{a'}R^{b'}$ wherein $R^{a'}$ and $R^{b'}$ are independently optionally substituted $C_1$-$C_4$ alkyl; or $R^{a'}$ and $R^{b'}$ may form, with the nitrogen to which they are attached, a 3, 4, 5, 6, 7, or 8 membered-heterocyclyl group, which may be optionally substituted;

$R^9$ is hydrogen, halogen, cyano, optionally substituted alkoxy, optionally substituted aryloxy, optionally substituted alkyl, optionally substituted cycloalkyl, or $SO_m$ (optionally substituted alkyl);

$R^{10}$ is selected from the group consisting of 6 or 10-membered aryl and 5 to 10-membered heteroaryl, each of which may be optionally substituted with 1, 2, 3, 4 or 5 substituents;

$R^e$ and $R^f$ are independently hydrogen, optionally substituted alkyl, optionally substituted aryl, and optionally substituted heteroaryl; or $R^e$ and $R^f$ may form, with the nitrogen to which they are attached, a 3, 4, 5, 6, 7, or 8 membered-heterocyclyl group, which may be optionally substituted; and m and m are 0, 1 or 2; or a stereoisomer, tautomer, N-oxide, hydrate, solvate, or salt thereof.

In some embodiments $R^8$ is hydrogen, cyano, optionally substituted $C_1$-$C_4$-alkoxy, optionally substituted $C_1$-$C_4$-haloalkoxy, optionally substituted aryloxy, optionally substituted $C_1$-$C_4$-alkyl, optionally substituted $C_1$-$C_4$-haloalkyl, optionally substituted $C_3$-$C_8$-cycloalkyl, optionally substituted $C_1$-$C_4$-alkenyl, optionally substituted $C_1$-$C_4$-haloalkenyl, optionally substituted $C_1$-$C_4$-alkynyl, optionally substituted aryl; optionally substituted $C_1$-$C_4$-alkylcarbonyl, optionally substituted $C_1$-$C_4$-alkoxycarbonyl, optionally substituted $C_1$-$C_4$-aminocarbonyl, optionally substituted $C_1$-$C_4$-alkylaminocarbonyl, optionally substituted $C_1$-$C_4$-dialkylaminocarbonyl, optionally substituted $C_1$-$C_4$-alkyl-$SO_n$, $C_1$-$C_4$-haloalkyl-$S(O)_n$, amino, NH-optionally substituted $C_1$-$C_4$-alkyl, or $NR^{a'}R^{b'}$ wherein $R^{a'}$ and $R^{b'}$ are independently optionally substituted $C_1$-$C_4$ alkyl; or $R^{a'}$ and $R^{b'}$ may form, with the nitrogen to which they are attached, a 3, 4, 5, 6, 7, or 8 membered-heterocyclyl group, which may be optionally substituted;

$R^9$ is hydrogen, halogen, cyano, optionally substituted $C_1$-$C_4$-alkoxy, optionally substituted aryloxy, optionally substituted $C_1$-$C_4$-alkyl, optionally substituted $C_3$-$C_6$-cycloalkyl, or $SO_m$(optionally substituted $C_1$-$C_4$-alkyl);

$R^{10}$ is selected from the group consisting of 6 or 10-membered aryl and 5 to 10-membered heteroaryl, each of which may be optionally substituted with 1, 2, 3, 4 or 5 substituents;

$R^e$ and $R^f$ are independently hydrogen, optionally substituted $C_1$-$C_4$-alkyl, optionally substituted aryl, and optionally substituted heteroaryl; or $R^e$ and $R^f$ may form, with the nitrogen to which they are attached, a 3, 4, 5, 6, 7, or 8 membered-heterocyclyl group, which may be optionally substituted; and m and m are 0, 1 or 2; or a stereoisomer, tautomer, N-oxide, hydrate, solvate, or salt thereof.

In some embodiments, $R^8$ is $C_1$-$C_4$-alkyl, $C_1$-$C_4$-haloalkyl, amino, $C_1$-$C_4$-alkyl alkylamino, or di-($C_1$-$C_4$alkyl) amino.

In some embodiments, $R^8$ is optionally substituted $C_1$-$C_4$-alkylthio.

In some embodiments, $R^8$ is optionally substituted $C_1$-$C_4$-alkylsulfinyl.

In some embodiments, $R^8$ is optionally substituted $C_1$-$C_4$-alkylsulfonyl.

In some embodiments, $R^8$ is optionally substituted $C_1$-$C_4$-haloalkylthio.

In some embodiments, $R^8$ is optionally substituted $C_1$-$C_4$-haloalkylsulfinyl.

In some embodiments, $R^8$ is optionally substituted $C_1$-$C_4$-haloalkylsulfonyl.

In some embodiments $R^8$ is secondary $C_1$-$C_4$-alkyl.

In some embodiments, $R^8$ is heterocyclyl.

In some embodiments, $R^8$ is aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^8$ is aziridinyl, azetidinyl, oxetanyl, pyrrolidinyl, pyrrolyl, or morpholinyl, all of which are optionally substituted by one or more halogen.

In some embodiments, $R^8$ is hydrogen, cyano, optionally substituted $C_1$-$C_4$-alkoxy, optionally substituted $C_1$-$C_4$-haloalkoxy, optionally substituted aryloxy, optionally substituted $C_1$-$C_4$-alkyl, optionally substituted $C_1$-$C_4$-haloalkyl, optionally substituted $C_3$-$C_8$-cycloalkyl, optionally substituted $C_1$-$C_4$-alkenyl, optionally substituted $C_1$-$C_4$-haloalkenyl, optionally substituted $C_1$-$C_4$-alkynyl, optionally substituted aryl; optionally substituted $C_1$-$C_4$-alkylcarbonyl, optionally substituted $C_1$-$C_4$-alkoxycarbonyl, optionally substituted aminocarbonyl, optionally substituted alkylaminocarbonyl, optionally substituted dialkylaminocarbonyl, optionally substituted alkyl-$SO_n$, haloalkyl-$S(O)_n$, amino, NH-optionally substituted alkyl, or $NR^aR^b$ wherein $R^{a'}$ and $R^{b'}$ are independently optionally substituted $C_1$-$C_4$ alkyl; or $R^{a'}$ and $R^{b'}$ may form, with the nitrogen to which they are attached, a 3, 4, 5, 6, 7, or 8 membered-heterocyclyl group, which may be optionally substituted;

In some embodiments, $R^9$ is hydrogen, halogen, cyano, optionally substituted $C_1$-$C_4$-alkoxy, optionally substituted aryloxy, optionally substituted $C_1$-$C_4$-alkyl, optionally substituted $C_3$-$C_6$-cycloalkyl, or $SO_m$(optionally substituted $C_1$-$C_4$-alkyl);

In some embodiments, $R^{10}$ is selected from the group consisting of 6 or 10-membered aryl and 5 to 10-membered heteroaryl, each of which may be optionally substituted with 1, 2, 3, 4 or 5 substituents;

In some embodiments $R^e$ and $R^f$ are independently hydrogen, optionally substituted $C_1$-$C_4$-alkyl, optionally substituted aryl, and optionally substituted heteroaryl; or $R^e$ and $R^f$ may form, with the nitrogen to which they are attached, a 3, 4, 5, 6, 7, or 8 membered-heterocyclyl group, which may be optionally substituted.

In some embodiments, $R^9$ is hydrogen, alkyl, or haloalkyl.

In some embodiments, $R^9$ is alkyl or haloalkyl.

In some embodiments, $R^9$ is alkyl.

In some embodiments, $R^9$ is optionally substituted $C_1$-$C_4$-alkylthio.

In some embodiments, $R^9$ is optionally substituted $C_1$-$C_4$-alkylsulfinyl.

In some embodiments, $R^9$ is optionally substituted $C_1$-$C_4$-alkylsulfonyl.

In some embodiments, $R^9$ is optionally substituted $C_1$-$C_4$-haloalkylthio.

In some embodiments, $R^9$ is optionally substituted $C_1$-$C_4$-haloalkylsulfinyl.

In some embodiments, $R^9$ is optionally substituted $C_1$-$C_4$-haloalkylsulfonyl.

In some embodiments, $R^{10}$ is 6- or 10-membered aryl optionally substituted with 1, 2, 3, 4 or 5 substituents.

In some embodiments, $R^{10}$ is 5- to 10-membered heteroaryl optionally substituted with 1, 2, 3, 4 or 5 substituents.

In some embodiments, $R^{10}$ is phenyl substituted with 1 substituent which is halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is para-substituted phenyl.

In some embodiments, $R^{10}$ is meta-substituted phenyl.

In some embodiments, $R^{10}$ is ortho-substituted phenyl.

In some embodiments, $R^{10}$ is halophenyl.

In some embodiments $R^{10}$ is haloalkylphenyl.

In some embodiments, $R^{10}$ is haloalkoxyphenyl.

In some embodiments, $R^3$ is phenyl substituted with 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is 2,3-disubstituted phenyl.

In some embodiments, $R^{10}$ is 2,4-disubstituted phenyl.

In some embodiments, $R^{10}$ is 2,5-disubstituted phenyl.

In some embodiments, $R^{10}$ is dihalophenyl, e.g., dichloro; difluoro; or chloro, fluoro.

In some embodiments $R^{10}$ is phenyl substituted with halo and haloalkyl.

In some embodiments $R^{10}$ is phenyl substituted with halo and haloalkoxy.

In some embodiments $R^{10}$ is phenyl substituted with haloalkyl and haloalkoxy.

In some embodiments, $R^3$ is phenyl substituted with 3 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is trihalophenyl, e.g., trichloro; trifluoro; or chloro, chloro, fluoro, or fluoro, fluoro, chloro.

In some embodiments $R^{10}$ is phenyl substituted with 2 halo and haloalkyl.

In some embodiments $R^{10}$ is phenyl substituted with 2 halo and haloalkoxy.

In some embodiments $R^{10}$ is phenyl substituted with 1 haloalkyl, 1 halo, and 1 haloalkoxy.

In some embodiments $R^{10}$ is phenyl substituted with 1 halo and 2 haloalkyl.

In some embodiments, $R^{10}$ is 5-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is 6-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is 2-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is 3-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^{10}$ is 4-pyridyl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^e$ is hydrogen.

In some embodiments, $R^f$ is hydrogen.

In some embodiments, $R^f$ is optionally substituted alkyl.

In some embodiments, $R^f$ is alkyl substituted with aryl.

In some embodiments, $R^f$ is alkyl substituted with heteroaryl.

In some embodiments, the compound of formula (II) is the compound of formula (IIa):

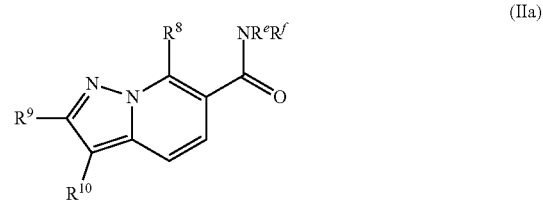

(IIa)

wherein variables $R^8$, $R^9$, $R^{10}$, $R^e$ and $R^f$ are as defined for the compound of formula (II).

In some embodiments, the compound of formula (II) is the compound of formula (IIb):

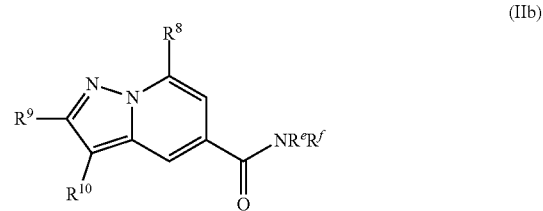

(IIb)

wherein variables $R^8$, $R^9$, $R^{10}$, $R^e$ and $R^f$ are as defined for the compound of formula (II).

In some embodiments, the compound of formula (II) is the compound of formula (IIc):

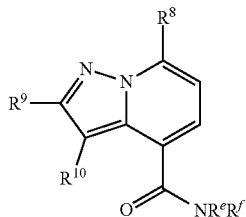

(IIc)

wherein variables $R^8$, $R^9$, $R^{10}$, $R^e$ and $R^f$ are as defined for the compound of formula (II).

Stereoisomers and Polymorphic Forms

It will be appreciated by those of skill in the art that the compound may exist and be isolated in optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the description may include one or more chiral centers, which results in a theoretical number of optically active isomers. Where compounds of the description include n chiral centers, the compounds may comprise up to $2^n$ optical isomers. The description encompasses the specific enantiomers or diastereomers of each compound as well as mixtures of different enantiomers and/or diastereomers of the compounds that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compound may also be present in different solid forms such as different crystalline forms or in the form of an amorphous solid. The description includes different crystalline forms as well as amorphous forms of the compound.

In addition, the compound may exist as hydrates or solvates, in which a certain stoichiometric amount of water or a solvent is associated with the molecule in the crystalline form. The hydrates and solvates of the compound are also the subject of the description.

Salts

In addition to the neutral compound, salt forms of the compound are also active against endoparasites. The term "veterinarily acceptable salt" is used throughout the specification to describe any salts of the compounds that are acceptable for administration for veterinary applications, and which provides an active compound upon administration.

In cases where compounds are sufficiently basic or acidic to form stable non-toxic acid or base salts, the compound may be in the form of a veterinarily or agriculturally acceptable salt. Veterinarily acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the description.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compound can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the description.

Processes for the Preparation of the Compounds:

In some embodiments, the compound of formula I may be prepared by reacting a compound of formula III:

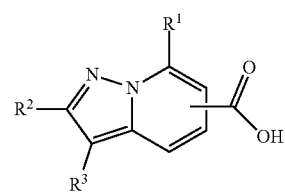

(III)

with a compound of formula (IV):

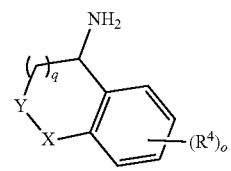

(IV)

in the presence of a coupling reagent. Suitable coupling reagents include, but are not limited to, a diimide, e.g., dicyclohexylcarbodiimide, and a phosphonium or uranium reagent, e.g., BOP, PyBOP, and/or HBTU as understood by a person of ordinary skill in the art.

In some embodiments, the compound of formula (II) may be prepared by reacting a compound of formula III:

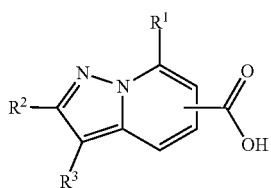
(III)

with an amine of formula HNR$^e$R$^f$ in the presence of a coupling reagent, such as dicyclohexylcarbodiimide.

In some embodiments, the compound of formula (III) may be prepared by acid or base hydrolysis of a compound of formula (V):

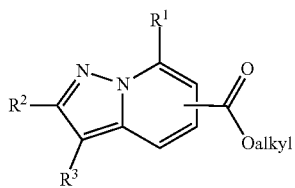
(V)

In some embodiments, the compound of formula (V), wherein R$^1$ is optionally substituted alkyl, optionally substituted C$_3$-C$_8$-cycloalkyl, optionally substituted alkenyl, optionally substituted alkynyl, optionally substituted aryl, optionally substituted alkylcarbonyl, optionally substituted alkoxycarbonyl, and optionally substituted alkyl-SO$_n$, may be prepared by reacting a compound of formula (VI):

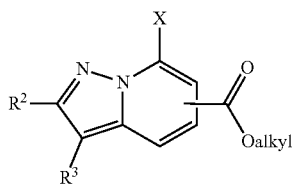
(VI)

wherein X is a halogen, preferably Br or I, with a borolane of formula R$^{11}$—BOR$^g$OR$^h$, wherein R$^{11}$ comprises an alkene directly attached to borane and R$^g$ and R$^h$ are alkyl or hydrogen, in the presence of a Palladium(0) catalyst; and subsequently, the R$^{11}$ group is hydrogenated. In some embodiments, the R$^1$—BOR$^g$OR$^h$, may be directly reacted with the compound of formula (VI).

In some embodiments, the compound of formula (V), wherein R$^1$ is amino, NH-optionally substituted C$_1$-C$_4$-alkyl, or NR$^a$R$^b$ wherein R$^a$ and R$^b$ are independently optionally substituted C$_1$-C$_4$ alkyl; or R$^a$ and R$^b$ may form, with the nitrogen to which they are attached, a 3, 4, 5, 6, 7, or 8 membered-heterocyclyl group, which may be optionally substituted, may be prepared by reacting a compound of formula (VI) with ammonia, NH$_2$-optionally substituted C$_1$-C$_4$-alkyl, or HNR$^a$R$^b$ wherein R$^a$ and R$^b$ are independently optionally substituted C$_1$-C$_4$ alkyl; or R$^a$ and R$^b$ may form, with the nitrogen to which they are attached, a 3, 4, 5, 6, 7, or 8 membered-heterocyclyl group, which may be optionally substituted.

In some embodiments, the compound of formula (VI) may be prepared by reacting a compound of formula (VII):

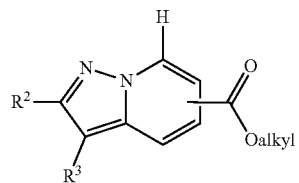
(VII)

with a strong base, e.g., lithium diisopropyl amide, then a halogenating agent, e.g., carbon tetrabromide, or carbon tetraiodide.

In some embodiments, the compound of formula (VII) may be prepared by reacting the compound of formula (VIII):

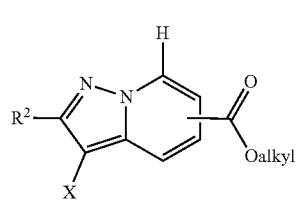
(VIII)

wherein X is halogen, preferably Br or I, with a borolane of formula R$^3$—BOR$^g$OR$^h$, wherein R$^g$ and R$^h$ are alkyl or hydrogen, in the presence of a Palladium(0) catalyst.

In some embodiments, the compound of formula (VIII) may be prepared by reacting the compound of formula (IX):

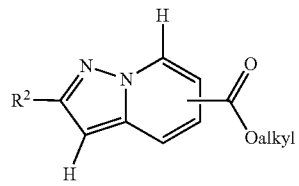
(IX)

with a halogenating compound, e.g., PBr$_3$ or N-bromosuccinimide, or N-chlorosuccinimide.

In some embodiments, a compound of formula (IX) may be a compound of formula (IXa), (IXb) or (IXc):

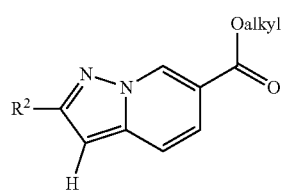
(IXa)

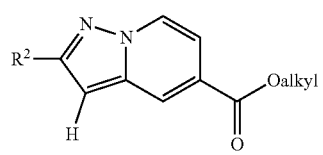
(IXb)

-continued

(IXc)

In some embodiments, a compound of (IXa) or (IXb) may be prepared by reacting a salt of formula X⁺Y⁻, wherein X⁺ is:

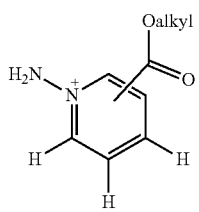
(X⁺)

and wherein Y⁻ is an anionic counterion, with a compound of formula (XI):

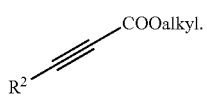
(XI)

In some embodiments, the compound of formula (IXc) may be prepared by reacting the compound of formula (XI) with a salt of formula Xc⁺Y⁻, wherein Xc⁺ is:

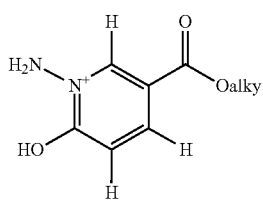
(Xc⁺)

to provide a compound of formula XII:

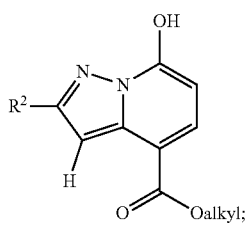
(XII)

and subsequently reacting the compound of formula XII under dihydroxylation conditions by methods known to person of skill in the art, e.g., by the method of U.S. Pat. No. 4,451,356.

In some embodiments, the compound of formula (I) wherein $R^1$ is cyano, optionally substituted alkoxy, or optionally substituted aryloxy, may be prepared by reacting a compound of formula (I), wherein $R^1$ is halogen, with a cyanide ion, an optionally substituted alkoxide anion, and an optionally substituted aryloxide anion, respectively.

In some embodiments, the compound of formula (I) wherein $R^1$ is halogen, may be prepared by reacting a compound of formula (I), wherein $R^1$ is hydroxyl, with a halogenating agent, e.g., $PBr_3$, $PCl_3$, or Vilsmeier's reagent.

In some embodiments, the compound of formula (I), wherein $R^1$ is hydroxyl, may be prepared by reacting the salt of formula X⁺Y⁻ or salt of formula Xc⁺Y⁻ with a compound of formula $alkylOCOCH_2R^3$.

These teachings are general and it is believed they are adaptable by a person of ordinary skill.

Veterinary Compositions:

The compound and compositions comprising the compound are useful for the prevention and treatment of parasitic infestations/infections in animals. The compositions of the description comprise an effective amount of a compound or a veterinarily acceptable salt thereof, in combination with a veterinarily acceptable carrier or diluent and optionally a non-active excipient. The compositions may be in a variety of solid and liquid forms which are suitable for various forms of application or administration to an animal. For example, the veterinary compositions comprising the compound may be in compositions suitable for oral administration, injectable administration, including subcutaneous and parenteral administration, and topical administration (e.g. spot-on or pour-on), dermal or subdermal administration. The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compound to protect companion animals such as dogs and cats from endoparasites is particularly useful.

As discussed above, the compositions of the description may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench compositions, dispersible powders or granules, premixes, syrups or elixirs, enteric compositions or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral compositions include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In one embodiment, the compound may be administered in chewable tablet compositions or soft chewable compositions such as those described in US 2013/0203692 A1, US 2010/0087492, US 2006/0222684, US 2004/0151759, U.S. Pat. No. 7,955,632, all incorporated herein by reference. The veterinary compositions may be in the form of a soft chewable composition ("soft chew") which is palatable and acceptable to the animal. In addition to the active ingredient(s), the soft chews of the description may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the description include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE®), or a combination thereof.

Various fillers known in the art may be used in the soft chewable compositions of the description. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the description include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the composition to improve their solubility and absorption after ingestion. Surfactants are typically present in a concentration of about 1 to 10% (w/w), more typically about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like.

The compositions may contain other inert ingredients such as antioxidants, preservatives, or pH stabilizers. These compounds are well known in the composition art. Antioxidants may be added to the compositions of the description to inhibit degradation of the active agents. Suitable antioxidants include, but are not limited to, alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The compositions of the description may also include one or more lubricants and/or processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil.

Many flavoring agents may be used in the compositions of the description to improve the palatability of the oral veterinary compositions. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the description, the active composition may be administered via a drench, and may be administered either topically or orally. Drench compositions are those in which the liquid-containing compositions of the description are administered to the mouth or throat of the animal, or poured onto the skin or coat of the animal.

The compositions of the description may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the description may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same composition. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such compositions may also contain a demulcent, a preservative, flavoring agent(s) and/or coloring agent(s).

In another embodiment of the description, the composition may be in paste form. Examples of embodiments in a paste form include, but are not limited to, those described in U.S. Pat. Nos. 6,787,342 and 7,001,889 (each of which are incorporated herein by reference). In addition to the compounds of the description, the paste may further contain fumed silica; a viscosity modifier; a carrier; optionally, an absorbent; and optionally, a colorant, stabilizer, surfactant, or preservative.

In one embodiment of the composition, the composition may be a paste containing the compounds of the description, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal compositions may include, by way of non-limiting example, emulsions, creams, ointments, gels, pastes, powders, shampoos, pour-on compositions, ready-to-use compositions, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on compositions are typically applied in a localized region which refers to an area other than the entire animal. In one embodiment, the location may be between the shoulders. In another embodiment it may be a stripe, e.g. a stripe from head to tail of the animal.

Pour-on compositions are described in U.S. Pat. No. 6,010,710, also incorporated herein by reference. Pour-on compositions may be advantageously oily, and generally comprise a diluent or vehicle and also a solvent (e.g. an organic solvent) for the active ingredient if the latter is not soluble in the diluent.

Organic solvents that can be used in the description include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the compositions may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the description, an emollient and/or spreading and/or film-forming agent may be added. In one embodiment, the emollient and/or spreading and/or film-forming agent may be:
(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil,
(b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil),
(c) cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used,
(d) amine salts of formula $N^+HR'R''R'''$ in which the radicals R are optionally hydroxylated hydrocarbon radicals; octadecylamine hydrochloride is among the cationic surfactants which can be used,
(e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide,
(f) amphoteric surfactants such as the substituted lauryl compounds of betaine; or
(g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the description, the composition may be in ready-to-use solution form as is described in U.S. Pat. No. 6,395,765, incorporated herein by reference. In addition to the compounds of the description, the ready-to-use solution may contain a crystallization inhibitor and an organic solvent or a mixture of organic solvents. In some embodiments, water may be included with the organic solvent.

In various embodiments of the description, the compositions may include a crystallization inhibitor in an amount of about 1 to about 50% (w/v) or about 5 to about 40% (w/v) based on the total weight of the composition. In other embodiments, the amount of crystallization inhibitor in the inventive compositions may be about 1% to about 30%, about 5% to about 20%, about 1% to about 15%, or about 1% to about 10% (w/w). The type of crystallization inhibitor used in the inventive compositions is not limited as long as it functions to inhibit crystallization of the active or inactive agents from the composition. For example, in certain embodiments of the description, a solvent or co-solvent of the composition may also function as a crystallization inhibitor if it sufficiently inhibits the formation of crystals from forming over time when the composition is administered.

Crystallization inhibitors which are useful for the description include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the composition is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the composition.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The composition may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the description, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present description. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The composition adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the composition applied will depend on the type of animal and the size of the animal as well as the strength of the composition and the potency of the active agents. In one embodiment, an amount of about 0.1 to about 20 ml of the composition may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the description, application of a spot-on composition according to the present description may also provide long-lasting and broad-spectrum efficacy when the solution is applied to the mammal or bird. The spot-on compositions provide for topical administration of a concentrated solution, suspension, microemulsion or emulsion for intermittent application to a spot on the animal, generally between the two shoulders (solution of spot-on type).

For spot-on compositions, the carrier may be a liquid carrier vehicle as described in U.S. Pat. No. 6,426,333 (incorporated herein by reference), which in one embodiment of the spot-on composition may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on compositions may be prepared by dissolving the active ingredients into the pharmaceutically or veterinary acceptable vehicle. Alternatively, the spot-on composition may be prepared by encapsulation of the active ingredient to leave a residue of the therapeutic agent on the surface of the animal. These compositions will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the description, the active agent may be present in the composition at a concentration of about 0.05 to about 10% weight/volume. In another embodiment of the description, the active agent may be present in the composition as a concentration from about 0.1 to about 2% weight/volume. In yet another embodiment of the description, the active agent may be present in the composition as a concentration from about 0.25 to about 1.5% weight/volume. In still another embodiment of the description, the active agent may be present in the composition as a concentration about 1% weight/volume.

II. Methods of Treatment:

As discussed above, the compound are effective against endoparasites and may be used to treat and prevent parasitic infections in or on animals. In one embodiment, the present description provides a method of treating or preventing an endoparasite infection in or on an animal (e.g. a mammal or bird) comprising administering an endoparasiticidally effective amount of a compound of formula (I), or veterinarily acceptable salts thereof, or a composition of the description, to the animal.

The compound may also effective against ectoparasites and may be used to treat and prevent ectoparasitic infestations on animals. In another embodiment, the present description provides a method of treating or preventing an ectoparasitic infestation on an animal (e.g. a mammal or bird) comprising administering an ectoparasiticidally effective amount of a compound of formula (I), or veterinarily acceptable salts thereof, or a composition of the description, to the animal.

In another embodiment, the description provides a method for treating or preventing an endoparasitic infection and an ectoparasitic infestation in and on an animal, comprising administering a composition comprising an effective amount of a compound of formula (I) in combination with an effective amount of at least a second active agent, or veterinarily acceptable salts thereof, to the animal.

In still another embodiment of the description, a method is provided for the treatment or prevention of a parasitic infestation at a locus, which comprises administering or applying a parasiticidally effective amount of a compound of formula (I), or veterinarily acceptable salts thereof, to the locus. With respect to animal health applications, "locus" is intended to mean a habitat, breeding ground, area, material or environment in which a parasite is growing or may grow, excluding in or on an animal.

In another embodiment, the description provides methods and uses of the compound for controlling pests in plants and crops or for protecting wood-containing structures.

Mammals which can be treated include but are not limited to humans, cats, dogs, cattle, chickens, cows, bison, deer, goats, horses, llamas, camels, pigs, sheep and yaks. In one embodiment of the description, the mammals treated are humans, cats or dogs.

In one embodiment of the description, the compound have been superior efficacy against endoparasites, and in particular against endoparasites that are resistant to active agents of the macrocyclic lactone class. In one embodiment, the compounds and compositions of the description are effective for controlling *Haemonchus contortus, Ostertagia circumcincta* and *Trichostrongylus colubriformis* in mammals or birds.

In another embodiment, the description provides a method for treating an parasitic infestation or infection in an animal, comprising administering an effective amount of an anthelmintic compound of the description in combination with an effective amount of activators of invertebrate GABA receptors including an avermectin or milbemycin to the animal in need thereof. Avermectins that may be used in combination with the compounds of the description include, but are not limited to abamectin, dimadectin, doramectin, emamectin, eprinomectin, ivermectin, latidectin, lepimectin, and selamectin Milbemycins compounds that may be used in combination with the compounds of the description include, but are not limited to, milbemectin, milbemycin D, moxidectin and nemadectin. Also included are the 5-oxo and 5-oxime derivatives of said avermectins and milbemycins.

In one embodiment, the compounds and compositions of the description may be used for treating or preventing an endoparasitic infection of the following parasite: *Anaplocephala* (*Anoplocephala*), *Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In a particularly preferred embodiment of the description, the compounds and compositions of the description are used to treat or prevent an infection by *Dirofilaria immitis*. The compound have been found to be highly effective against *D. immitis* microfilaria and L4 larvae. Thus, the compound may be used to protect animals from developing heartworm disease by killing the immature stages of *D. immitis* before they can develop into adult worms. In one embodiment, the compound and compositions comprising the compounds may be used to prevent the development of heartworm disease by killing immature stages of *D. immitis* that are resistant to macrocyclic lactones. In another embodiment the compounds and compositions of the description are used to treat or prevent an infection by *Dirofilaria repens* or *Dirofilaria hongkongensis*.

In another embodiment of the description, the parasite is *Haemonchus contortus, Ostertagia circumcincta, Trichostrongylus axei, Trichostrongylus colubriformis, Cooperia curticei, Nematodirus battus* and combinations thereof.

In another embodiment for treatment against both endoparasites and ectoparasites when combined with ectoparasiticidal agents, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., *Otodectes* spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In another embodiment of the description, the compounds and compositions of the description are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the description can also be used to treat other pests which include but are not limited to pests:

(1) from the order of Isopoda, for example *Oniscus asellus, Armadillidium vulgare* and *Porcellio scaber;*
(2) from the order of Diplopoda, for example *Blaniulus guttulatus;*
(3) from the order of Chilopoda, for example *Geophilus carpophagus* and *Scutigera* spp.;
(4) from the order of Symphyla, for example *Scutigerella immaculata;*
(5) from the order of Thysanura, for example *Lepisma saccharina;*
(6) from the order of Collembola, for example *Onychiurus armatus;*
(7) from the order of Blattaria, for example *Blatta orientalis, Periplaneta americana, Leucophaea maderae* and *Blattella germanica;*
(8) from the order of Hymenoptera, for example *Diprion* spp., *Hoplocampa* spp., *Lasius* spp., Monomoriumpharaonis and *Vespa* spp.;
(9) from the order of Siphonaptera, for example *Xenopsylla cheopis* and *Ceratophyllus* spp.;
(10) from the order of Anoplura (Phthiraptera), for example, *Damalinia* spp., *Haematopinus* spp., *Linognathus* spp., *Pediculus* spp., *Trichodectes* spp.;
(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Ther-*

*mesia gemmatalis,* Tinea *pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the description, the compounds and compositions of the description can be applied against a single pest or combinations thereof.

III. Mixtures with Other Active Agents

In another embodiment, the compositions comprising the cyclic depsipeptides of formula (I) may also include other veterinary therapeutic agents. Veterinary pharmaceutical agents that may be included in the compositions of the description are well-known in the art (see e.g. *Plumb' Veterinary Drug Handbook,* 5$^{th}$ Edition, ed. Donald C. Plumb, Blackwell Publishing, (2005) or The Merck Veterinary Manual, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the description, arylpyrazole compounds such as phenylpyrazoles may be included in the veterinary compositions of the description. Arylpyrazoles are known in the art and are suitable for combination with the cyclic depsipeptides of formula (I) in the compositions of the description. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the description, one or more macrocyclic lactones, which act as an acaricide, an anthelmintic agent and/or an insecticide, can be included in the compositions of the description in combination with the compound. For the avoidance of doubt, the term "macrocyclic lactone" as used herein includes both naturally occurring and synthetic or semisynthetic avermectin and milbemycin compounds.

The macrocyclic lactones that may be used in the compositions of the description include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemycin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, New Jersey (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the description comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the description provides a veterinary composition comprising an effective amount of at least one of abamectin, emamectin, eprinomectin, ivermectin, doramectin or selamectin, or a combination thereof. In still another embodiment, the veterinary compositions of the description comprise an effective amount of at least one of ivermectin, milbemectin, milbemycin oxime or moxidectin, or a combination thereof.

In another embodiment of the description, a composition comprising a compound of formula (I) in combination with a class of acaricide or insecticides known as insect growth regulators (IGRs) are provided. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225, 598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the description may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one. In another embodiment, the compositions of the description comprise a compound of formula (I) in combination with methoprene or pyriproxyfen and a pharmaceutically acceptable carrier.

In another embodiment, the compositions of the description include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl) phenylurea.

In some embodiments, the compositions of the description may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the description may include an imidazothiazole compounds including, but not limited to, tetramisole, levamisole and butamisole.

In still other embodiments, the compositions of the description may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the description may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the description including, but not limited to, arecoline in various salt forms, bunamidine, niclosamide, nitroscanate, paromomycin, paromomycin II, praziquantel and epsiprantel.

In yet other embodiments, the compositions of the description may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, an antiparasitic agent that can be included in the veterinary composition containing a compound of formula (I) can be a biologically active peptide or protein including, but not limited to, depsipeptides other than the compound. These include PF1022A or analogs thereof and emodepside. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the description may comprise an active agent from the neonicotinoid class of parasiticides. The neonicotinoids bind and inhibit insect specific nicotinic acetylcholine receptors. In one embodiment, the neonicotinoid insecticidal agent that can be combined with a compound of formula (I) in a composition of the description is imidacloprid. Agents of this class are described, for example, in U.S. Pat. No. 4,742,060 or in EP 0 892 060 (both incorporated herein by reference). In another embodiment, the compositions of the description may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the description, the cyclic depsipeptides of formula (I) can be combined with the compositions of the description is a semicarbazone, such as metaflumizone.

In another embodiment, the compositions of the description may advantageously include a mixture of one or more other isoxazoline compounds known in the art, in addition to or in place of the isoxazoline active agents described above. Isoxazoline active agents are highly effective against a variety of ectoparasites and combination with the cyclic depsipeptides of formula (I) would expand the scope of efficacy against these parasites. Particularly useful isoxazoline active agents that can be combined with the compound include afoxolaner (including substantially pure active enantiomer), sarolaner, fluralaner (including substantially pure active enantiomer) and lotilaner. These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, 9,221,835, US 2011/0144349, U.S. Pat. No. 8,053,452; US 2010/0137612, U.S. Pat. No. 8,410,153, US 2011/152081, WO 2012/089623, WO 2012/

089622, U.S. Pat. Nos. 8,119,671; 7,947,715; WO 2102/ 120135, WO 2012/107533, WO 2011/157748, US 2011/ 0245274, US 2011/0245239, US 2012/0232026, US 2012/ 0077765, US 2012/0035122, US 2012/0251247, WO 2011/ 154433, WO 2011/154434, US 2012/0238517, US 2011/ 0166193, WO 2011/104088, WO 2011/104087, WO 2011/ 104089, US 2012/015946, US 2009/0143410, WO 2007/ 123855 A2, US 2011/0118212, U.S. Pat. No. 7,951,828 & U.S. Pat. No. 7,662,972, US 2010/0137372 A1, US 2010/ 0179194 A2, US 2011/0086886 A2, US 2011/0059988 A1, US 2010/0179195 A1, US 2015/0126523, WO 2010/ 003923, WO 2010/003877, WO 2010/072602, WO 2014/ 134236, U.S. Pat. Nos. 7,897,630, and 7,951,828, all of which are incorporated herein by reference in their entirety.

In another embodiment of the description, nodulisporic acid and its derivatives may be added to the compositions of the description. These compounds are used to treat or prevent infections in humans and animals and are described, for example, in U.S. Pat. Nos. 5,399,582, 5,962,499, 6,221, 894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the description. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the description may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621 to Le Hir de Fallois, which is also incorporated herein by reference. Aryloazol-2-yl cyanoethylamino active agents, which are systemically-acting against endoparasites, may be used in combination with the compound in veterinary compositions of the description.

The compositions of the description may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the compositions of the description (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety.

In another embodiment of the description, the compositions may include a spinosyn active agent produced by the soil actinomycete Saccharopolyspora *spinosa* (see, for example Salgado V. L. and Sparks T. C., "The Spinosyns: Chemistry, Biochemistry, Mode of Action, and Resistance," in Comprehensive Molecular Insect Science, vol. 6, pp. 137-173, 2005) or a semisynthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the description. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the description, may be produced via fermentation by conventional techniques known in the art. Other spinosyn compounds that may be used in the compositions of the description are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than the compound of formula (I) described above) is included in the dosage units of the description in an amount of between about 0.1 µg and about 1000 mg. Typically, the active agent may be included in an amount of about 10 µg to about 500 mg, about 10 µg to about 400 mg, about 1 mg to about 300 mg, about 10 mg to about 200 mg or about 10 mg to about 100 mg. More typically the additional active agent will be present in an amount of about 5 mg to about 50 mg in the compositions of the description.

The concentration of the additional active agent in the compositions of the description will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the additional active agent will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the description, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the description where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 μg/kg to about 200 μg/kg or about 0.1 mg/kg to about 1 mg/kg of weight of animal.

In addition to the other active agents mentioned above, combinations of two or more active agents may be used with the compounds of the description in a composition to treat a desired spectrum of pests and parasites. It would be well within the skill level of the practitioner to decide which individual compound can be used in the inventive composition to treat a particular infection of an insect.

The description will now be further described by way of the following non-limiting examples.

EXAMPLES

The disclosure is further illustrated by the following examples, which are not to be construed as limiting this disclosure in scope or spirit to the specific procedures herein described.

It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

List of Abbreviations

ACN acetonitrile
AIBN azobisisobutyronitrile
BSA bovine serum albumin
BOC tert-butoxycarbonyl
BOP—Cl Bis(2-oxo-3-oxazolidinyl)phosphinic chloride
DCC N,N'-Dicyclohexylcarbodiimide solution
DCM dichloromethane
DEAD Diethyl azodicarboxylate
DIEA diisopropylethylamine
DMF N,N-dimethylformamide
DMAP 4-(Dimethylamino)pyridine
DMSO dimethylsulfoxide
EDAC N-(3-Dimethylaminopropyl)-N'-ethylcarbodiimide hydrochloride
ES electrospray
EtOAc or EA ethyl acetate
HATU 1-[bis(dimethylamino)methylene]-1H-1,2,3-triazolo[4,5 b]pyridinium 3-oxide hexafluorophosphate
HOBt or HOBT 1-hydroxybenzotriazole
KHMDS potassium hexamethyldisilazide, more precisely potassium bis(trimethylsilyl)amide
MeOH methanol
PE petroleum ether
TBAF tert-butyl ammonium fluoride
THF tetrahydrofuran
TLC thin-layer chromatography Example 1

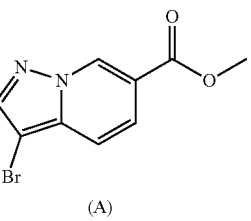 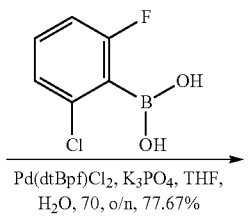

(A)

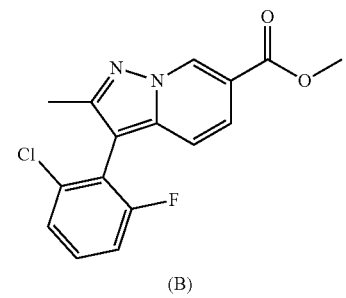

(B)

Methyl 3-(2-chloro-6-fluorophenyl)-2-methylpyrazolo[1,5-a]pyridine-6-carboxylate (B) Into a 500-mL round-bottom flask purged and maintained with an inert atmosphere of nitrogen, was placed THF (0.23 mL, 2.839 mmol, 0.15 equiv), H$_2$O (0.02 mL, 1.115 mmol, 0.06 equiv), methyl 3-bromo-2-methylpyrazolo[1,5-a]pyridine-6-carboxylate ((A) 5 g, 18.581 mmol, 1 equiv), (2-chloro-6-fluorophenyl) boronic acid (4.86 g, 27.871 mmol, 1.50 equiv), Pd(dtBpf) Cl2 (1.27 g, 1.949 mmol, 0.10 equiv), K$_3$PO$_4$ (11.8 g, 55.591 mmol, 2.99 equiv). The resulting solution was stirred overnight at 70° C. The resulting mixture was concentrated under vacuum. The residue was applied onto a silica gel column with ethyl acetate/petroleum ether (1:5). This resulted in 4.6 g (77.67%) of methyl 3-(2-chloro-6-fluorophenyl)-2-methylpyrazolo[1,5-a]pyridine-6-carboxylate as a yellow solid. (ES, m/z): 319 [M+H]+.

Example 2

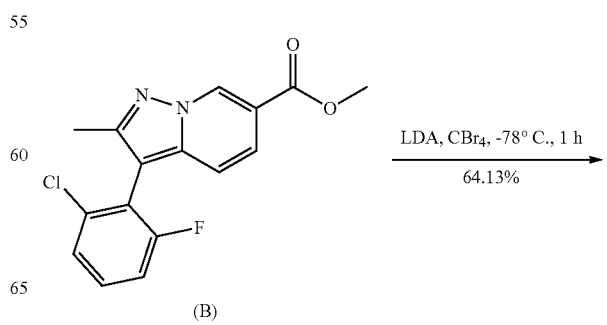

(B)

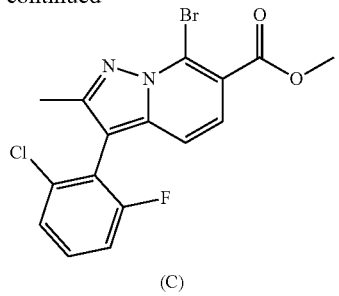

(C)

Methyl 7-bromo-3-(2-chloro-6-fluorophenyl)-2-methylpyrazolo[1,5-a]pyridine-6-carboxylate (C) Into a 250-mL 3-necked round-bottom flask purged and maintained with an inert atmosphere of nitrogen, was placed THF (30.00 mL, 416.118 mmol, 29.51 equiv), methyl 3-(2-chloro-6-fluorophenyl)-2-methylpyrazolo[1,5-a]pyridine-6-carboxylate ((B) 4 g, 12.550 mmol, 1 equiv). This was followed by the addition of LDA (7.79 mL, 15.580 mmol, 1.24 equiv) dropwise with stirring at −70° C. in 30 min. To this was added CBr$_4$ (6.24 g, 18.816 mmol, 1.50 equiv) dropwise with stirring at −70° C. The resulting solution was stirred for 1 hr at room temperature. The reaction was then quenched by the addition of NH$_4$Cl (aq.). The resulting solution was extracted with 3×20 mL of ethyl acetate. The organic phase was collected and dried over anhydrous sodium sulfate and concentrated under vacuum. The residue was applied onto a silica gel column with ethyl acetate/petroleum ether (1:3). This resulted in 3.2 g (64.13%) of methyl 7-bromo-3-(2-chloro-6-fluorophenyl)-2-methylpyrazolo[1,5-a]pyridine-6-carboxylate as a yellow solid. (ES, m/z): 397 [M+H]$^+$.

Example 3

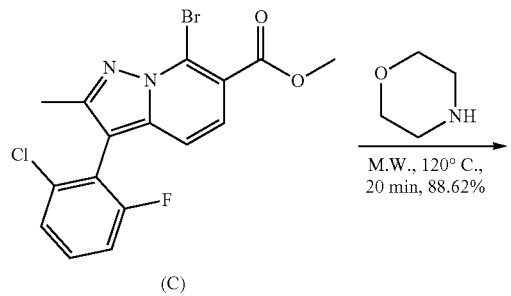

(C)

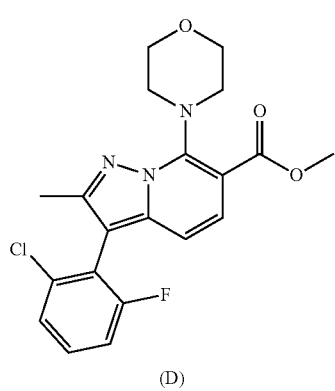

(D)

Methyl 3-(2-chloro-6-fluorophenyl)-2-methyl-7-(morpholin-4-yl)pyrazolo[1,5-a]pyridine-6-carboxylate (D) Into a 10-mL sealed tube, was placed morpholine (4 mL, 0.046 mmol, 0.04 equiv), methyl 7-bromo-3-(2-chloro-6-fluorophenyl)-2-methylpyrazolo[1,5-a]pyridine-6-carboxylate ((C) 500 mg, 1.257 mmol, 1 equiv). The final reaction mixture was irradiated with microwave radiation for 20 min at 120° C. The reaction was then quenched by the addition of water/ice. The resulting solution was extracted with 3×15 mL of ethyl acetate. The organic phase was collected and dried over anhydrous sodium sulfate and concentrated under vacuum. This resulted in 450 mg (88.62%) of methyl 3-(2-chloro-6-fluorophenyl)-2-methyl-7-(morpholin-4-yl)pyrazolo[1,5-a]pyridine-6-carboxylate as a yellow solid. (ES, m/z): 404 [M+H]$^+$.

Example 4

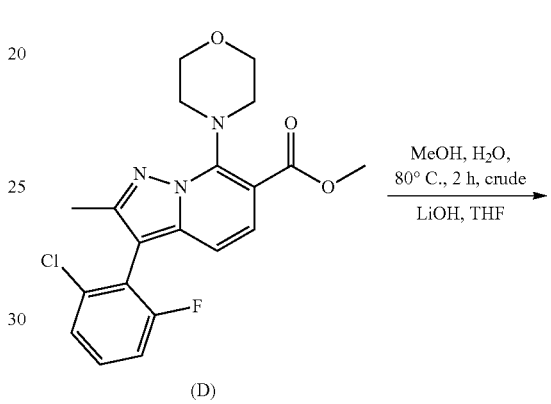

(D)

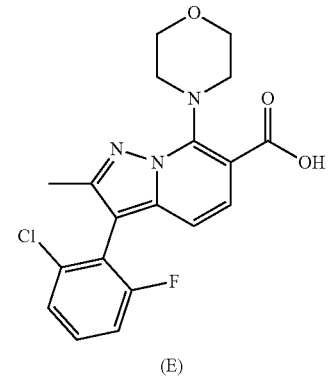

(E)

3-(2-chloro-6-fluorophenyl)-2-methyl-7-(morpholin-4-yl)pyrazolo[1,5-a]pyridine-6-carboxylic acid (E) Into a 50-mL round-bottom flask, was placed H$_2$O (1 mL, 0.056 mmol, 0.05 equiv), MeOH ((D) 5 mL, 0.156 mmol, 0.13 equiv), THF (2 mL, 0.028 mmol, 0.02 equiv), methyl 3-(2-chloro-6-fluorophenyl)-2-methyl-7-(morpholin-4-yl)pyrazolo[1,5-a]pyridine-6-carboxylate (480 mg, 1.189 mmol, 1 equiv), LiOH (143 mg, 5.971 mmol, 5.02 equiv). The resulting solution was stirred for 2 hr at 80° C. The reaction was then quenched by the addition of 10 mL of water. The pH value of the solution was adjusted to 4 with HCl (3 M). The resulting solution was extracted with 3×20 mL of ethyl acetate. The organic phase was collected and dried over anhydrous sodium sulfate and concentrated under vacuum. This resulted in 400 mg (crude) of 3-(2-chloro-6-fluorophenyl)-2-methyl-7-(morpholin-4-yl)pyrazolo[1,5-a]pyridine-6-carboxylic acid as a yellow solid. (ES, m/z): 390 [M+H]$^+$.

1H), 6.88 (d, J=8.4 Hz, 1H), 5.29-5.25 (m, 1H), 4.37-4.22 (m, 2H), 3.67-3.57 (m, 8H), 2.36 (s, 3H), 2.32-2.24 (m, 2H).

Example 5

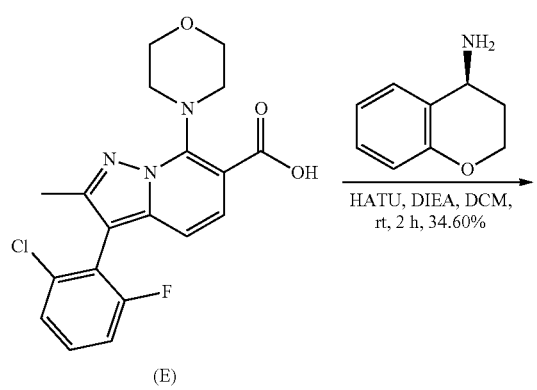

(E)

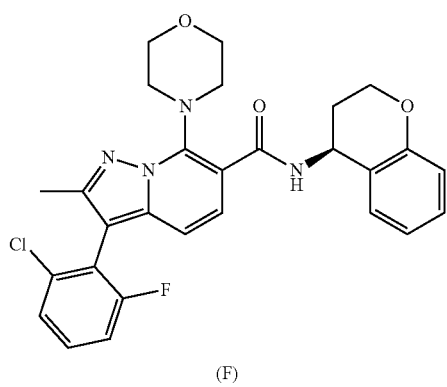

(F)

3-(2-chloro-6-fluorophenyl)-N-[(4S)-3,4-dihydro-2H-1-benzopyran-4-yl]-2-methyl-7-(morpholin-4-yl)pyrazolo[1,5-a]pyridine-6-carboxamide (F) Into a 50-mL round-bottom flask, was placed DCM (5 mL, 0.059 mmol, 0.06 equiv), 3-(2-chloro-6-fluorophenyl)-2-methyl-7-(morpholin-4-yl)pyrazolo[1,5-a]pyridine-6-carboxylic acid (400 mg, 1.026 mmol, 1 equiv), (4S)-3,4-dihydro-2H-1-benzopyran-4-amine (225 mg, 1.508 mmol, 1.47 equiv), HATU (782.8 mg, 2.059 mmol, 2.01 equiv), DIEA (398.6 mg, 3.084 mmol, 3.01 equiv). The resulting solution was stirred for 1 hr at room temperature. The resulting mixture was concentrated under vacuum. The crude product was purified by Flash-Prep-HPLC with the following conditions (IntelFlash-1): Column, C18 silica gel; mobile phase, H₂O:CH₃CN=70:30 increasing to H₂O:CH₃CN=15:85 within 25 min; Detector, UV 254 nm. This resulted in 185 mg (34.60%) of 3-(2-chloro-6-fluorophenyl)-N-[(4S)-3,4-dihydro-2H-1-benzopyran-4-yl]-2-methyl-7-(morpholin-4-yl)pyrazolo[1,5-a]pyridine-6-carboxamide as a yellow solid, (ES, m/z): 521 [M+H]⁺; ¹H NMR (300 MHz, CD₃OD, ppm): δ 7.67 (d, J=9.3 Hz, 1H), 7.47-7.43 (m, 2H), 7.35 (d, J=7.5 Hz, 2H), 7.27-7.21 (m, 2H), 7.07 (d, J=9.3 Hz, 1H), 6.98-6.93 (m,

Example 6

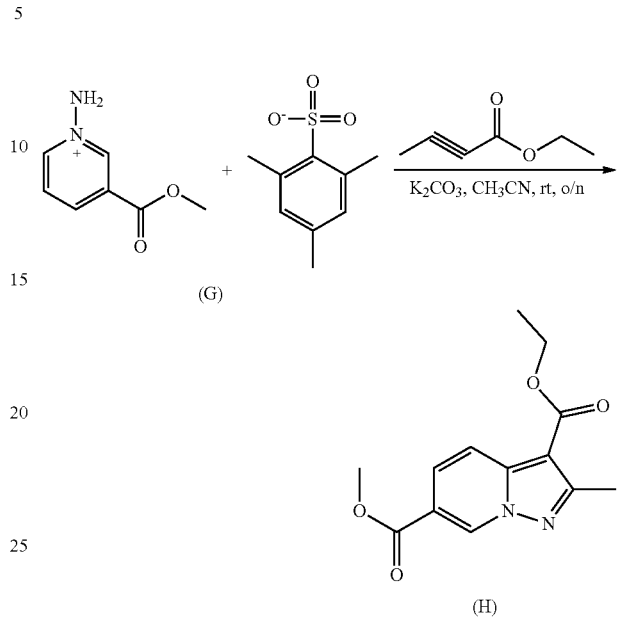

(G)

(H)

3-ethyl 6-methyl 2-methylpyrazolo[1,5-a]pyridine-3,6-dicarboxylate (H) Into a 500-mL 3-necked round-bottom flask, was placed 1-amino-3-(methoxycarbonyl)pyridin-1-ium 2,4,6-trimethylbenzene-1-sulfonate ((G) 90 g, 255.384 mmol, 1 equiv), CH₃CN (200 mL), K₂CO₃ (105.89 g, 766.178 mmol, 3.00 equiv), ethyl but-2-ynoate (42.95 g, 383.077 mmol, 1.5 equiv). The resulting solution was stirred overnight at room temperature. The resulting mixture was concentrated. The residue was applied onto a silica gel column with ethyl acetate/petroleum ether (1:10). This resulted in 19 g (28.37%) of 3-ethyl 6-methyl 2-methylpyrazolo[1,5-a]pyridine-3,6-dicarboxylate as a yellow solid. (ES, m/z): 263 [M+H]⁺.

Example 7

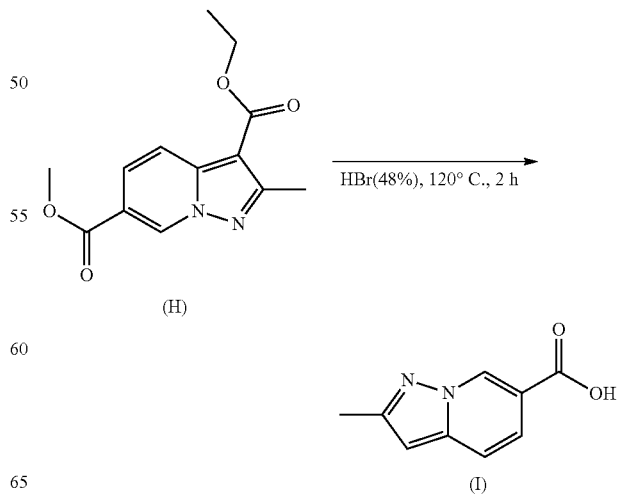

Methyl 2-methylpyrazolo[1,5-a]pyridine-6-carboxylate (I) Into a 1-L round-bottom flask, was placed 3-ethyl 6-methyl 2-methylpyrazolo[1,5-a]pyridine-3,6-dicarboxylate ((H) 34 g, 129.640 mmol, 1 equiv), HBr (300 mL, 48%). The resulting solution was stirred for 2 hr at 120° C. in an oil bath. The resulting mixture was concentrated. This resulted in 30 g (crude) of methyl 2-methylpyrazolo[1,5-a]pyridine-6-carboxylate as a yellow solid. (ES, m/z): 177 [M+H]+.

Example 8

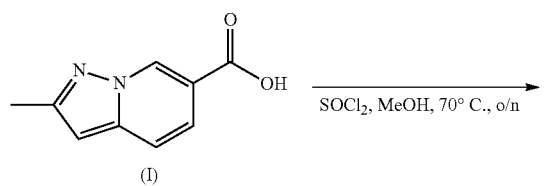

(I)

Methyl 2-methylpyrazolo[1,5-a]pyridine-6-carboxylate (J) Into a 1-L round-bottom flask purged and maintained with an inert atmosphere of nitrogen, was placed 2-methylpyrazolo[1,5-a]pyridine-6-carboxylic acid (30 g, 170.285 mmol, 1 equiv), MeOH (100 mL). This was followed by the addition of SOCl$_2$ (40 g, 551.400 mmol, 3.24 equiv) dropwise with stirring at 0° C. The resulting solution was stirred overnight at 70° C. in an oil bath. The resulting mixture was concentrated. The pH value of the solution was adjusted to 8 with NaHCO$_3$ (50%). The resulting solution was extracted with 3×100 mL of ethyl acetate. The collected organic layer was washed with 3×50 ml of NaCl and concentrated. This resulted in 21 g (crude) of Methyl 2-methylpyrazolo[1,5-a]pyridine-6-carboxylate as a yellow solid. (ES, m/z): 191 [M+H]+.

Example 9

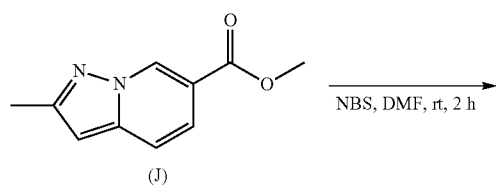

(J)

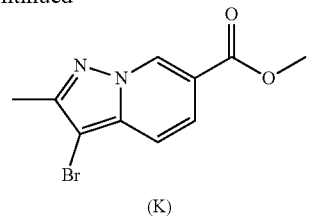

(K)

Methyl 3-bromo-2-methylpyrazolo[1,5-a]pyridine-6-carboxylate (K) Into a 500-mL round-bottom flask, was placed methyl 2-methylpyrazolo[1,5-a]pyridine-6-carboxylate ((J) 21 g, 110.409 mmol, 1 equiv), DMF (100 mL), NBS (21.62 g, 121.472 mmol, 1.10 equiv). The resulting solution was stirred for 2 hr at room temperature. The reaction was then quenched by the addition of 300 mL of water. The resulting solution was extracted with 3×100 mL of ethyl acetate. The organic layer was collected and washed with 3×100 ml of NaCl. The collected organic layer was dried over anhydrous sodium sulfate and concentrated. The residue was applied onto a silica gel column with ethyl acetate/petroleum ether (1:5). This resulted in 27 g (90.88%) of methyl 3-bromo-2-methylpyrazolo[1,5-a]pyridine-6-carboxylate as a white solid. (ES, m/z): 269 [M+H]+.

Example 10

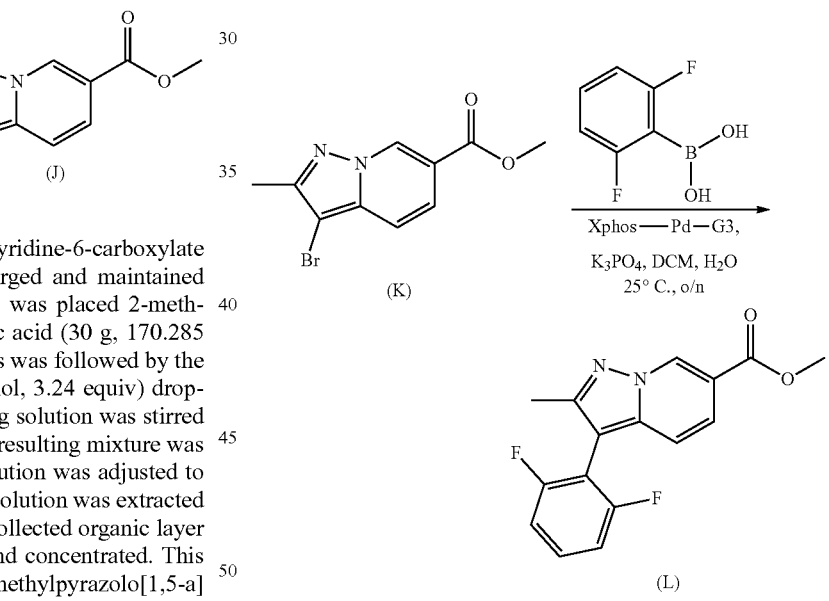

(L)

Methyl 3-(2,6-difluorophenyl)-2-methylpyrazolo[1,5-a]pyridine-6-carboxylate (L) Into a 500-mL vial purged and maintained with an inert atmosphere of nitrogen, was placed methyl 3-bromo-2-methylpyrazolo[1,5-a]pyridine-6-carboxylate ((K) 8 g, 0.03 mol, 1 equiv), DCM (160 mL), (2,6-difluorophenyl)boronic acid (7.04 g, 0.045 mol, 1.50 equiv), H$_2$O (80 mL), K$_3$PO$_4$ (18.9 g, 0.090 mol, 3.00 equiv), Xphos-Pd-G$_3$ (2.56 g, 0.32 mmol, 0.1 equiv). The resulting solution was stirred for 2 hr at 25° C. The resulting solution was stirred overnight at 70° C. The resulting mixture was concentrated under vacuum. The residue was applied onto a silica gel column with ethyl acetate/petroleum ether (1:5). This resulted in 4.2 g (47%) of Methyl 3-(2,6-difluorophenyl)-2-methylpyrazolo[1,5-a]pyridine-6-carboxylate as a yellow solid. (ES, m/z): 303 [M+H]$^+$

Example 11

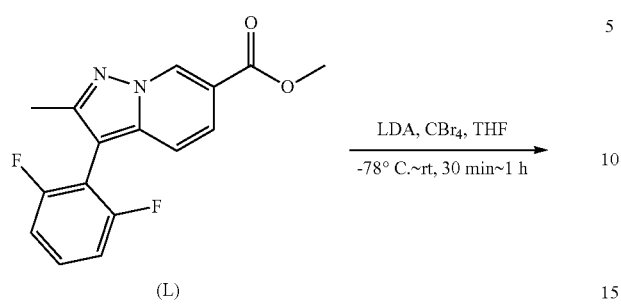

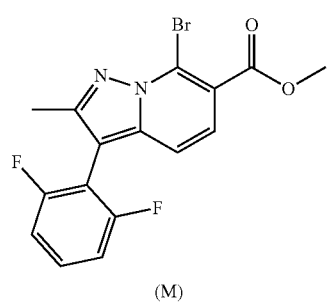

Methyl 7-bromo-3-(2,6-difluorophenyl)-2-methylpyrazolo[1,5-a]pyridine-6-carboxylate (M) Into a 100-mL 3-necked round-bottom flask purged and maintained with an inert atmosphere of nitrogen, was placed methyl 3-(2,6-difluorophenyl)-2-methylpyrazolo[1,5-a]pyridine-6-carboxylate ((L) 4.1 g, 13.564 mmol, 1 equiv), THF (41 mL), LDA (1.60 g, 0.015 mmol, 1.1 equiv) at −78° C. and stirred for 30 min. To the above was added $CBr_4$ (6.75 g, 0.020 mmol, 1.5 equiv). The reaction was stirred for an additional 1 hr at room temperature. The reaction was then quenched by the addition of water. The resulting solution was extracted with 300 ml of ethyl acetate. The organic phase was collected and concentrated under vacuum. The residue was applied onto a silica gel column with ethyl acetate/hexane (1/10). This resulted in 1.4 g (87.04%) of methyl 7-bromo-3-(2,6-difluorophenyl)-2-methylpyrazolo[1,5-a]pyridine-6-carboxylate as a yellow solid. (ES, m/z): 381 [M+H]$^+$.

Methyl 3-(2,6-difluorophenyl)-2-methyl-7-(prop-1-en-2-yl)pyrazolo[1,5-a]pyridine-6-carboxylate (N) Into a 100-mL 3-necked round-bottom purged and maintained with an inert atmosphere of nitrogen, was placed methyl 7-bromo-3-(2,6-difluorophenyl)-2-methylpyrazolo[1,5-a]pyridine-6-carboxylate ((M) 1000 mg, 2.623 mmol, 1 equiv), dioxane (10 mL), $H_2O$ (1 mL), 4,4,5,5-tetramethyl-2-(prop-1-en-2-yl)-1,3,2-dioxaborolane (1322.54 mg, 7.870 mmol, 3.00 equiv), $Pd(PPh_3)_4$ (303.16 mg, 0.262 mmol, 0.1 equiv), $K_3PO_4$ (1670.61 mg, 7.870 mmol, 3.0 equiv). The resulting solution was stirred for 1 hr at 100° C. The reaction mixture was cooled to room temperature and quenched by 10 mL of water. The resulting solution was extracted with 30 mL of ethyl acetate. The organic layer was collected and dried over anhydrous sodium sulfate and concentrated under vacuum. The residue was applied onto a silica gel column with ethyl acetate/hexane (1/15). This resulted in 805 mg (89.63%) of methyl 3-(2,6-difluorophenyl)-2-methyl-7-(prop-1-en-2-yl)pyrazolo[1,5-a]pyridine-6-carboxylate as a yellow solid. (ES, m/z): 343 [M+H]$^+$.

Example 13

Example 12

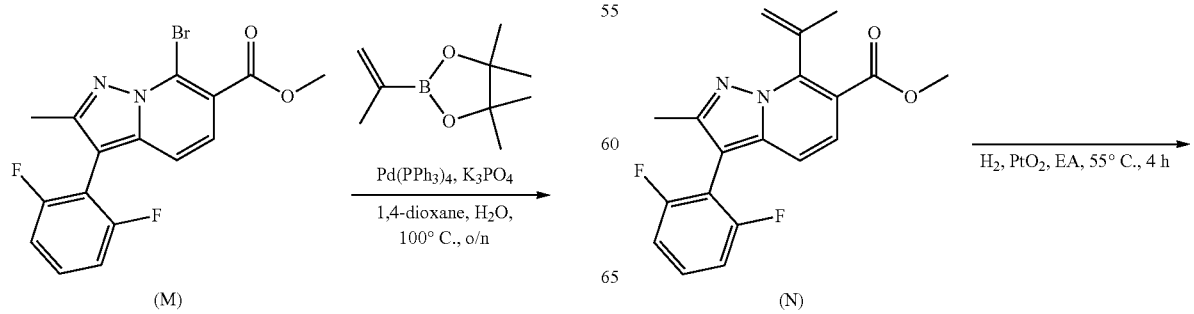

-continued

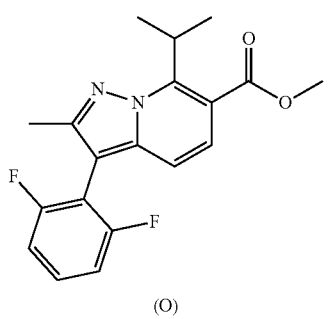

(O)

Methyl 3-(2,6-difluorophenyl)-2-methyl-7-(propan-2-yl)pyrazolo[1,5-a]pyridine-6-carboxylate (O) Into a 100-mL 3-necked round-bottom flask purged and maintained with an atmosphere of nitrogen, was placed methyl 3-(2,6-difluorophenyl)-2-methyl-7-(prop-1-en-2-yl)pyrazolo[1,5-a]pyridine-6-carboxylate ((N) 805 mg, 2.351 mmol, 1 equiv), EA (16 mL), PtO$_2$ (240.29 mg, 1.058 mmol, 0.45 equiv), then H$_2$(g) was introduced. The resulting solution was stirred for 4 hr at 55° C. The solid was filtered out. The filtrate was concentrated under vacuum. This resulted in 657 mg (81.14%) of methyl 3-(2,6-difluorophenyl)-2-methyl-7-(propan-2-yl)pyrazolo[1,5-a]pyridine-6-carboxylate as a solid. (ES, m/z): 345 [M+H]$^+$.

Example 14

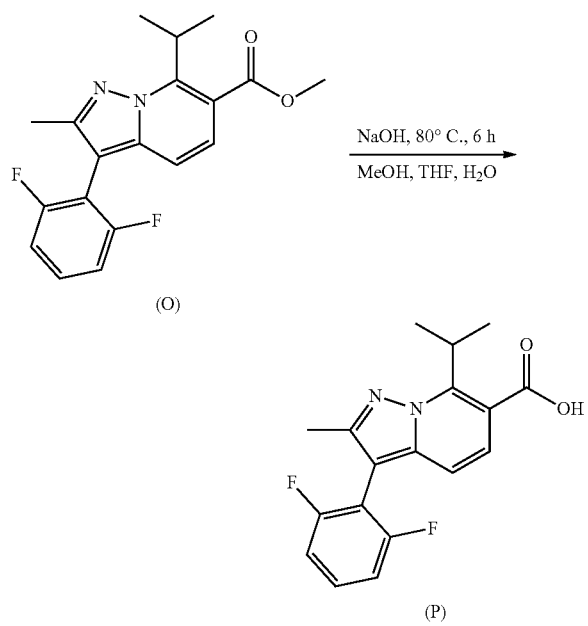

3-(2,6-difluorophenyl)-2-methyl-7-(propan-2-yl)pyrazolo[1,5-a]pyridine-6-carboxylic acid (O) Into a 50-mL 3-necked round-bottom flask, was placed methyl 3-(2,6-difluorophenyl)-2-methyl-7-(propan-2-yl)pyrazolo[1,5-a]pyridine-6-carboxylate ((P) 650 mg, 1.888 mmol, 1 equiv), MeOH (8 mL), THF (8 mL), H$_2$O (2.5 mL), NaOH (377.48 mg, 9.438 mmol, 5.00 equiv). The resulting solution was stirred for 6 hr at 80° C. The residue was diluted with water. The mixture was adjusted to pH 4 with HCl (1 M). The resulting solution was extracted with 3×20 mL of ethyl acetate. The organic layer was collected and dried over anhydrous sodium sulfate and concentrated under vacuum. This resulted in 617 mg (98.95%) of 3-(2,6-difluorophenyl)-2-methyl-7-(propan-2-yl)pyrazolo[1,5-a]pyridine-6-carboxylic acid as a yellow solid. (ES, m/z): 331 [M+H]+.

Example 15

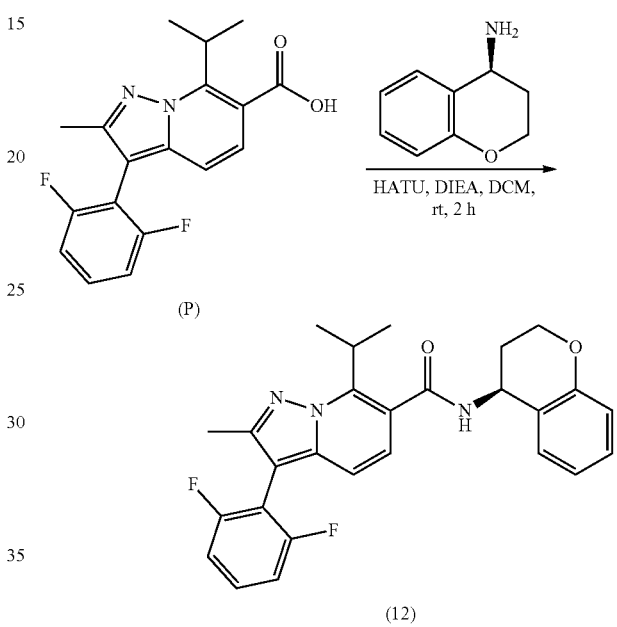

3-(2,6-difluorophenyl)-N-[(4S)-3,4-dihydro-2H-1-benzopyran-4-yl]-2-methyl-7-(propan-2-yl)pyrazolo[1,5-a]pyridine-6-carboxamide (Q) Into a 40-mL vial, was placed 3-(2,6-difluorophenyl)-2-methyl-7-(propan-2-yl)pyrazolo[1,5-a]pyridine-6-carboxylic acid ((P) 325 mg, 0.984 mmol, 1 equiv), DCM (10 mL), (4S)-3,4-dihydro-2H-1-benzopyran-4-amine (220.18 mg, 1.476 mmol, 1.50 equiv), HATU (748.18 mg, 1.968 mmol, 2.0 equiv), DIEA (381.47 mg, 2.952 mmol, 3.0 equiv). The resulting solution was stirred for 2 hr at room temperature. The resulting mixture was concentrated under vacuum. The crude product was purified by Flash-Prep-HPLC with the following conditions (IntelFlash-1): Column, C18 silica gel; mobile phase, H$_2$O:CH$_3$CN=60:40 increasing to H$_2$O:CH$_3$CN=15:85 within 25 min; Detector, UV 254 nm. This resulted in 180 mg (39.64%) of 3-(2,6-difluorophenyl)-N-[(4S)-3,4-dihydro-2H-1-benzopyran-4-yl]-2-methyl-7-(propan-2-yl)pyrazolo[1,5-a]pyridine-6-carboxamide as a white solid. (ES, m/z): 462 [M+H]+; $^1$H NMR (300 MHz, CDCl$_3$, ppm): δ 7.38-7.14 (m, 4H), 7.10-6.94 (m, 4H), 6.88 (d, J=8.4 Hz, 1H), 5.72 (d, J=7.8 Hz, 1H), 5.38-5.36 (m, 1H), 4.37-4.34 (m, 1H), 4.25-4.09 (m, 2H), 2.45 (s, 3H), 2.43-2.36 (m, 1H), 2.27-2.24 (m, 1H), 1.69 (d, J=6.3 Hz, 3H), 1.67 (d, J=6.3 Hz, 3H).

Although the foregoing subject matter has been described in some detail by way of illustration and example for purposes of clarity of understanding, it will be understood by those skilled in the art that certain changes and modifications can be practiced within the scope of the description and Examples. In this manner, Table 1 includes compounds prepared according to the description

TABLE 1

| Structure | Compound # |
|---|---|
| 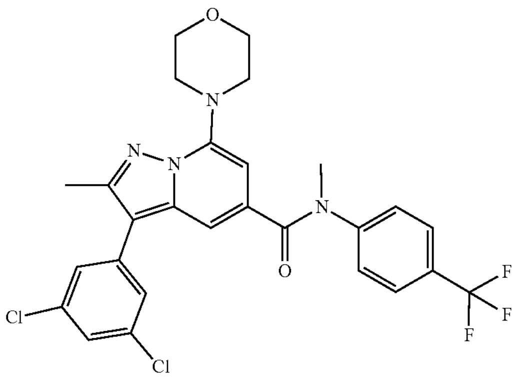 [SMILES: Cc1nn2c(N3CCOCC3)cc(C(=O)N(C)c3ccc(C(F)(F)F)cc3)cc2c1-c1cc(Cl)cc(Cl)c1] | 1 |
| 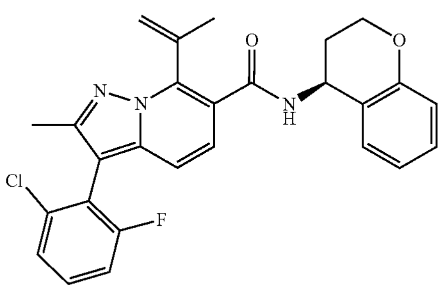 [SMILES: C=C(C)c1c(C(=O)N[C@H]2CCOc3ccccc32)ccc2c(-c3c(F)cccc3Cl)c(C)nn12] | 2 |
| 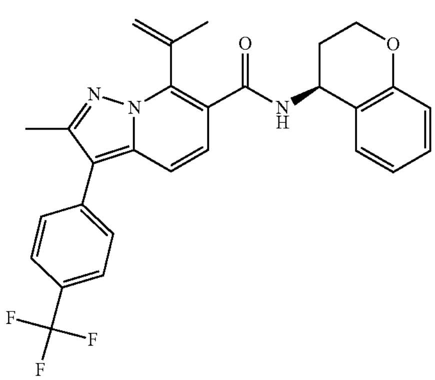 [SMILES: C=C(C)c1c(C(=O)N[C@H]2CCOc3ccccc32)ccc2c(-c3ccc(C(F)(F)F)cc3)c(C)nn12] | 3 |
| 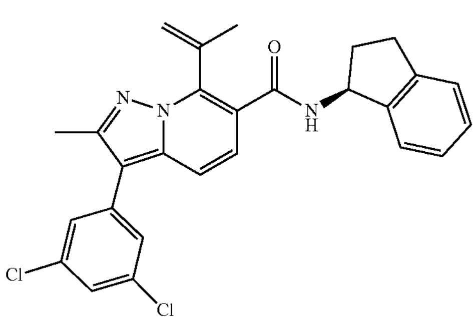 [SMILES: C=C(C)c1c(C(=O)N[C@H]2CCc3ccccc32)ccc2c(-c3cc(Cl)cc(Cl)c3)c(C)nn12] | 4 |

TABLE 1-continued

| Structure | Compound # |
|---|---|
| 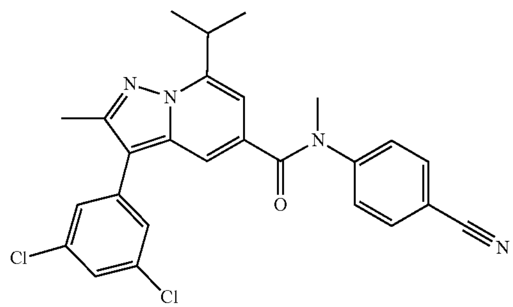 [SMILES: Cc1nn2c(C(C)C)cc(C(=O)N(C)c3ccc(C#N)cc3)cc2c1-c1cc(Cl)cc(Cl)c1] | 5 |
| 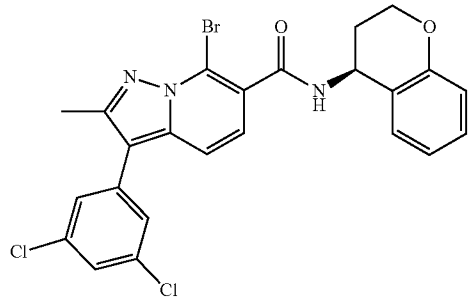 [SMILES: Cc1nn2c(Br)c(C(=O)N[C@H]3CCOc4ccccc43)ccc2c1-c1cc(Cl)cc(Cl)c1] | 6 |
| 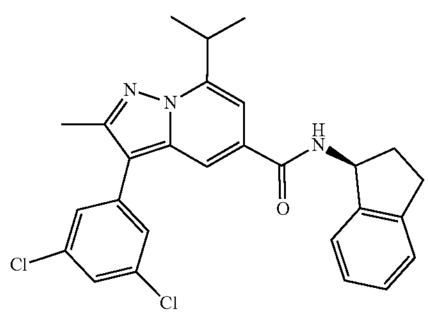 [SMILES: Cc1nn2c(C(C)C)cc(C(=O)N[C@H]3CCc4ccccc43)cc2c1-c1cc(Cl)cc(Cl)c1] | 7 |
| 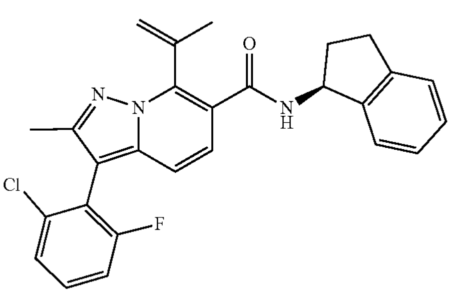 [SMILES: C=C(C)c1c(C(=O)N[C@H]2CCc3ccccc32)ccc2c(-c3c(F)cccc3Cl)c(C)nn12] | 8 |
| 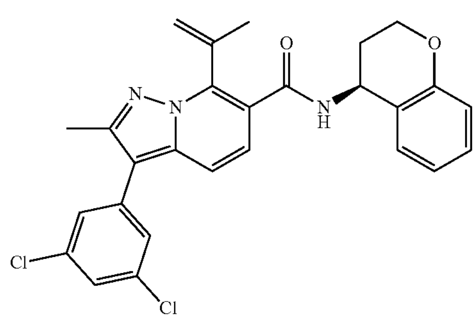 [SMILES: C=C(C)c1c(C(=O)N[C@H]2CCOc3ccccc32)ccc2c(-c3cc(Cl)cc(Cl)c3)c(C)nn12] | 9 |

TABLE 1-continued

| Structure | Compound # |
|---|---|
| 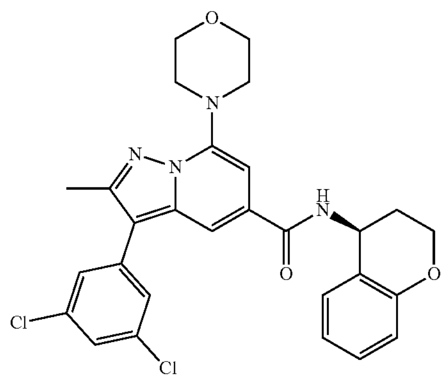 [SMILES: Cc1nn2c(N3CCOCC3)cc(C(=O)N[C@H]3CCOc4ccccc43)cc2c1-c1cc(Cl)cc(Cl)c1] | 10 |
| 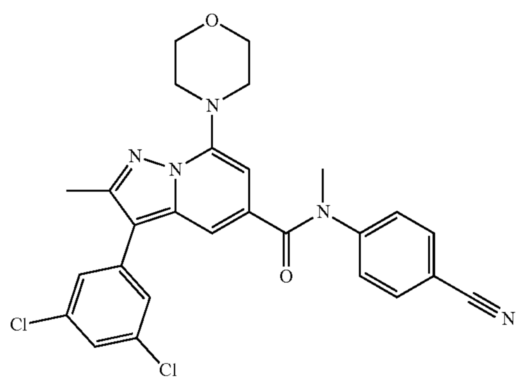 [SMILES: Cc1nn2c(N3CCOCC3)cc(C(=O)N(C)c3ccc(C#N)cc3)cc2c1-c1cc(Cl)cc(Cl)c1] | 11 |
| 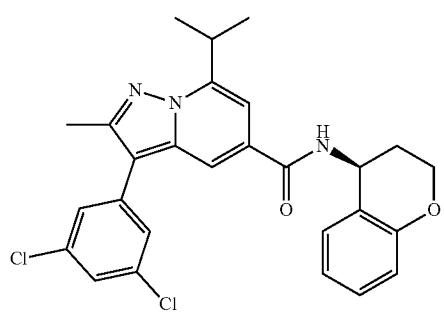 [SMILES: Cc1nn2c(C(C)C)cc(C(=O)N[C@H]3CCOc4ccccc43)cc2c1-c1cc(Cl)cc(Cl)c1] | 12 |
| 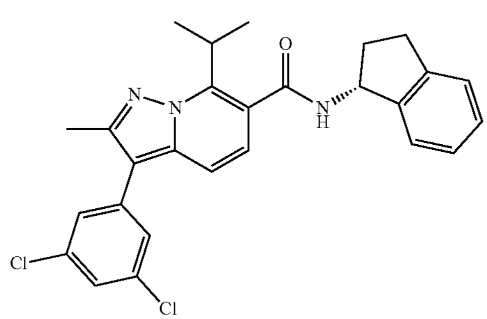 [SMILES: Cc1nn2c(C(C)C)c(C(=O)N[C@@H]3CCc4ccccc43)ccc2c1-c1cc(Cl)cc(Cl)c1] | 13 |

TABLE 1-continued

| Structure | Compound # |
| --- | --- |
| 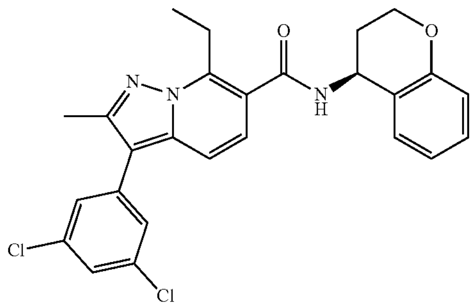 [SMILES: CCc1c(C(=O)N[C@H]2CCOc3ccccc32)ccc2c(-c3cc(Cl)cc(Cl)c3)c(C)nn12] | 14 |
| 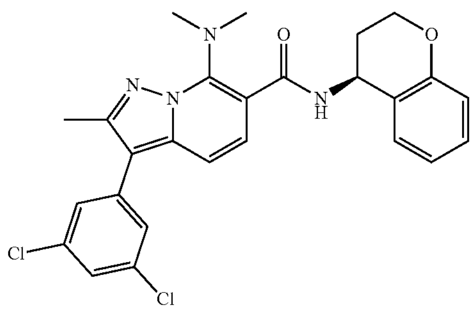 [SMILES: Cc1nn2c(N(C)C)c(C(=O)N[C@H]3CCOc4ccccc43)ccc2c1-c1cc(Cl)cc(Cl)c1] | 15 |
| 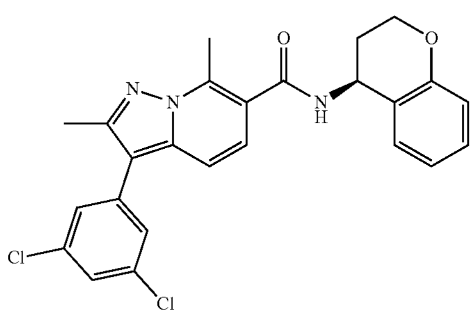 [SMILES: Cc1nn2c(C)c(C(=O)N[C@H]3CCOc4ccccc43)ccc2c1-c1cc(Cl)cc(Cl)c1] | 16 |
| 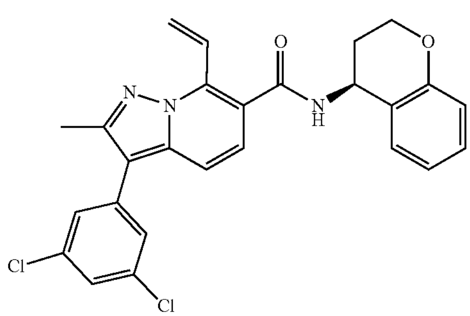 | 17 |
| 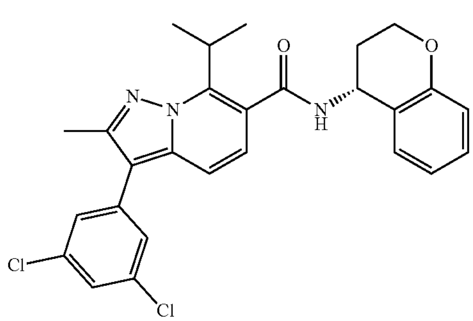 [SMILES: Cc1nn2c(C(C)C)c(C(=O)N[C@@H]3CCOc4ccccc43)ccc2c1-c1cc(Cl)cc(Cl)c1] | 18 |

TABLE 1-continued

| Structure | Compound # |
|---|---|
| 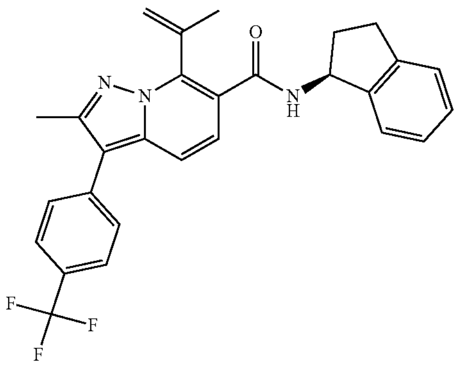 [SMILES: C=C(C)c1c(C(=O)N[C@H]2CCc3ccccc32)ccc2c(-c3ccc(C(F)(F)F)cc3)c(C)nn12] | 19 |
| 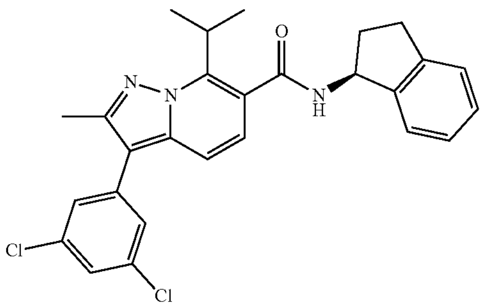 [SMILES: Cc1nn2c(C(C)C)c(C(=O)N[C@H]3CCc4ccccc43)ccc2c1-c1cc(Cl)cc(Cl)c1] | 20 |
| 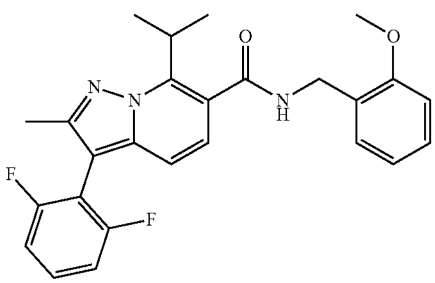 [SMILES: COc1ccccc1CNC(=O)c1ccc2c(-c3c(F)cccc3F)c(C)nn2c1C(C)C] | 21 |
| 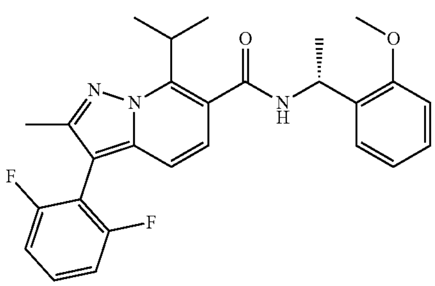 [SMILES: COc1ccccc1[C@@H](C)NC(=O)c1ccc2c(-c3c(F)cccc3F)c(C)nn2c1C(C)C] | 22 |
| 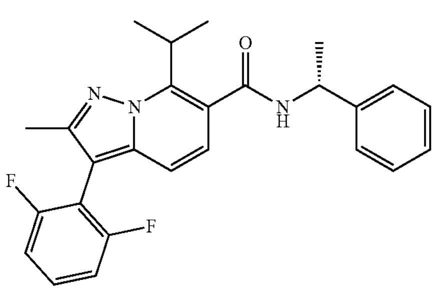 [SMILES: Cc1nn2c(C(C)C)c(C(=O)N[C@H](C)c3ccccc3)ccc2c1-c1c(F)cccc1F] | 23 |

TABLE 1-continued

| Structure | Compound # |
|---|---|
| 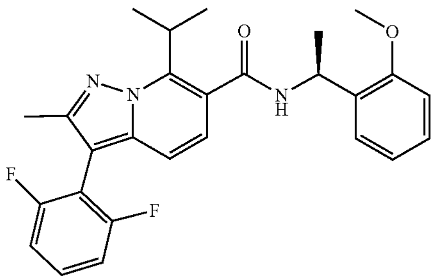 [SMILES: COc1ccccc1[C@H](C)NC(=O)c1ccc2c(-c3c(F)cccc3F)c(C)nn2c1C(C)C] | 24 |
| 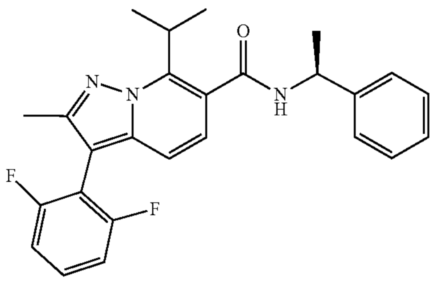 [SMILES: Cc1nn2c(C(C)C)c(C(=O)N[C@@H](C)c3ccccc3)ccc2c1-c1c(F)cccc1F] | 25 |
| 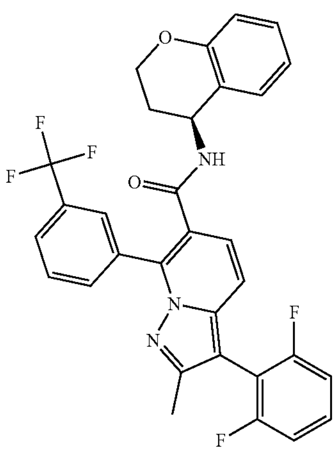 [SMILES: Cc1nn2c(-c3cccc(C(F)(F)F)c3)c(C(=O)N[C@H]3CCOc4ccccc43)ccc2c1-c1c(F)cccc1F] | 26 |
| 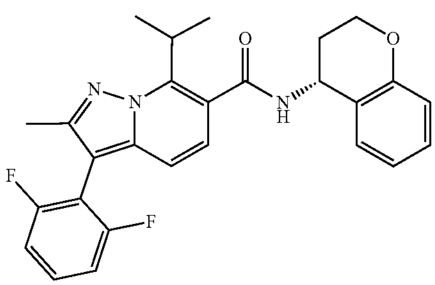 [SMILES: Cc1nn2c(C(C)C)c(C(=O)N[C@@H]3CCOc4ccccc43)ccc2c1-c1c(F)cccc1F] | 27 |
| 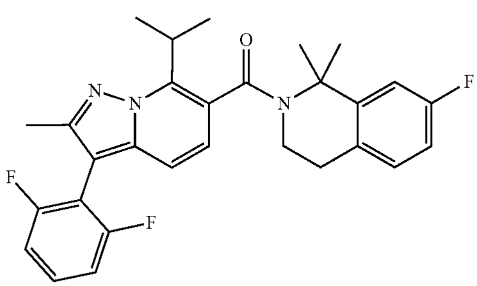 [SMILES: Cc1nn2c(C(C)C)c(C(=O)N3CCc4ccc(F)cc4C3(C)C)ccc2c1-c1c(F)cccc1F] | 28 |

TABLE 1-continued

| Structure | Compound # |
|---|---|
| 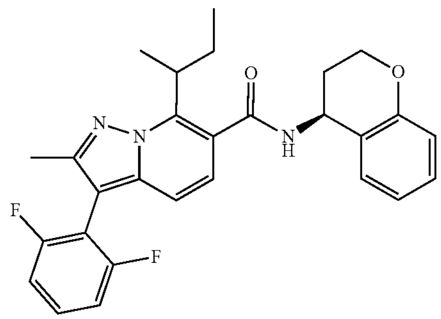 [SMILES: CCC(C)c1c(C(=O)N[C@H]2CCOc3ccccc32)ccc2c(-c3c(F)cccc3F)c(C)nn12] | 29 |
| 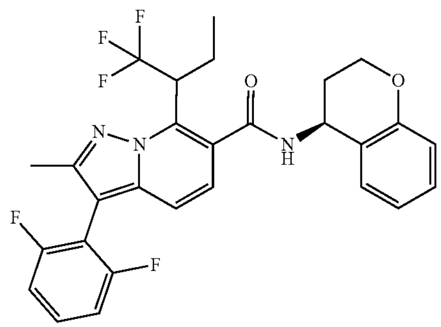 [SMILES: CCC(c1c(C(=O)N[C@H]2CCOc3ccccc32)ccc2c(-c3c(F)cccc3F)c(C)nn12)C(F)(F)F] | 30 |
| 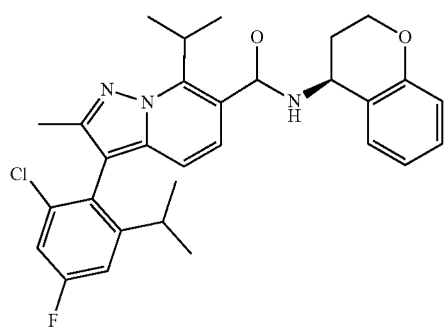 [SMILES: Cc1nn2c(C(C)C)c(COCN[C@H]3CCOc4ccccc43)ccc2c1-c1c(Cl)cc(F)cc1C(C)C] | 31 |
| 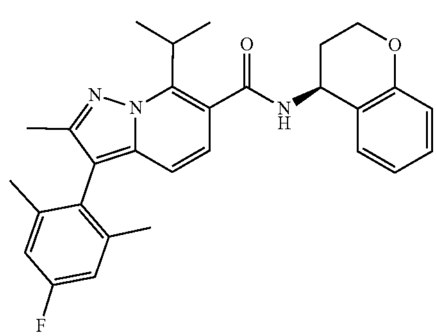 [SMILES: Cc1cc(F)cc(C)c1-c1c(C)nn2c(C(C)C)c(C(=O)N[C@H]3CCOc4ccccc43)ccc12] | 32 |

TABLE 1-continued

| Structure | Compound # |
|---|---|
| 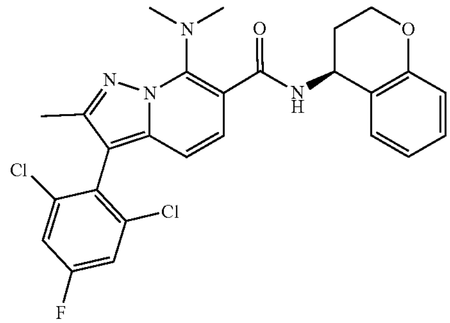 [SMILES: Cc1nn2c(N(C)C)c(C(=O)N[C@H]3CCOc4ccccc43)ccc2c1-c1c(Cl)cc(F)cc1Cl] | 33 |
| 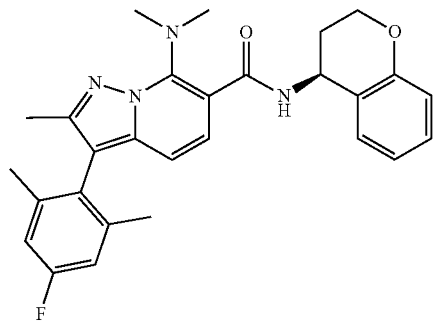 [SMILES: Cc1cc(F)cc(C)c1-c1c(C)nn2c(N(C)C)c(C(=O)N[C@H]3CCOc4ccccc43)ccc12] | 34 |
| 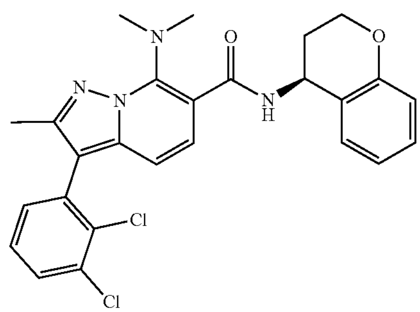 [SMILES: Cc1nn2c(N(C)C)c(C(=O)N[C@H]3CCOc4ccccc43)ccc2c1-c1cccc(Cl)c1Cl] | 35 |
| 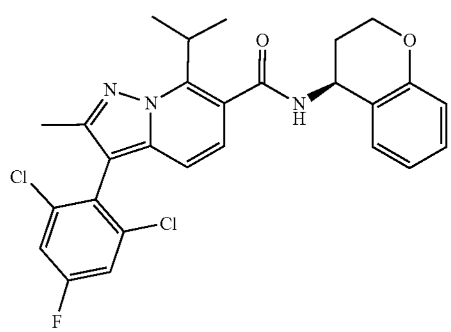 [SMILES: Cc1nn2c(C(C)C)c(C(=O)N[C@H]3CCOc4ccccc43)ccc2c1-c1c(Cl)cc(F)cc1Cl] | 36 |
| 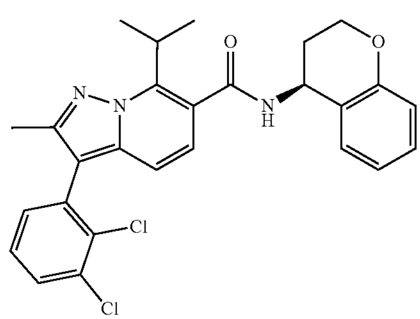 [SMILES: Cc1nn2c(C(C)C)c(C(=O)N[C@H]3CCOc4ccccc43)ccc2c1-c1cccc(Cl)c1Cl] | 37 |

TABLE 1-continued

| Structure | Compound # |
|---|---|
| 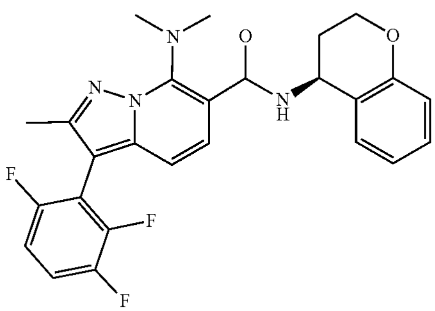 [SMILES: Cc1nn2c(N(C)C)c(COCN[C@H]3CCOc4ccccc43)ccc2c1-c1c(F)ccc(F)c1F] | 38 |
| 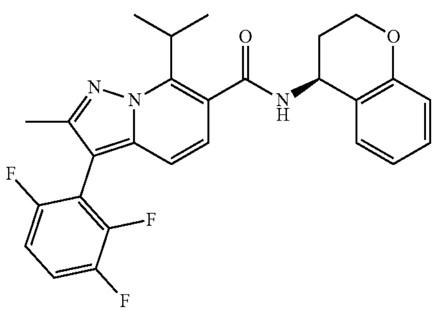 [SMILES: Cc1nn2c(C(C)C)c(C(=O)N[C@H]3CCOc4ccccc43)ccc2c1-c1c(F)ccc(F)c1F] | 39 |
| 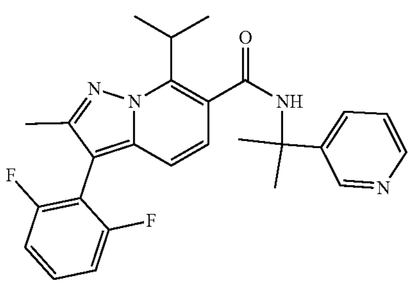 [SMILES: Cc1nn2c(C(C)C)c(C(=O)NC(C)(C)c3cccnc3)ccc2c1-c1c(F)cccc1F] | 40 |
| 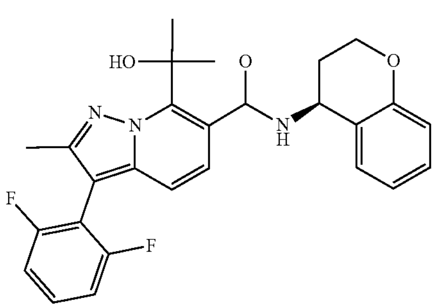 [SMILES: Cc1nn2c(C(C)(C)O)c(COCN[C@H]3CCOc4ccccc43)ccc2c1-c1c(F)cccc1F] | 41 |
| 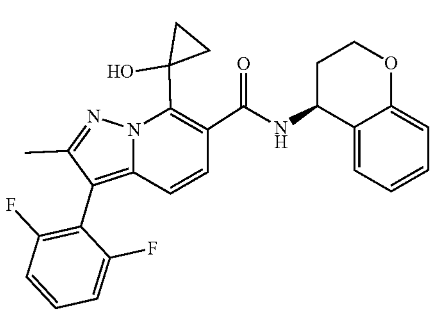 | 42 |

TABLE 1-continued
| Structure | Compound # |
|---|---|
| 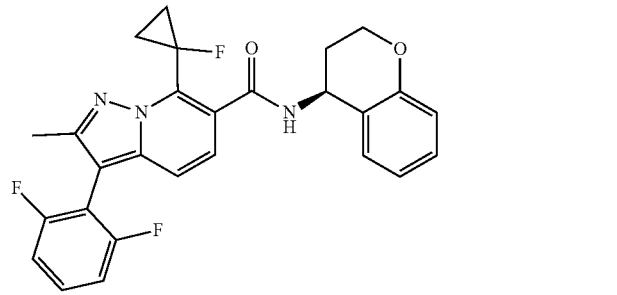 [SMILES: Cc1nn2c(C3(F)CC3)c(C(=O)N[C@H]3CCOc4ccccc43)ccc2c1-c1c(F)cccc1F] | 43 |
| 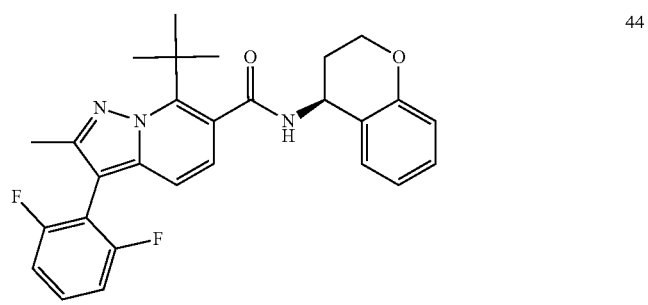 | 44 |
| 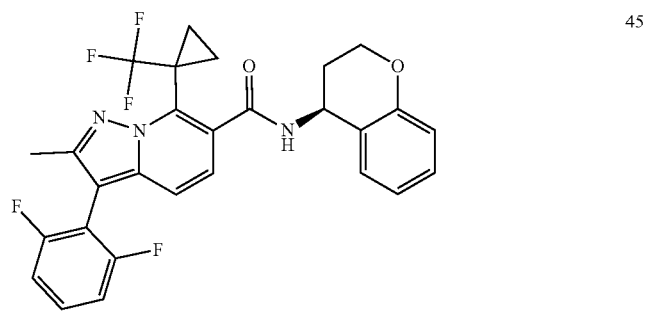 | 45 |
| 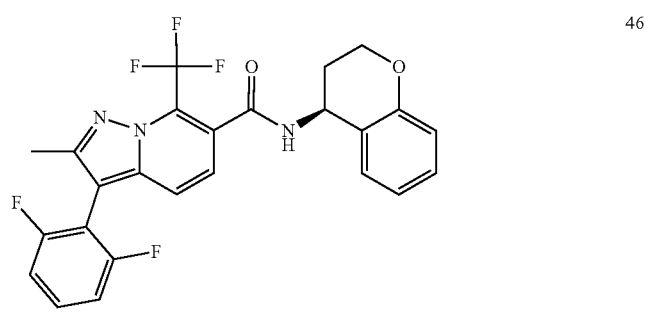 | 46 |
| 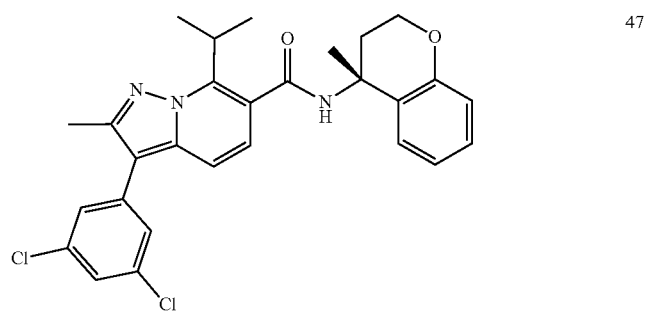 | 47 |

TABLE 1-continued
| Structure | Compound # |
|---|---|
| 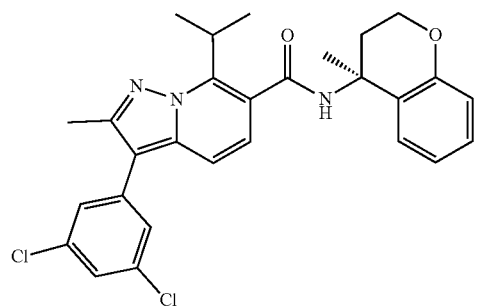 [SMILES: Cc1nn2c(C(C)C)c(C(=O)N[C@@]3(C)CCOc4ccccc43)ccc2c1-c1cc(Cl)cc(Cl)c1] | 48 |
| 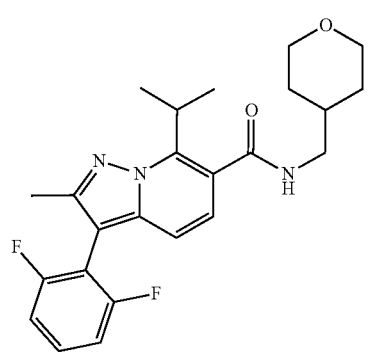 [SMILES: Cc1nn2c(C(C)C)c(C(=O)NCC3CCOCC3)ccc2c1-c1c(F)cccc1F] | 49 |
| 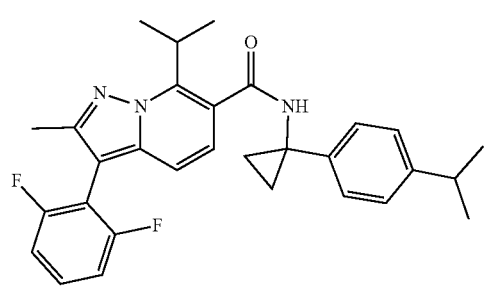 [SMILES: Cc1nn2c(C(C)C)c(C(=O)NC3(c4ccc(C(C)C)cc4)CC3)ccc2c1-c1c(F)cccc1F] | 50 |
| 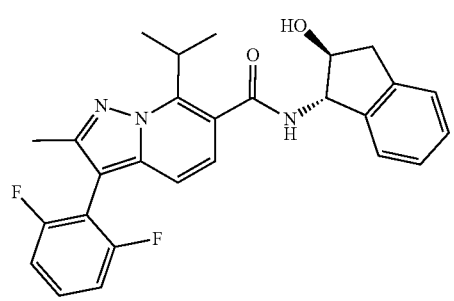 [SMILES: Cc1nn2c(C(C)C)c(C(=O)N[C@H]3c4ccccc4C[C@@H]3O)ccc2c1-c1c(F)cccc1F] | 51 |
| 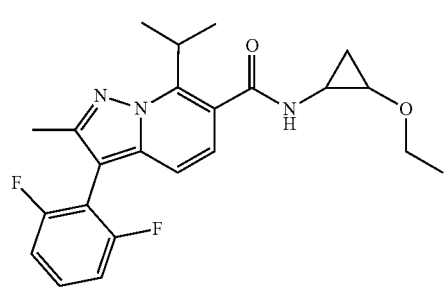 [SMILES: CCOC1CC1NC(=O)c1ccc2c(-c3c(F)cccc3F)c(C)nn2c1C(C)C] | 52 |

TABLE 1-continued

| Structure | Compound # |
|---|---|
| 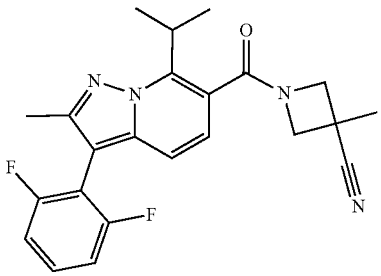 [SMILES: Cc1nn2c(C(C)C)c(C(=O)N3CC(C)(C#N)C3)ccc2c1-c1c(F)cccc1F] | 53 |
| 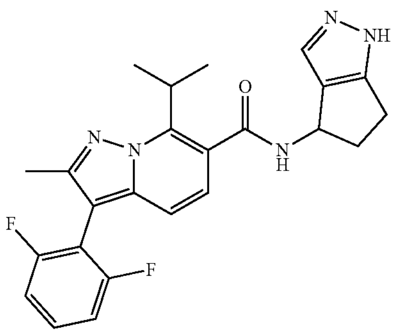 [SMILES: Cc1nn2c(C(C)C)c(C(=O)NC3CCc4[nH]ncc43)ccc2c1-c1c(F)cccc1F] | 54 |
| 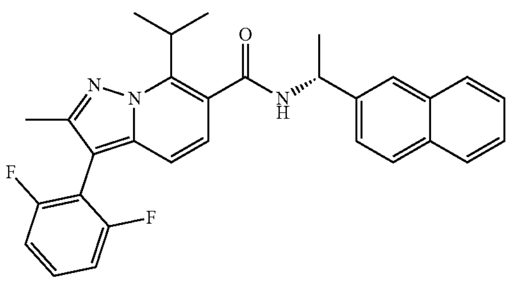 [SMILES: Cc1nn2c(C(C)C)c(C(=O)N[C@H](C)c3ccc4ccccc4c3)ccc2c1-c1c(F)cccc1F] | 55 |
| 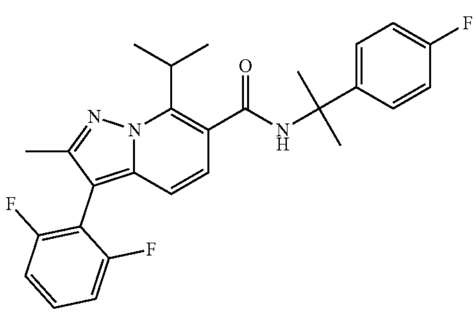 [SMILES: Cc1nn2c(C(C)C)c(C(=O)NC(C)(C)c3ccc(F)cc3)ccc2c1-c1c(F)cccc1F] | 56 |
| 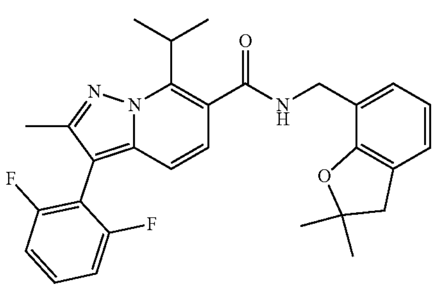 [SMILES: Cc1nn2c(C(C)C)c(C(=O)NCc3cccc4c3OC(C)(C)C4)ccc2c1-c1c(F)cccc1F] | 57 |

TABLE 1-continued
| Structure | Compound # |
|---|---|
| 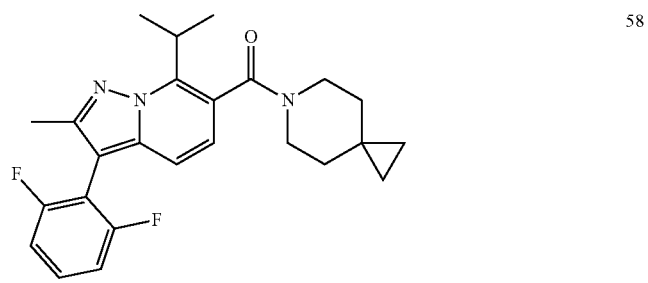 | 58 |
| 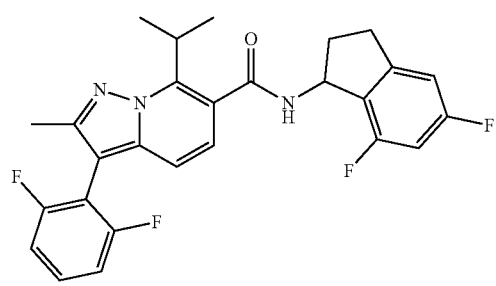 [SMILES: Cc1nn2c(C(C)C)c(C(=O)NC3CCc4cc(F)cc(F)c43)ccc2c1-c1c(F)cccc1F] | 59 |
| 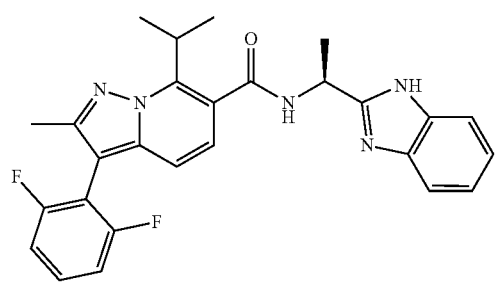 [SMILES: Cc1nn2c(C(C)C)c(C(=O)N[C@@H](C)c3nc4ccccc4[nH]3)ccc2c1-c1c(F)cccc1F] | 60 |
| 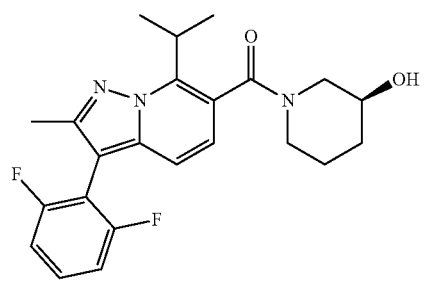 [SMILES: Cc1nn2c(C(C)C)c(C(=O)N3CCC[C@H](O)C3)ccc2c1-c1c(F)cccc1F] | 61 |
| 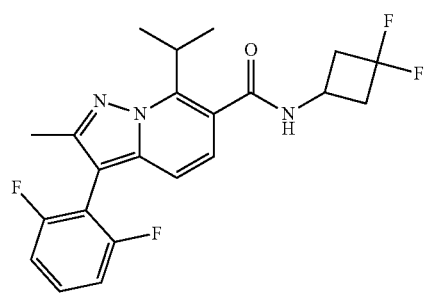 [SMILES: Cc1nn2c(C(C)C)c(C(=O)NC3CC(F)(F)C3)ccc2c1-c1c(F)cccc1F] | 62 |

TABLE 1-continued

| Structure | Compound # |
|---|---|
| 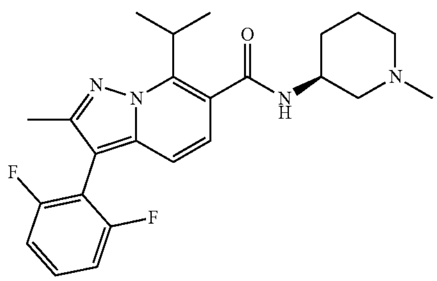 [SMILES: Cc1nn2c(C(C)C)c(C(=O)N[C@H]3CCCN(C)C3)ccc2c1-c1c(F)cccc1F] | 63 |
| 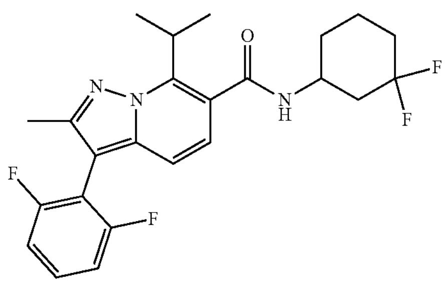 [SMILES: Cc1nn2c(C(C)C)c(C(=O)NC3CCCC(F)(F)C3)ccc2c1-c1c(F)cccc1F] | 64 |
| 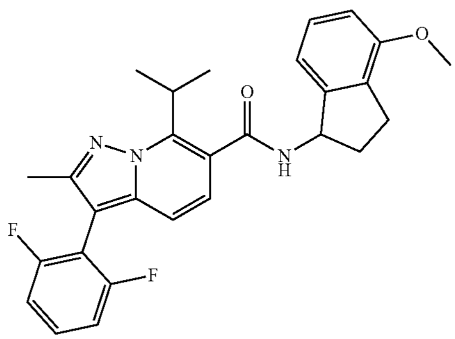 [SMILES: COc1cccc2c1CCC2NC(=O)c1ccc2c(-c3c(F)cccc3F)c(C)nn2c1C(C)C] | 65 |
| 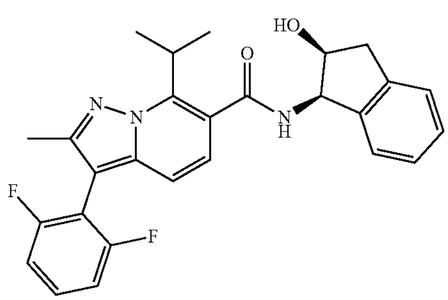 [SMILES: Cc1nn2c(C(C)C)c(C(=O)N[C@@H]3c4ccccc4C[C@@H]3O)ccc2c1-c1c(F)cccc1F] | 66 |
| 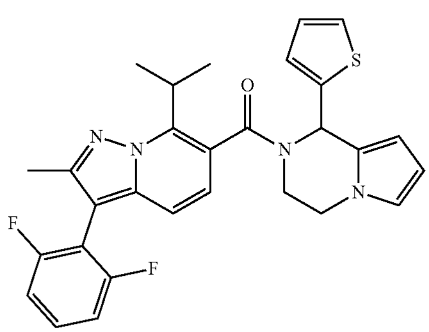 [SMILES: Cc1nn2c(C(C)C)c(C(=O)N3CCn4cccc4C3c3cccs3)ccc2c1-c1c(F)cccc1F] | 67 |

TABLE 1-continued
| Structure | Compound # |
|---|---|
| 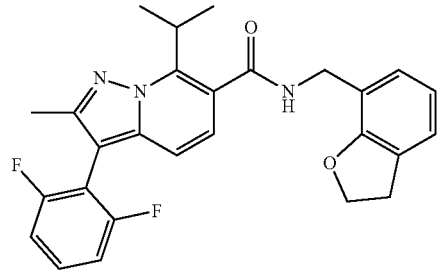 [SMILES: Cc1nn2c(C(C)C)c(C(=O)NCc3cccc4c3OCC4)ccc2c1-c1c(F)cccc1F] | 68 |
| 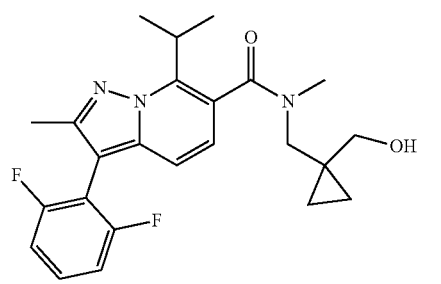 [SMILES: Cc1nn2c(C(C)C)c(C(=O)N(C)CC3(CO)CC3)ccc2c1-c1c(F)cccc1F] | 69 |
| 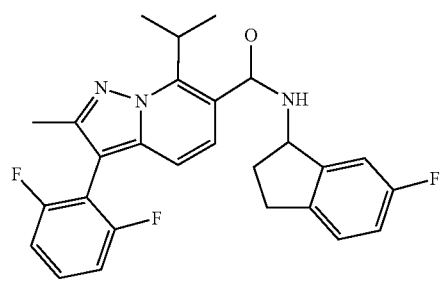 [SMILES: Cc1nn2c(C(C)C)c(COCNC3CCc4ccc(F)cc43)ccc2c1-c1c(F)cccc1F] | 70 |
| 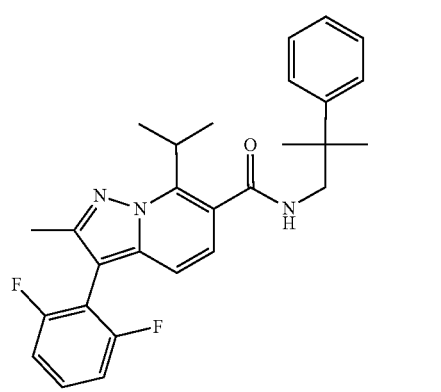 [SMILES: Cc1nn2c(C(C)C)c(C(=O)NCC(C)(C)c3ccccc3)ccc2c1-c1c(F)cccc1F] | 71 |
| 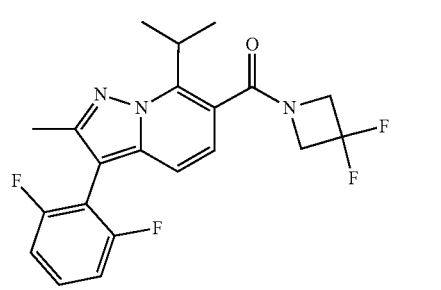 [SMILES: Cc1nn2c(C(C)C)c(C(=O)N3CC(F)(F)C3)ccc2c1-c1c(F)cccc1F] | 72 |

TABLE 1-continued
| Structure | Compound # |
|---|---|
| 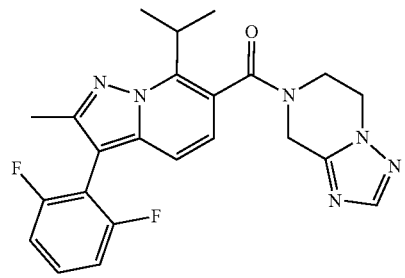 [SMILES: Cc1nn2c(C(C)C)c(C(=O)N3CCn4ncnc4C3)ccc2c1-c1c(F)cccc1F] | 73 |
| 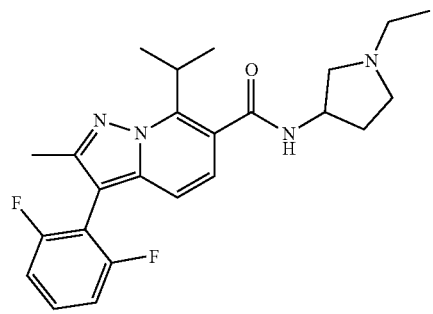 | 74 |
| 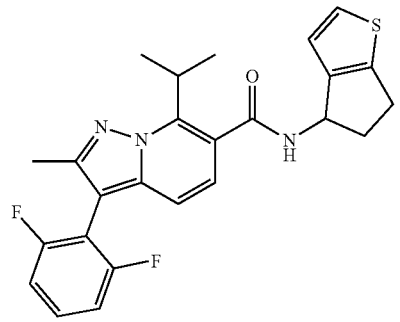 | 75 |
| 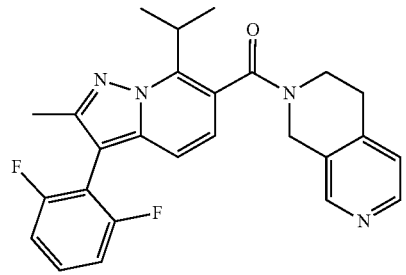 [SMILES: Cc1nn2c(C(C)C)c(C(=O)N3CCc4ccncc4C3)ccc2c1-c1c(F)cccc1F] | 76 |
| 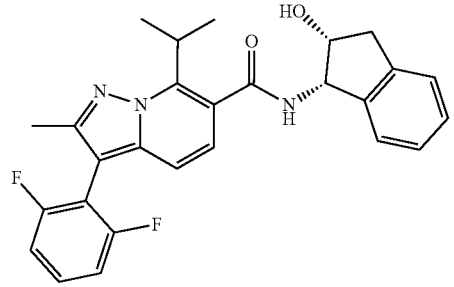 [SMILES: Cc1nn2c(C(C)C)c(C(=O)N[C@H]3c4ccccc4C[C@H]3O)ccc2c1-c1c(F)cccc1F] | 77 |

TABLE 1-continued
| Structure | Compound # |
|---|---|
| 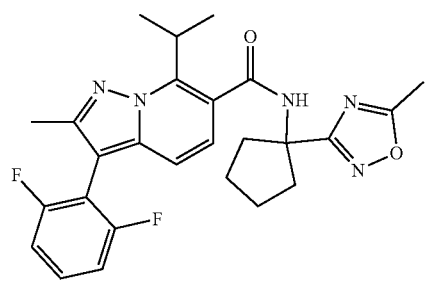 [SMILES: Cc1nc(C2(NC(=O)c3ccc4c(-c5c(F)cccc5F)c(C)nn4c3C(C)C)CCCC2)no1] | 78 |
| 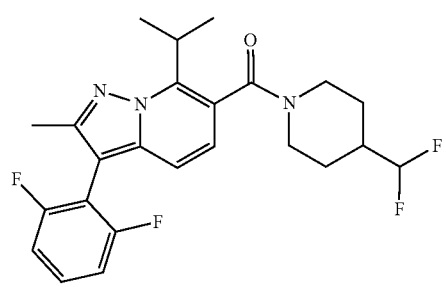 [SMILES: Cc1nn2c(C(C)C)c(C(=O)N3CCC(C(F)F)CC3)ccc2c1-c1c(F)cccc1F] | 79 |
| 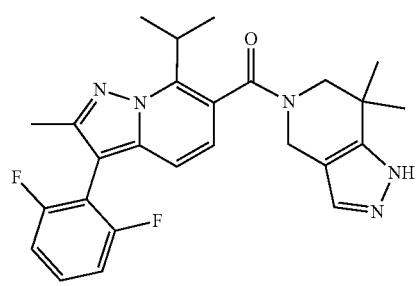 [SMILES: Cc1nn2c(C(C)C)c(C(=O)N3Cc4cn[nH]c4C(C)(C)C3)ccc2c1-c1c(F)cccc1F] | 80 |
| 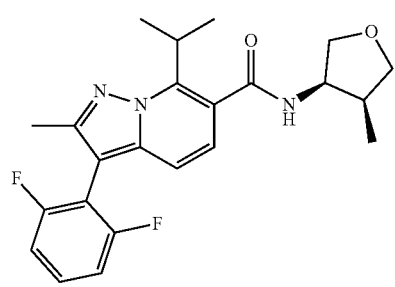 [SMILES: Cc1nn2c(C(C)C)c(C(=O)N[C@H]3COC[C@H]3C)ccc2c1-c1c(F)cccc1F] | 81 |
| 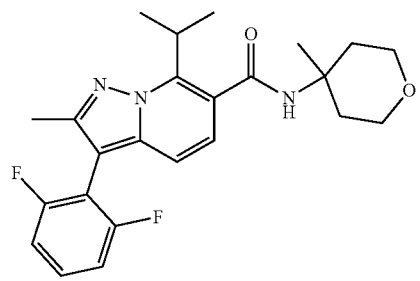 [SMILES: Cc1nn2c(C(C)C)c(C(=O)NC3(C)CCOCC3)ccc2c1-c1c(F)cccc1F] | 82 |

TABLE 1-continued
| Structure | Compound # |
|---|---|
| 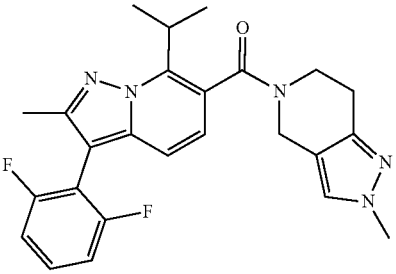 [SMILES: Cc1nn2c(C(C)C)c(C(=O)N3CCc4nn(C)cc4C3)ccc2c1-c1c(F)cccc1F] | 83 |
| 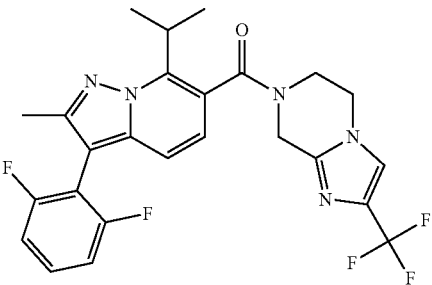 [SMILES: Cc1nn2c(C(C)C)c(C(=O)N3CCn4cc(C(F)(F)F)nc4C3)ccc2c1-c1c(F)cccc1F] | 84 |
| 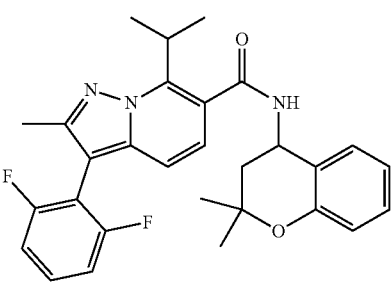 [SMILES: Cc1nn2c(C(C)C)c(C(=O)NC3CC(C)(C)Oc4ccccc43)ccc2c1-c1c(F)cccc1F] | 85 |
| 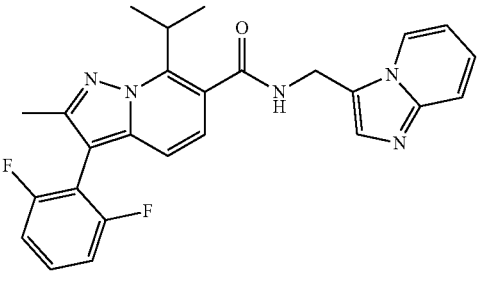 [SMILES: Cc1nn2c(C(C)C)c(C(=O)NCc3cnc4ccccn34)ccc2c1-c1c(F)cccc1F] | 86 |
| 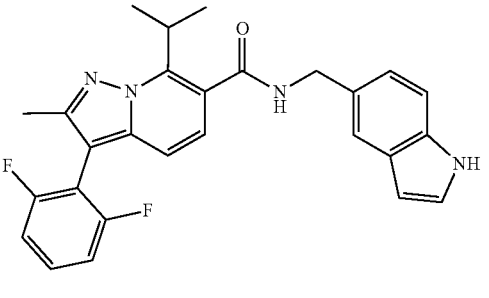 [SMILES: Cc1nn2c(C(C)C)c(C(=O)NCc3ccc4[nH]ccc4c3)ccc2c1-c1c(F)cccc1F] | 87 |

TABLE 1-continued
| Structure | Compound # |
|---|---|
| 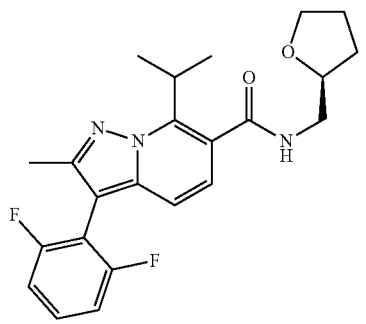 [SMILES: Cc1nn2c(C(C)C)c(C(=O)NC[C@@H]3CCCO3)ccc2c1-c1c(F)cccc1F] | 88 |
| 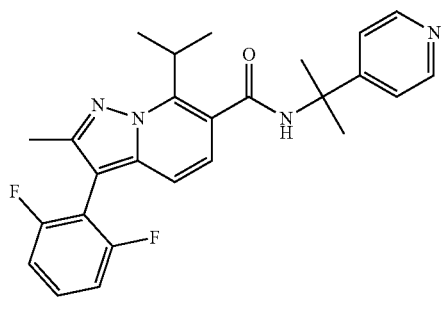 [SMILES: Cc1nn2c(C(C)C)c(C(=O)NC(C)(C)c3ccncc3)ccc2c1-c1c(F)cccc1F] | 89 |
| 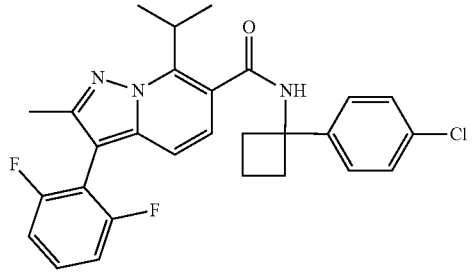 [SMILES: Cc1nn2c(C(C)C)c(C(=O)NC3(c4ccc(Cl)cc4)CCC3)ccc2c1-c1c(F)cccc1F] | 90 |
| 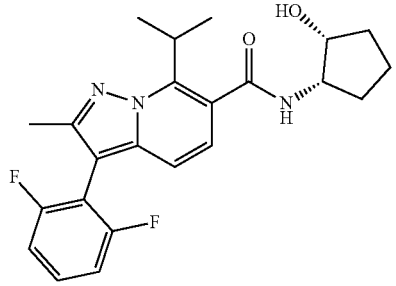 [SMILES: Cc1nn2c(C(C)C)c(C(=O)N[C@H]3CCC[C@H]3O)ccc2c1-c1c(F)cccc1F] | 91 |
| 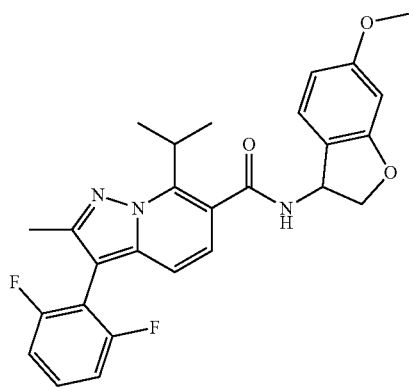 [SMILES: COc1ccc2c(c1)OCC2NC(=O)c1ccc2c(-c3c(F)cccc3F)c(C)nn2c1C(C)C] | 92 |

TABLE 1-continued

| Structure | Compound # |
|---|---|
| 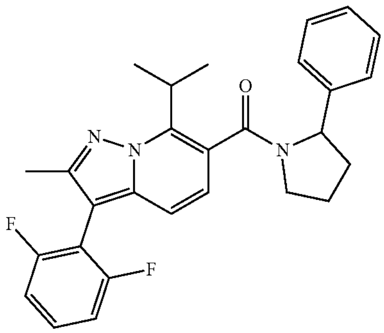 [SMILES: Cc1nn2c(C(C)C)c(C(=O)N3CCCC3c3ccccc3)ccc2c1-c1c(F)cccc1F] | 93 |
| 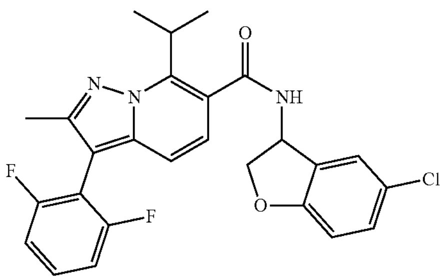 [SMILES: Cc1nn2c(C(C)C)c(C(=O)NC3COc4ccc(Cl)cc43)ccc2c1-c1c(F)cccc1F] | 94 |
| 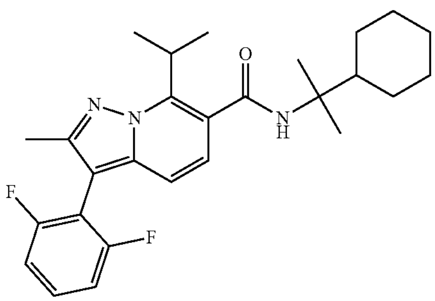 [SMILES: Cc1nn2c(C(C)C)c(C(=O)NC(C)(C)C3CCCCC3)ccc2c1-c1c(F)cccc1F] | 95 |
| 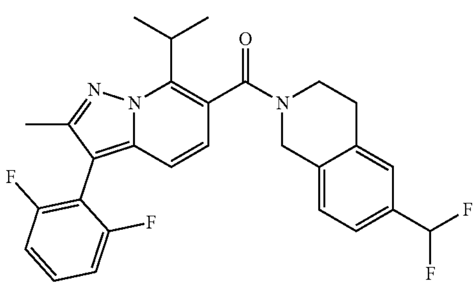 [SMILES: Cc1nn2c(C(C)C)c(C(=O)N3CCc4cc(C(F)F)ccc4C3)ccc2c1-c1c(F)cccc1F] | 96 |
| 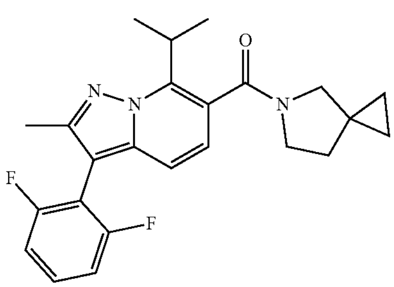 [SMILES: Cc1nn2c(C(C)C)c(C(=O)N3CCC4(CC4)C3)ccc2c1-c1c(F)cccc1F] | 97 |

TABLE 1-continued
| Structure | Compound # |
|---|---|
| 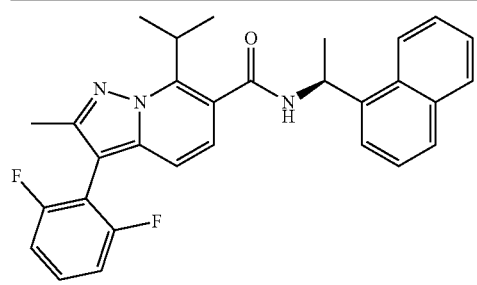 [SMILES: Cc1nn2c(C(C)C)c(C(=O)N[C@@H](C)c3cccc4ccccc34)ccc2c1-c1c(F)cccc1F] | 98 |
| 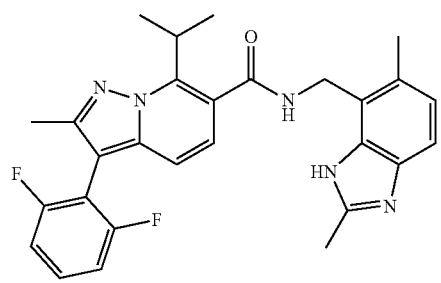 [SMILES: Cc1nc2ccc(C)c(CNC(=O)c3ccc4c(-c5c(F)cccc5F)c(C)nn4c3C(C)C)c2[nH]1] | 99 |
| 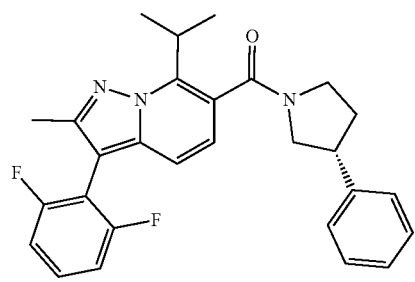 [SMILES: Cc1nn2c(C(C)C)c(C(=O)N3CC[C@H](c4ccccc4)C3)ccc2c1-c1c(F)cccc1F] | 100 |
| 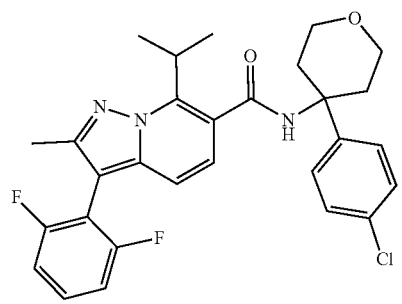 [SMILES: Cc1nn2c(C(C)C)c(C(=O)NC3(c4ccc(Cl)cc4)CCOCC3)ccc2c1-c1c(F)cccc1F] | 101 |
| 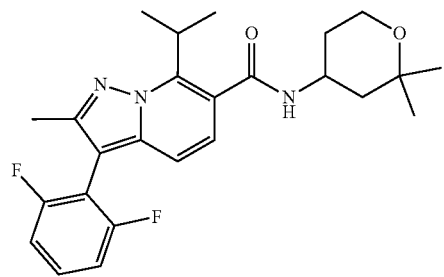 [SMILES: Cc1nn2c(C(C)C)c(C(=O)NC3CCOC(C)(C)C3)ccc2c1-c1c(F)cccc1F] | 102 |

TABLE 1-continued
| Structure | Compound # |
|---|---|
| 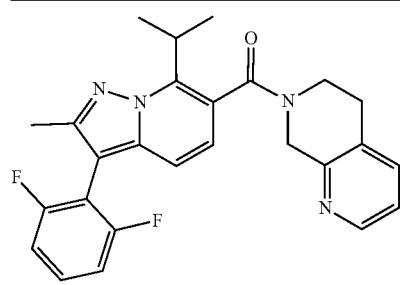 | 103 |
| 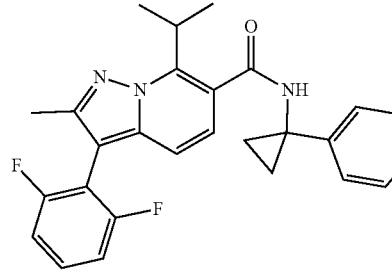 | 104 |
| 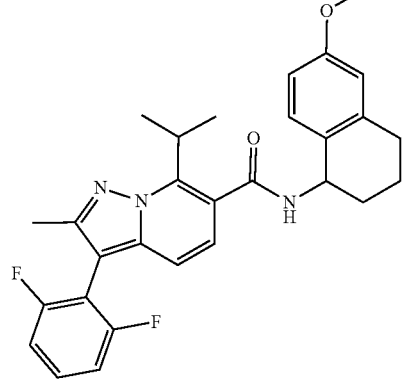 | 105 |
| 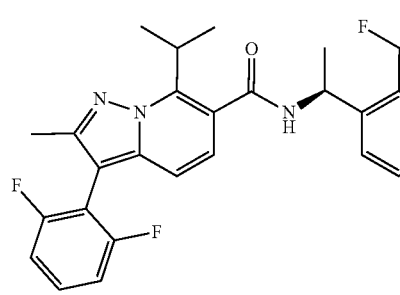 | 106 |
| 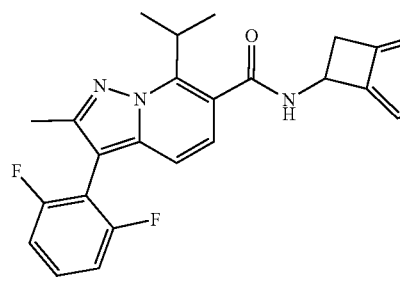 | 107 |

TABLE 1-continued
| Structure | Compound # |
|---|---|
| 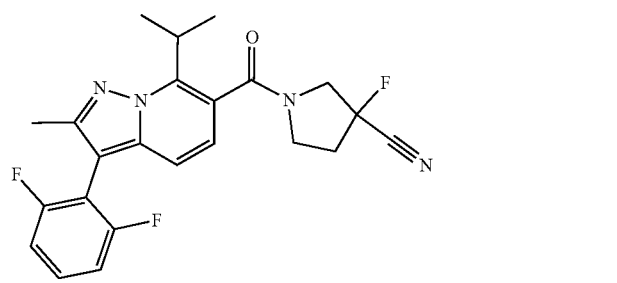 | 108 |
| 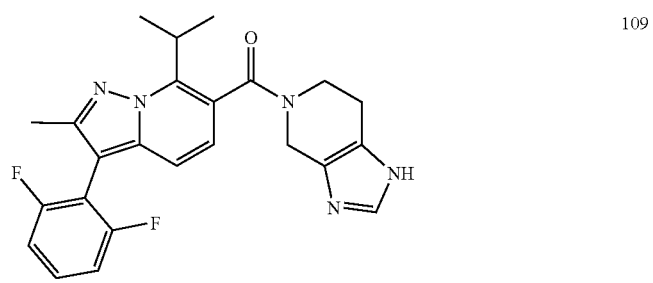 | 109 |
| 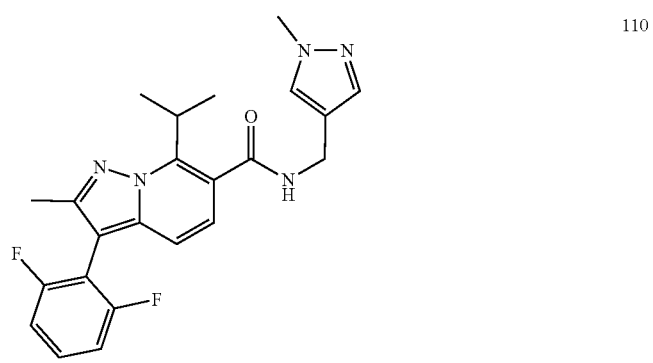 | 110 |
| 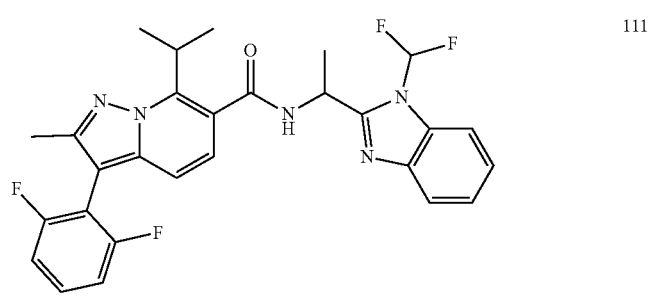 | 111 |
| 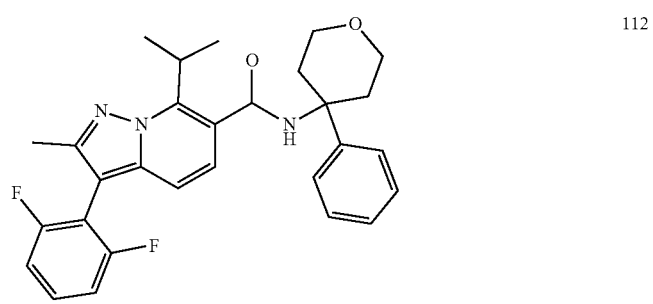 | 112 |

TABLE 1-continued
| Structure | Compound # |
|---|---|
| 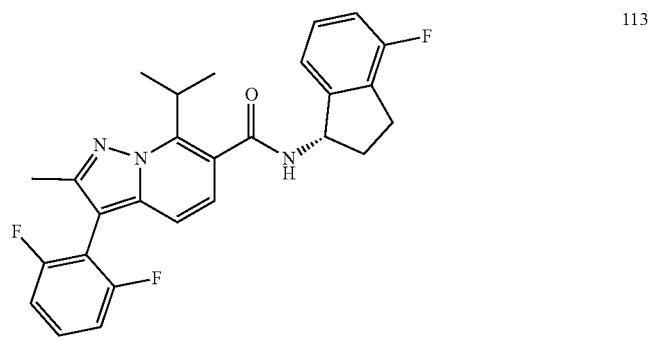 | 113 |
| 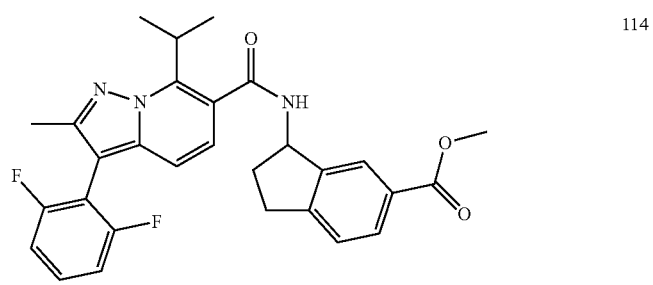 | 114 |
| 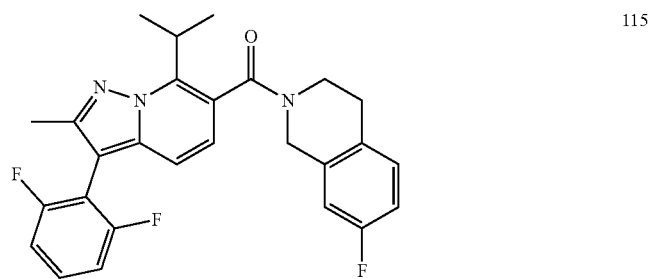 | 115 |
| 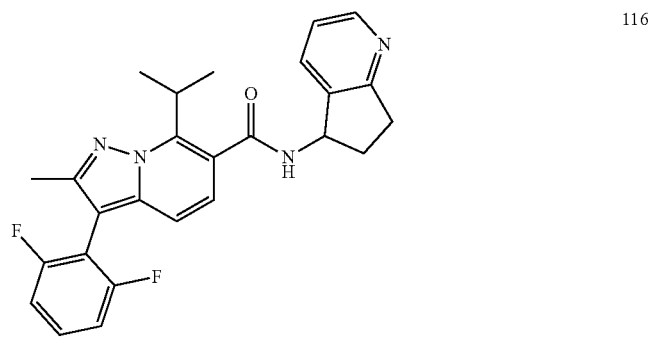 | 116 |
| 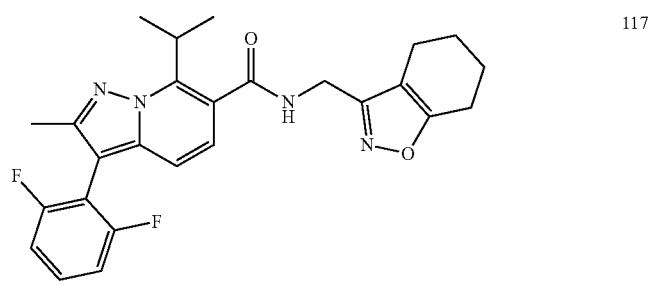 | 117 |

TABLE 1-continued

| Structure | Compound # |
|---|---|
| 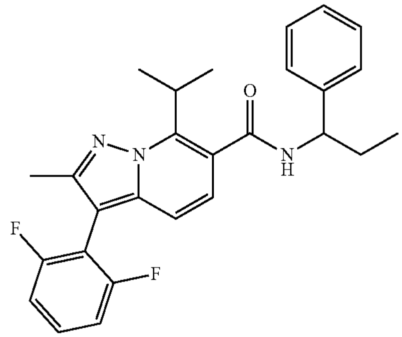 [SMILES: CCC(NC(=O)c1ccc2c(-c3c(F)cccc3F)c(C)nn2c1C(C)C)c1ccccc1] | 118 |
| 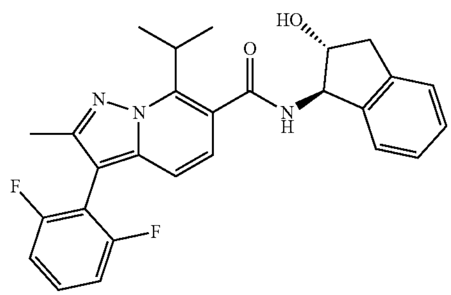 [SMILES: Cc1nn2c(C(C)C)c(C(=O)N[C@@H]3c4ccccc4C[C@H]3O)ccc2c1-c1c(F)cccc1F] | 119 |
| 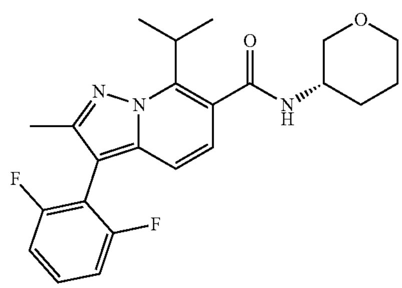 [SMILES: Cc1nn2c(C(C)C)c(C(=O)N[C@H]3CCCOC3)ccc2c1-c1c(F)cccc1F] | 120 |
| 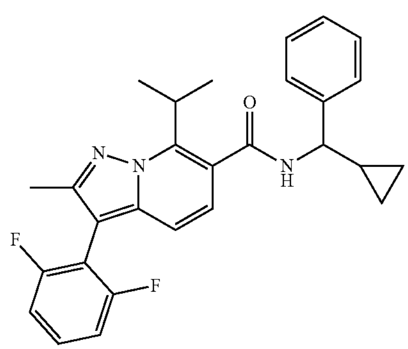 [SMILES: Cc1nn2c(C(C)C)c(C(=O)NC(c3ccccc3)C3CC3)ccc2c1-c1c(F)cccc1F] | 121 |
| 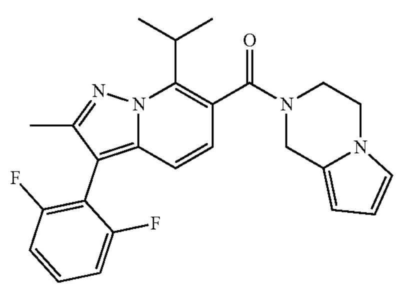 [SMILES: Cc1nn2c(C(C)C)c(C(=O)N3CCn4cccc4C3)ccc2c1-c1c(F)cccc1F] | 122 |

TABLE 1-continued
| Structure | Compound # |
|---|---|
| 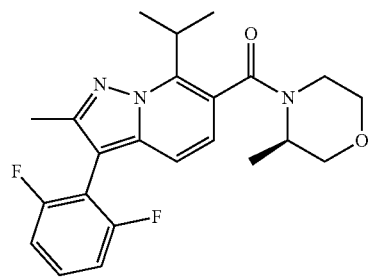 [SMILES: Cc1nn2c(C(C)C)c(C(=O)N3CCOC[C@H]3C)ccc2c1-c1c(F)cccc1F] | 123 |
| 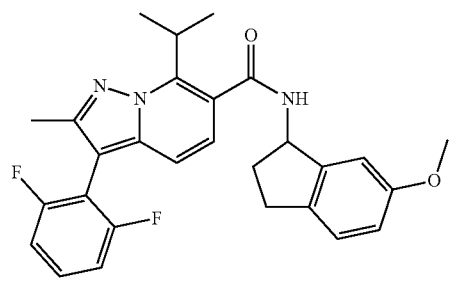 [SMILES: COc1ccc2c(c1)C(NC(=O)c1ccc3c(-c4c(F)cccc4F)c(C)nn3c1C(C)C)CC2] | 124 |
| 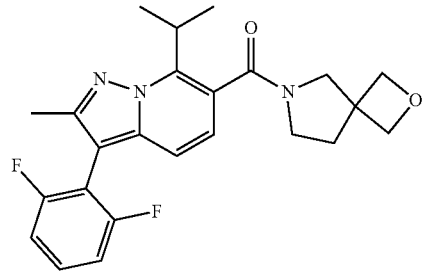 [SMILES: Cc1nn2c(C(C)C)c(C(=O)N3CCC4(COC4)C3)ccc2c1-c1c(F)cccc1F] | 125 |
| 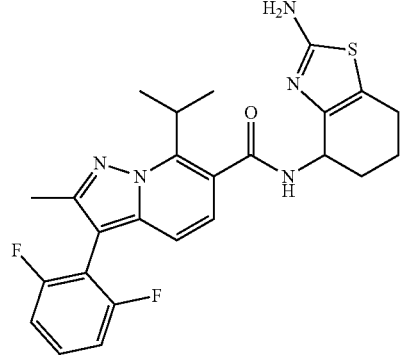 [SMILES: Cc1nn2c(C(C)C)c(C(=O)NC3CCCc4sc(N)nc43)ccc2c1-c1c(F)cccc1F] | 126 |
| 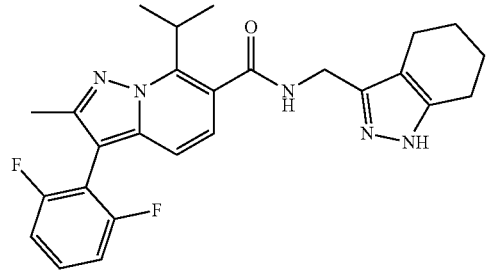 [SMILES: Cc1nn2c(C(C)C)c(C(=O)NCc3n[nH]c4c3CCCC4)ccc2c1-c1c(F)cccc1F] | 127 |

TABLE 1-continued

| Structure | Compound # |
|---|---|
| 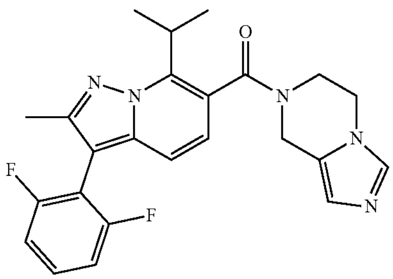 [SMILES: Cc1nn2c(C(C)C)c(C(=O)N3CCn4cncc4C3)ccc2c1-c1c(F)cccc1F] | 128 |
| 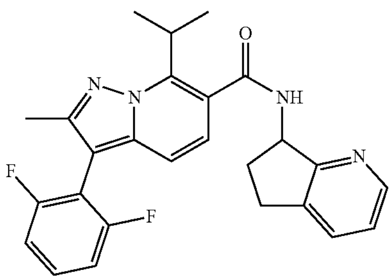 [SMILES: Cc1nn2c(C(C)C)c(C(=O)NC3CCc4cccnc43)ccc2c1-c1c(F)cccc1F] | 129 |
| 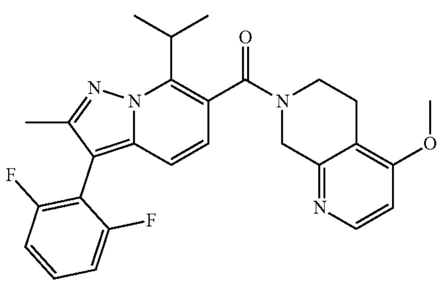 [SMILES: COc1ccnc2c1CCN(C(=O)c1ccc3c(-c4c(F)cccc4F)c(C)nn3c1C(C)C)C2] | 130 |
| 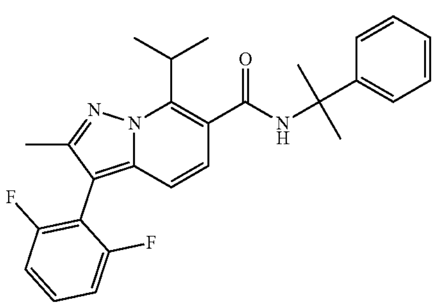 [SMILES: Cc1nn2c(C(C)C)c(C(=O)NC(C)(C)c3ccccc3)ccc2c1-c1c(F)cccc1F] | 131 |
| 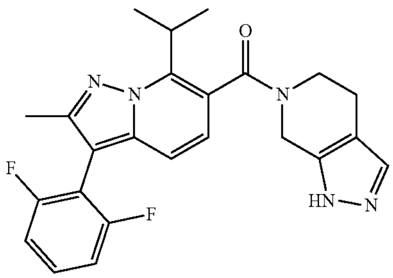 [SMILES: Cc1nn2c(C(C)C)c(C(=O)N3CCc4cn[nH]c4C3)ccc2c1-c1c(F)cccc1F] | 132 |

TABLE 1-continued
| Structure | Compound # |
|---|---|
| 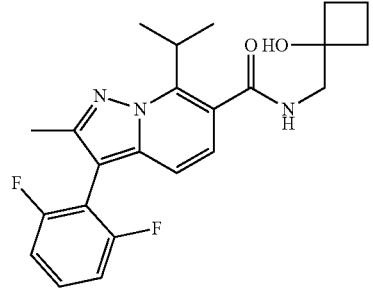 [SMILES: Cc1nn2c(C(C)C)c(C(=O)NCC3(O)CCC3)ccc2c1-c1c(F)cccc1F] | 133 |
| 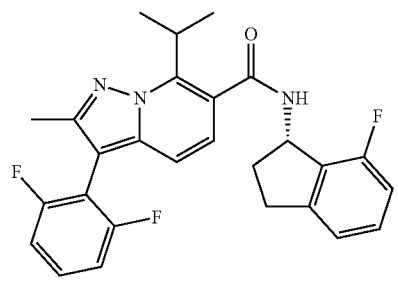 [SMILES: Cc1nn2c(C(C)C)c(C(=O)N[C@H]3CCc4cccc(F)c43)ccc2c1-c1c(F)cccc1F] | 134 |
| 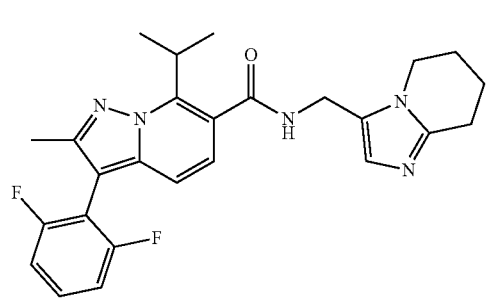 | 135 |
| 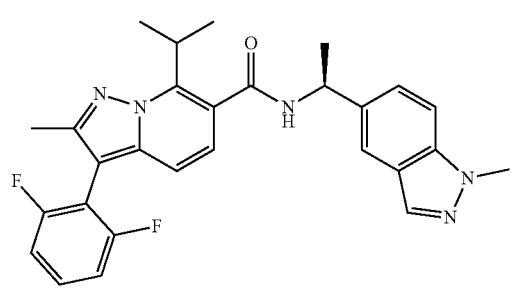 [SMILES: Cc1nn2c(C(C)C)c(C(=O)N[C@@H](C)c3ccc4c(cnn4C)c3)ccc2c1-c1c(F)cccc1F] | 136 |
| 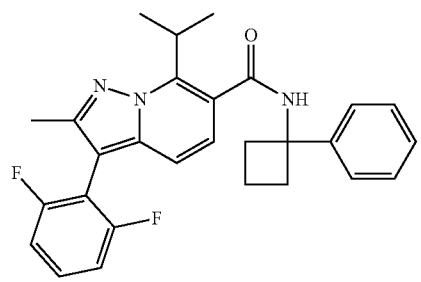 [SMILES: Cc1nn2c(C(C)C)c(C(=O)NC3(c4ccccc4)CCC3)ccc2c1-c1c(F)cccc1F] | 137 |

TABLE 1-continued

| Structure | Compound # |
|---|---|
| 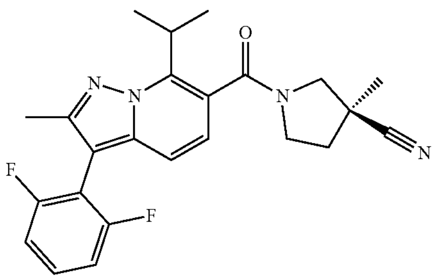 [SMILES: Cc1nn2c(C(C)C)c(C(=O)N3CC[C@](C)(C#N)C3)ccc2c1-c1c(F)cccc1F] | 138 |
| 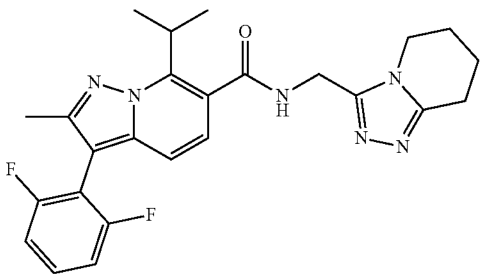 [SMILES: Cc1nn2c(C(C)C)c(C(=O)NCc3nnc4n3CCCC4)ccc2c1-c1c(F)cccc1F] | 139 |
| 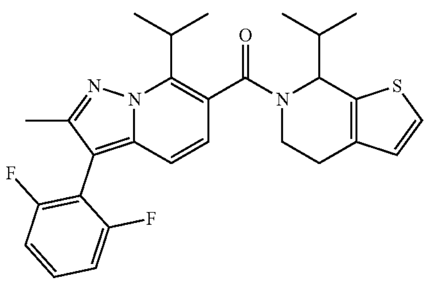 [SMILES: Cc1nn2c(C(C)C)c(C(=O)N3CCc4ccsc4C3C(C)C)ccc2c1-c1c(F)cccc1F] | 140 |
| 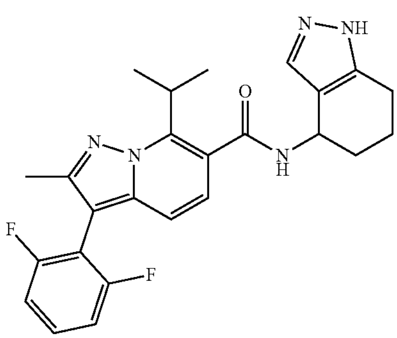 [SMILES: Cc1nn2c(C(C)C)c(C(=O)NC3CCCc4[nH]ncc43)ccc2c1-c1c(F)cccc1F] | 141 |
| 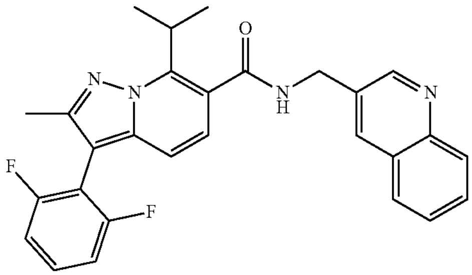 [SMILES: Cc1nn2c(C(C)C)c(C(=O)NCc3cnc4ccccc4c3)ccc2c1-c1c(F)cccc1F] | 142 |

TABLE 1-continued
| Structure | Compound # |
|---|---|
| 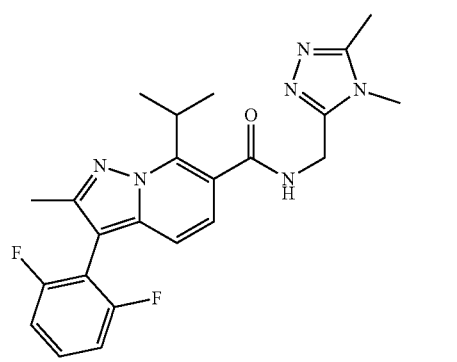 [SMILES: Cc1nn2c(C(C)C)c(C(=O)NCc3nnc(C)n3C)ccc2c1-c1c(F)cccc1F] | 143 |
| 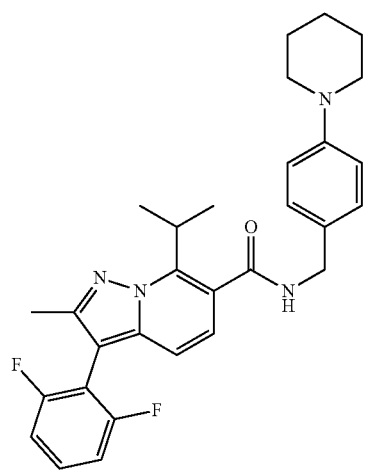 [SMILES: Cc1nn2c(C(C)C)c(C(=O)NCc3ccc(N4CCCCC4)cc3)ccc2c1-c1c(F)cccc1F] | 144 |
| 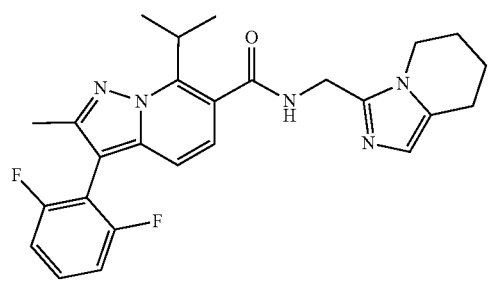 [SMILES: Cc1nn2c(C(C)C)c(C(=O)NCc3ncc4n3CCCC4)ccc2c1-c1c(F)cccc1F] | 145 |
| 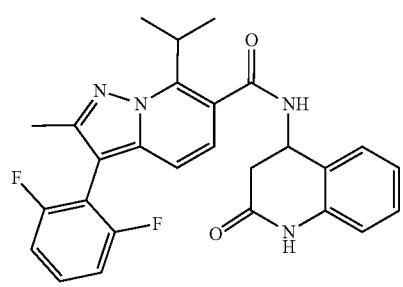 [SMILES: Cc1nn2c(C(C)C)c(C(=O)NC3CC(=O)Nc4ccccc43)ccc2c1-c1c(F)cccc1F] | 146 |

TABLE 1-continued
| Structure | Compound # |
|---|---|
| 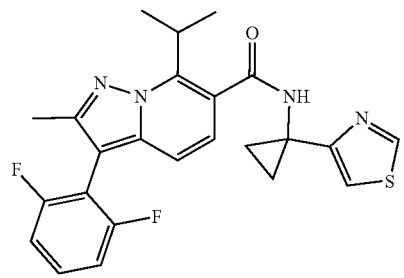 [SMILES: Cc1nn2c(C(C)C)c(C(=O)NC3(c4cscn4)CC3)ccc2c1-c1c(F)cccc1F] | 147 |
| 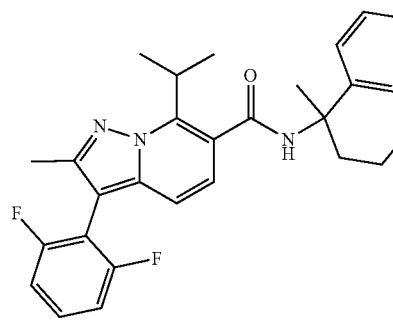 | 148 |
| 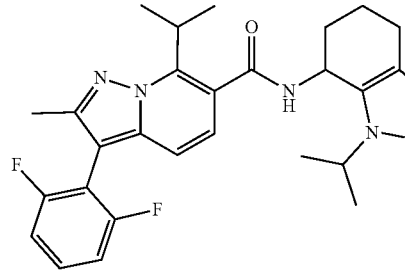 | 149 |
| 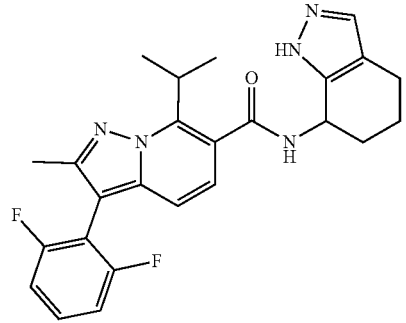 [SMILES: Cc1nn2c(C(C)C)c(C(=O)NC3CCCc4cn[nH]c43)ccc2c1-c1c(F)cccc1F] | 150 |
| 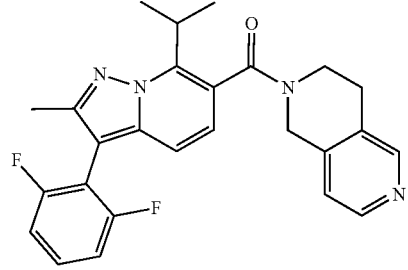 [SMILES: Cc1nn2c(C(C)C)c(C(=O)N3CCc4cnccc4C3)ccc2c1-c1c(F)cccc1F] | 151 |

TABLE 1-continued
| Structure | Compound # |
|---|---|
| 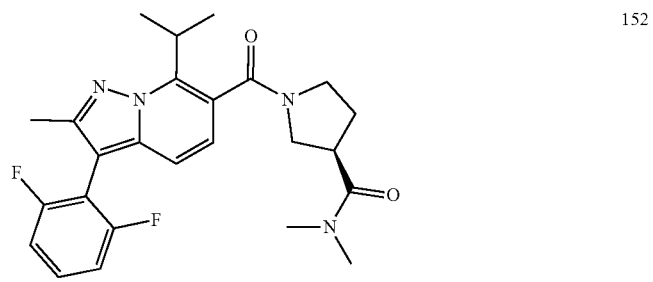 | 152 |
| 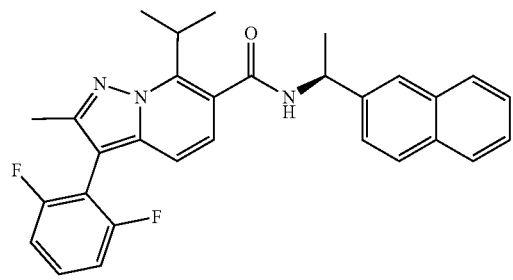 [SMILES: Cc1nn2c(C(C)C)c(C(=O)N[C@@H](C)c3ccc4ccccc4c3)ccc2c1-c1c(F)cccc1F] | 153 |
| 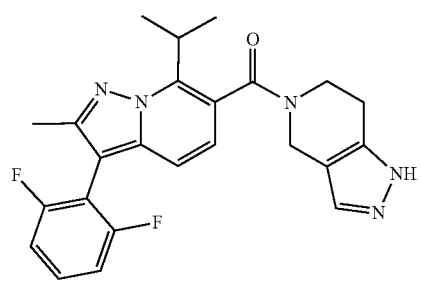 [SMILES: Cc1nn2c(C(C)C)c(C(=O)N3CCc4[nH]ncc4C3)ccc2c1-c1c(F)cccc1F] | 154 |
| 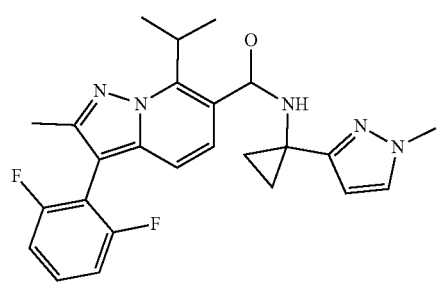 [SMILES: Cc1nn2c(C(C)C)c(COCNC3(c4ccn(C)n4)CC3)ccc2c1-c1c(F)cccc1F] | 155 |
| 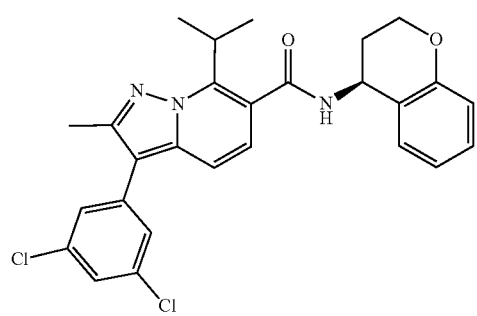 [SMILES: Cc1nn2c(C(C)C)c(C(=O)N[C@H]3CCOc4ccccc43)ccc2c1-c1cc(Cl)cc(Cl)c1] | 156 |

TABLE 1-continued

| Structure | Compound # |
|---|---|
| (structure) | 157 |
| (structure) | 158 |
| (structure) | 159 |
| (structure) | 160 |

TABLE 1-continued

| Structure | Compound # |
|---|---|
| 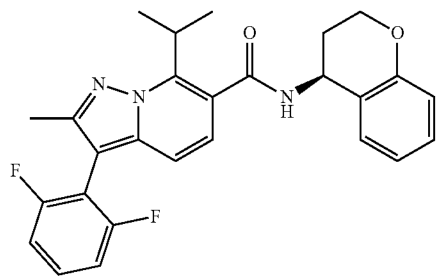 [SMILES: Cc1nn2c(C(C)C)c(C(=O)N[C@H]3CCOc4ccccc43)ccc2c1-c1c(F)cccc1F] | 161 |
| 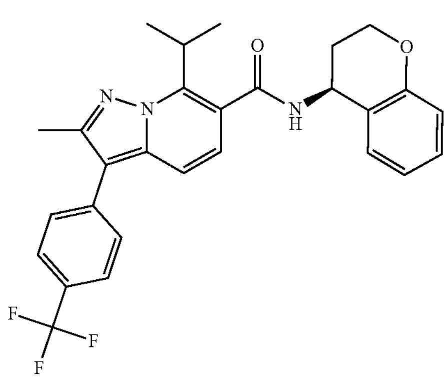 [SMILES: Cc1nn2c(C(C)C)c(C(=O)N[C@H]3CCOc4ccccc43)ccc2c1-c1ccc(C(F)(F)F)cc1] | 162 |
| 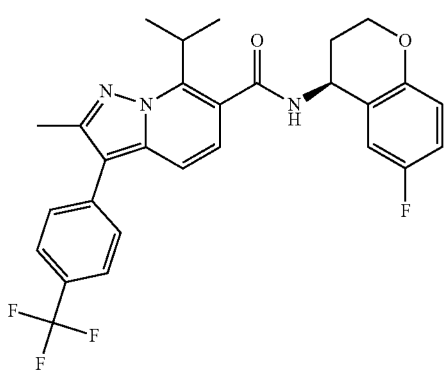 [SMILES: Cc1nn2c(C(C)C)c(C(=O)N[C@H]3CCOc4ccc(F)cc43)ccc2c1-c1ccc(C(F)(F)F)cc1] | 163 |
| 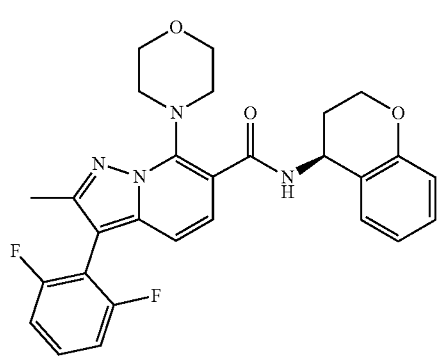 [SMILES: Cc1nn2c(N3CCOCC3)c(C(=O)N[C@H]3CCOc4ccccc43)ccc2c1-c1c(F)cccc1F] | 164 |

TABLE 1-continued
| Structure | Compound # |
|---|---|
| 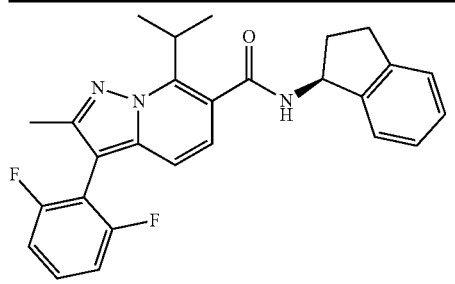 | 165 |
| 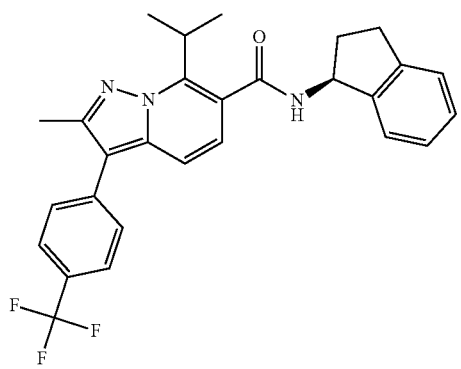 [SMILES: Cc1nn2c(C(C)C)c(C(=O)N[C@H]3CCc4ccccc43)ccc2c1-c1ccc(C(F)(F)F)cc1] | 166 |
| 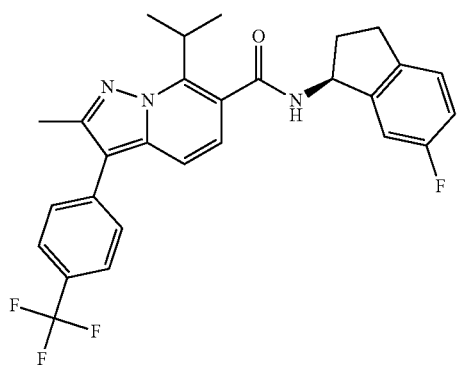 [SMILES: Cc1nn2c(C(C)C)c(C(=O)N[C@H]3CCc4ccc(F)cc43)ccc2c1-c1ccc(C(F)(F)F)cc1] | 167 |
| 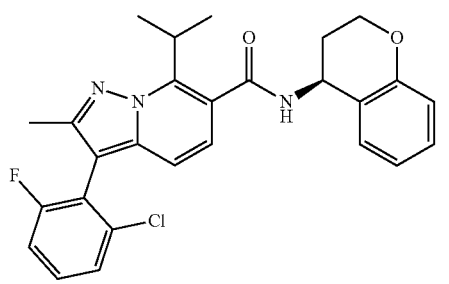 [SMILES: Cc1nn2c(C(C)C)c(C(=O)N[C@H]3CCOc4ccccc43)ccc2c1-c1c(F)cccc1Cl] | 168 |
| 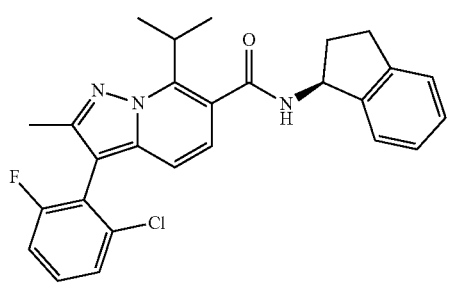 [SMILES: Cc1nn2c(C(C)C)c(C(=O)N[C@H]3CCc4ccccc43)ccc2c1-c1c(F)cccc1Cl] | 169 |

TABLE 1-continued

| Structure | Compound # |
|---|---|
| 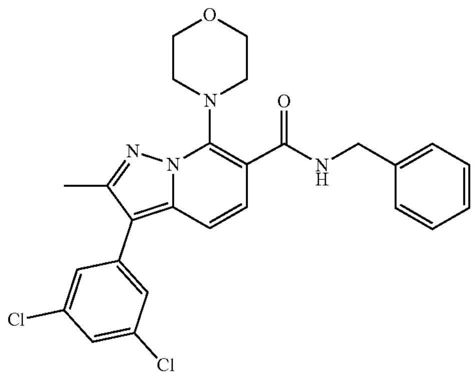 [SMILES: Cc1nn2c(N3CCOCC3)c(C(=O)NCc3ccccc3)ccc2c1-c1cc(Cl)cc(Cl)c1] | 170 |
| 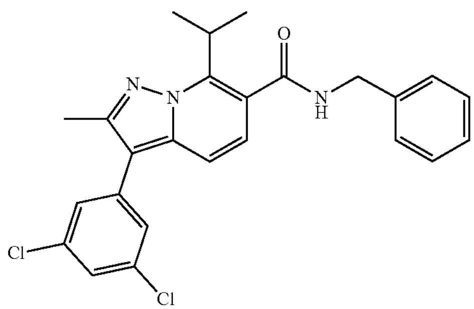 [SMILES: Cc1nn2c(C(C)C)c(C(=O)NCc3ccccc3)ccc2c1-c1cc(Cl)cc(Cl)c1] | 171 |
| 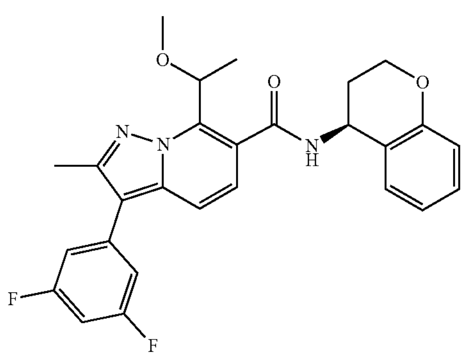 [SMILES: COC(C)c1c(C(=O)N[C@H]2CCOc3ccccc32)ccc2c(-c3cc(F)cc(F)c3)c(C)nn12] | 172 |
| 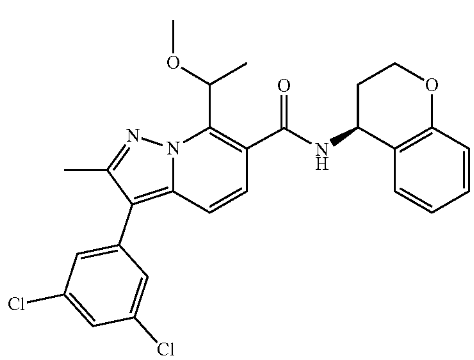 [SMILES: COC(C)c1c(C(=O)N[C@H]2CCOc3ccccc32)ccc2c(-c3cc(Cl)cc(Cl)c3)c(C)nn12] | 173 |

Example 16

Four hundred to six hundred microfilariae of *Dirofilaria immitis* were added to wells of a microtiter plate containing RPMI media and the test compound formulated in 100% DMSO. Plates were held for three days at 37° C. and 5% $CO_2$. The efficacy of a compound was determined based on the motility of the microfilaria as compared to average motility of control wells containing DMSO only. A dose response assay was conducted to determine an $EC_{50}$ value. The following compounds from Table 1 showed activity against *Dirofilaria immitis*: 2-4, 8-10, 14, 15, 20, 25, 32-39, 113, 124, 156-159, 161, 162, 164, 165, 168, 170, and 172.

What is claimed is:

1. A compound of formula (I):

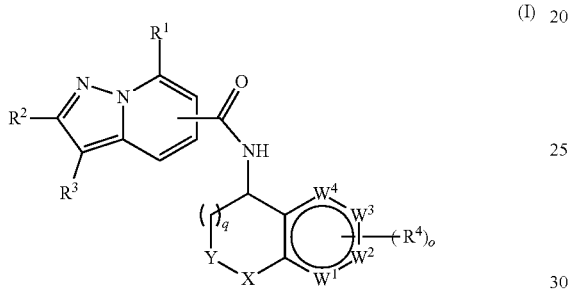

(I)

wherein:
$W^1$ $W^2$, $W^3$ and $W^4$ are independently C—H or N;
$R^1$ is cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted haloalkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$SO_n$, amino, NH-optionally substituted alkyl, or $NR^aR^b$ wherein $R^a$ and $R^b$ are independently optionally substituted $C_1$-$C_4$ alkyl; or $R^a$ and $R^b$ may form, with the nitrogen to which they are attached, a 3, 4, 5, 6, 7, or 8 membered-heterocyclyl group, which may be optionally substituted;
$R^2$ is halogen, cyano, optionally substituted alkoxy, optionally substituted aryloxy, optionally substituted alkyl, optionally substituted $C_3$-$C_8$-cycloalkyl, or $SO_m$ (optionally substituted alkyl);
$R^3$ is selected from the group consisting of 6- or 10-membered aryl and 5- to 10-membered heteroaryl, each of which may be optionally substituted with 1, 2, 3, 4 or 5 substituents;
each $R^4$ is independently hydrogen, halogen, cyano, nitro, —OH, optionally substituted alkyl, optionally substituted alkoxy, optionally substituted cycloalkyl, -amino, NH-optionally substituted alkyl, $SF_5$, or $NR^cR^d$ wherein $R^c$ and $R^d$ are independently optionally substituted alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted $C_1$-$C_4$-alkyl);
o is 0, 1, 2, 3, or 4;
m, n, and p are independently 0, 1, or 2;
q is 0 or 1;
X and Y are independently $CR^5R^6$, O, S, or N—$R^7$, wherein at least one of X and Y is $CR^5R^6$;
$R^5$ and $R^6$ are independently hydrogen, fluorine or $C_1$-$C_4$-alkyl;
$R^7$ is hydrogen or $C_1$-$C_4$-alkyl; or
a stereoisomer, tautomer, N-oxide, hydrate, solvate, or salt thereof.

2. A compound according to claim 1, wherein the compound has the structure of formula (I-1):

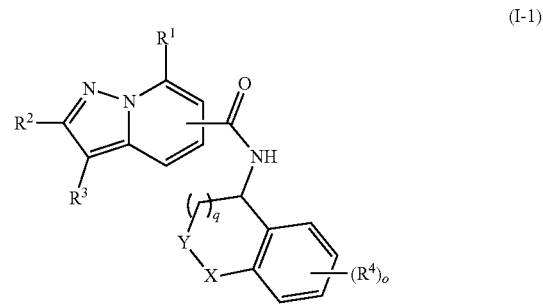

(I-1)

wherein:
$R^1$ is cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$S(O)_n$, amino, NH-optionally substituted alkyl, or $NR^aR^b$ wherein $R^a$ and $R^b$ are independently optionally substituted $C_1$-$C_4$ alkyl; or $R^a$ and $R^b$ may form, with the nitrogen to which they are attached, a 3, 4, 5, 6, 7, or 8 membered-heterocyclyl group, which may be optionally substituted;
$R^2$ is halogen, cyano, optionally substituted alkoxy, optionally substituted aryloxy, optionally substituted $C_1$-$C_4$-alkyl, optionally substituted $C_3$-$C_6$-cycloalkyl, or $SO_m$(optionally substituted $C_1$-$C_4$-alkyl);
$R^3$ is selected from the group consisting of 6- or 10-membered aryl and 5- to 10-membered heteroaryl, each of which may be optionally substituted with 1, 2, 3, 4 or 5 substituents;
each $R^4$ is independently hydrogen, halogen, cyano, nitro, —OH, optionally substituted alkyl, optionally substituted alkoxy, optionally substituted cycloalkyl, -amino, NH-optionally substituted alkyl, $SF_5$, or $NR^cR^d$ wherein $R^c$ and $R^d$ are independently optionally substituted alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted $C_1$-$C_4$-alkyl);
o is 0, 1, 2, 3, or 4;

m, n, and p are independently 0, 1, or 2;

q is 0 or 1;

X and Y are independently $CR^5R^6$, O, S, or N—$R^7$, wherein at least one of X and Y is $CR^5R^6$;

$R^5$ and $R^6$ are independently hydrogen, fluorine or $C_1$-$C_4$-alkyl;

$R^7$ is hydrogen or $C_1$-$C_4$-alkyl; or a stereoisomer, tautomer, N-oxide, hydrate, solvate, or salt thereof.

3. The compound according to claim 2 wherein $R^1$ is secondary $C_1$-$C_4$-alkyl.

4. The compound of claim 2 wherein $R^1$ is heterocyclyl.

5. The compound of claim 4 wherein $R^1$ is aziridinyl, azetidinyl, oxetanyl, pyrrolidinyl, pyrrolyl, or morpholinyl, all of which are optionally substituted by one or more halogen.

6. The compound according to claim 1, wherein $R^2$ is Alkyl or haloalkyl.

7. The compound according to claim 1, wherein $R^3$ is phenyl substituted with 1 substituent which is halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

8. The compound according to claim 1, wherein $R^3$ is dihalophenyl.

9. The compound according to claim 1, wherein $R^3$ is trihalophenyl.

10. The compound according to claim 1, wherein q is 1.

11. The compound according to claim 1 wherein q is 0.

12. The compound according to claim 1, wherein X is $CH_2$.

13. The compound according to claim 1, wherein Y is $CH_2$.

14. The compound according to claim 1, wherein X is O.

15. A composition comprising the compound of claim 1 and a veterinarily acceptable carrier.

16. A compound of formula (IA):

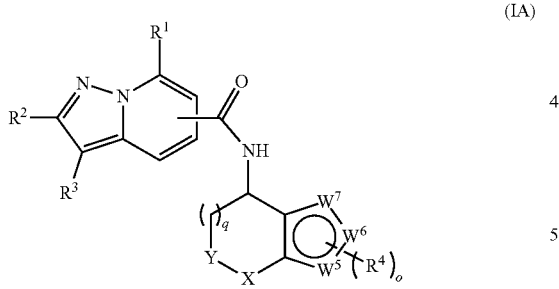

(IA)

wherein:

$W^5$, $W^6$ and $W^7$ are independently CH, N or S;

$R^1$ is -cyano, optionally substituted alkoxy, optionally substituted haloalkoxy, optionally substituted aryloxy, optionally substituted alkyl, optionally substituted haloalkyl, optionally substituted $C_3$-$C_8$-cycloalkyl, optionally substituted alkenyl, optionally substituted haloalkenyl, optionally substituted alkynyl, optionally substituted haloalkynyl, optionally substituted aryl; optionally substituted alkylcarbonyl, optionally substituted alkoxycarbonyl, optionally substituted aminocarbonyl, optionally substituted alkylaminocarbonyl, optionally substituted dialkylaminocarbonyl, optionally substituted alkyl-$SO_n$, haloalkyl-$SO_n$, amino, NH-optionally substituted alkyl, or $NR^aR^b$ wherein $R^a$ and $R^b$ are independently optionally substituted $C_1$-$C_4$ alkyl; or $R^a$ and $R^b$ may form, with the nitrogen to which they are attached, a 3, 4, 5, 6, 7, or 8 membered-heterocyclyl group, which may be optionally substituted;

$R^2$ is halogen, cyano, optionally substituted alkoxy, optionally substituted aryloxy, optionally substituted alkyl, optionally substituted $C_3$-$C_8$-cycloalkyl, or $SO_m$ (optionally substituted alkyl);

$R^3$ is selected from the group consisting of 6- or 10-membered aryl and 5- to 10-membered heteroaryl, each of which may be optionally substituted with 1, 2, 3, 4 or 5 substituents;

each $R^4$ is independently hydrogen, halogen, cyano, nitro, —OH, optionally substituted alkyl, optionally substituted alkoxy, optionally substituted cycloalkyl, -amino, NH-optionally substituted alkyl, $SF_5$, or $NR^cR^d$ wherein $R^c$ and $R^d$ are independently optionally substituted alkyl; or $R^c$ and $R^d$ may form, with the nitrogen to which they are attached, a 3, 4, 5, 6, 7, or 8 membered-heterocyclyl group, which may be optionally substituted, $SO_p$(optionally substituted $C_1$-$C_4$-alkyl);

o is 0, 1, 2, 3, or 4;

m, n, and p are independently 0, 1, or 2;

q is 0 or 1;

X and Y are independently $CR^5R^6$, O, S, or N—$R^7$, wherein at least one of X and Y is $CR^5R^6$;

$R^5$ and $R^6$ are independently hydrogen, fluorine or $C_1$-$C_4$-alkyl;

$R^7$ is hydrogen or $C_1$-$C_4$-alkyl; or a stereoisomer, tautomer, N-oxide, hydrate, solvate, or salt thereof.

17. A compound selected from the group consisting of:

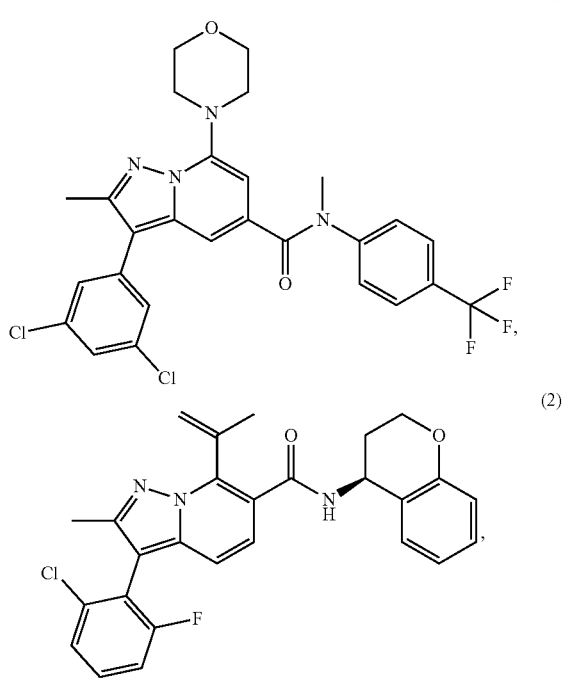

-continued
(3)
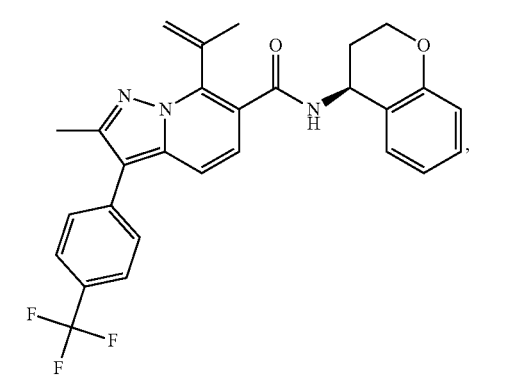
(4)
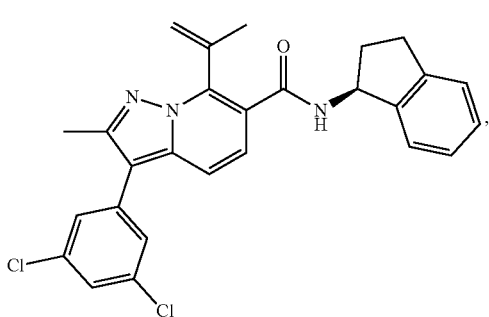
(5)
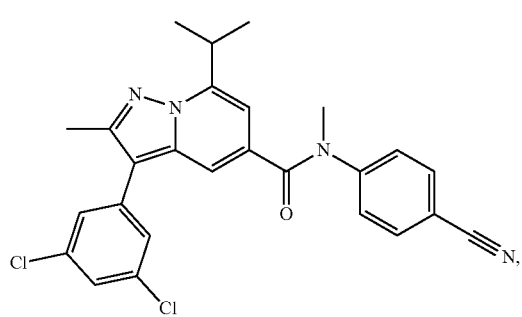
(6)
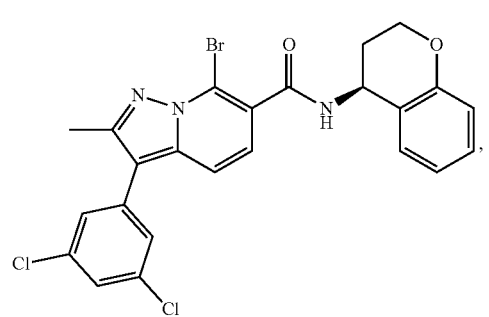
(7)
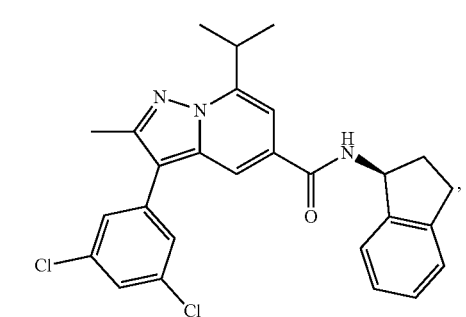
-continued
(8)
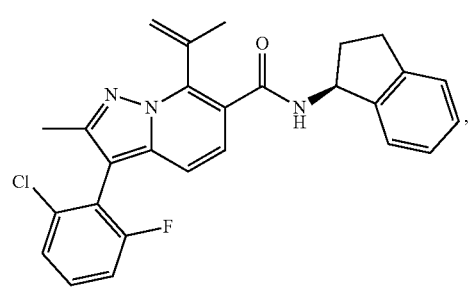
(9)
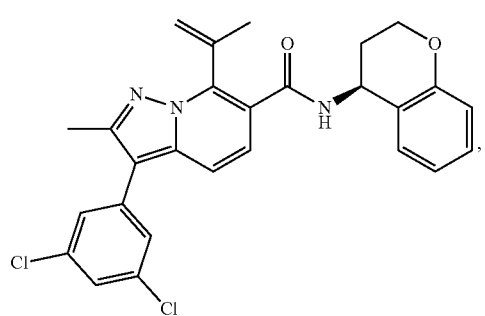
(10)
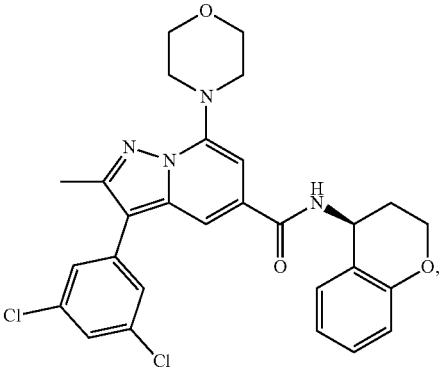
(11)
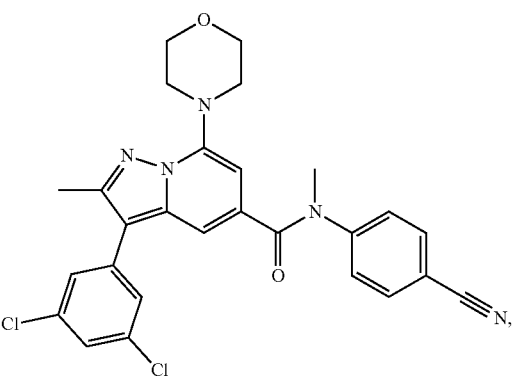

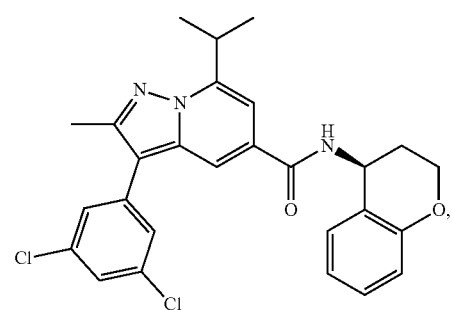
(12)
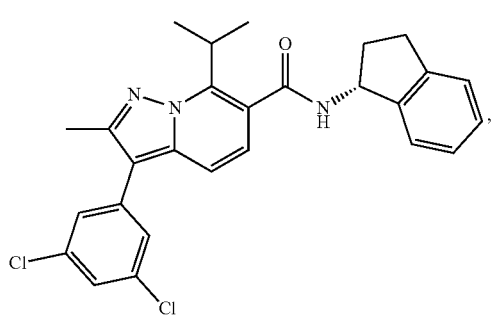
(13)
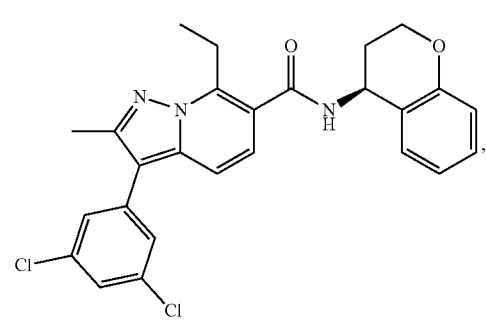
(14)
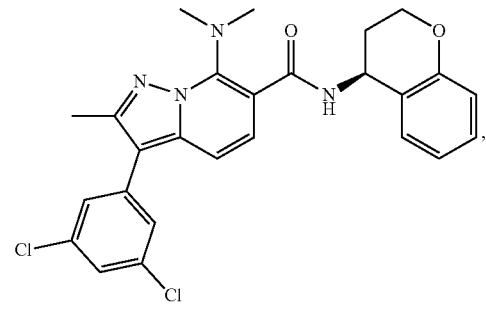
(15)
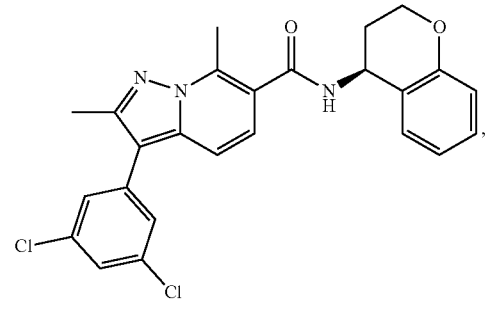
(16)
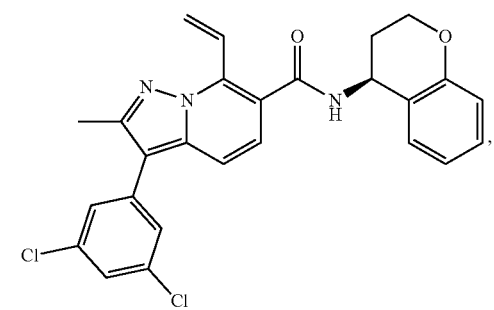
(17)
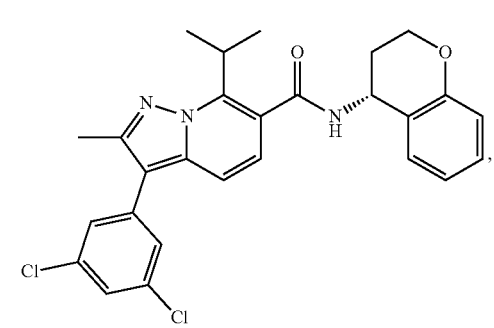
(18)
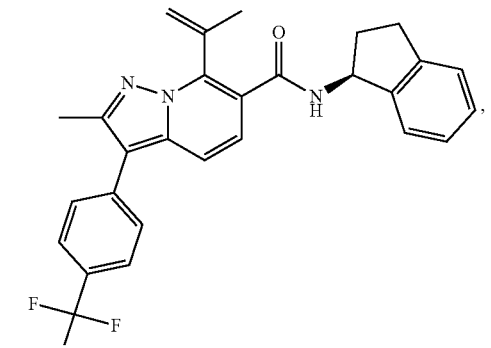
(19)
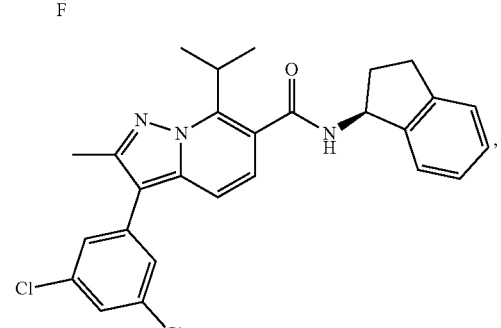
(20)
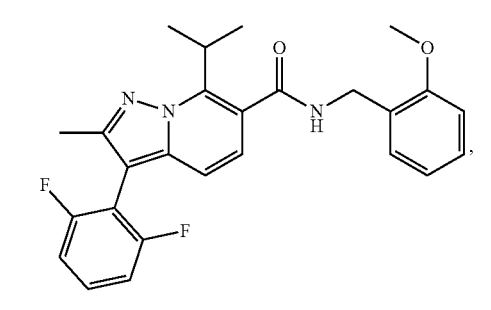
(21)

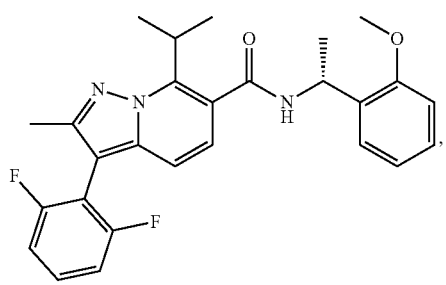
(22)
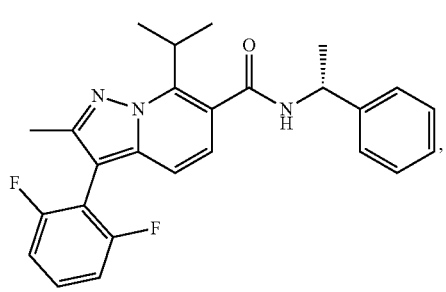
(23)
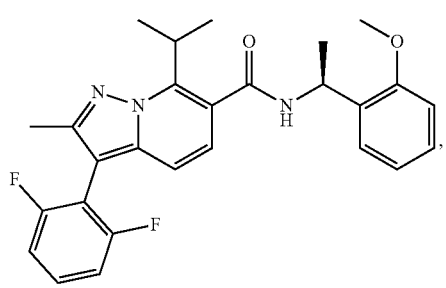
(24)
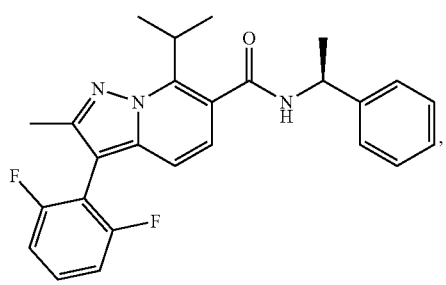
(25)
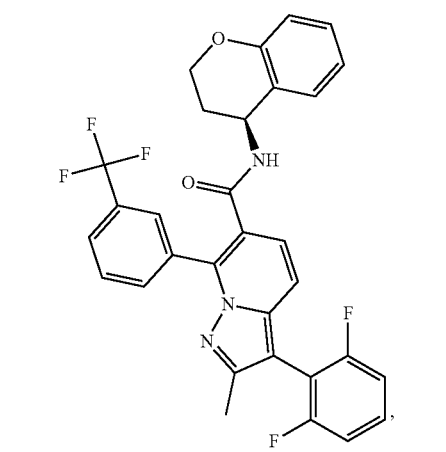
(26)
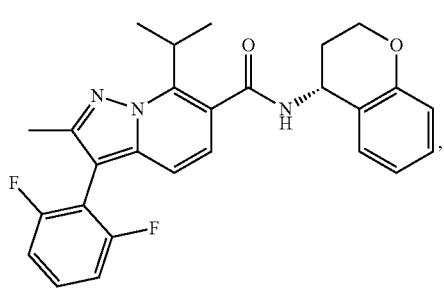
(27)
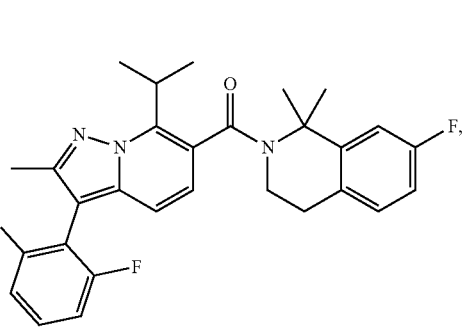
(28)
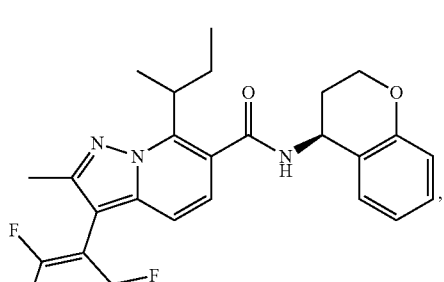
(29)
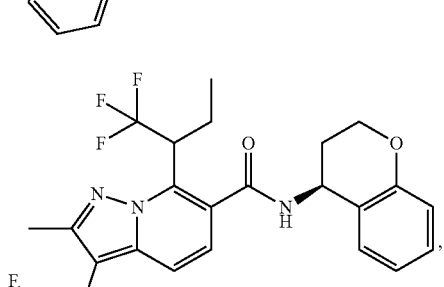
(30)
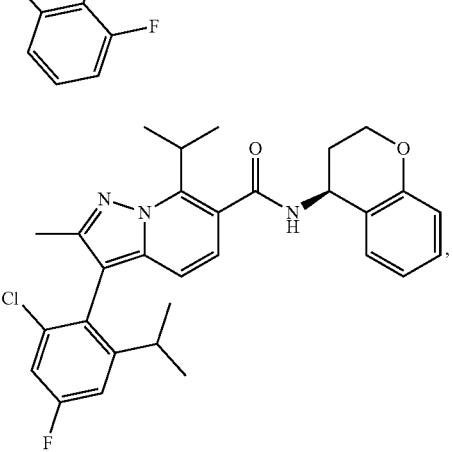
(31)

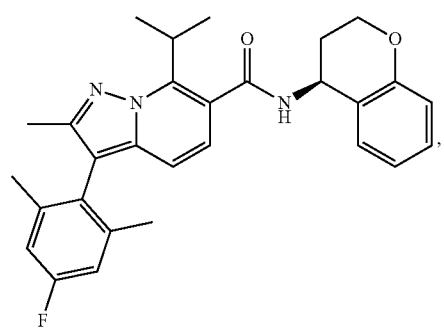
(32)
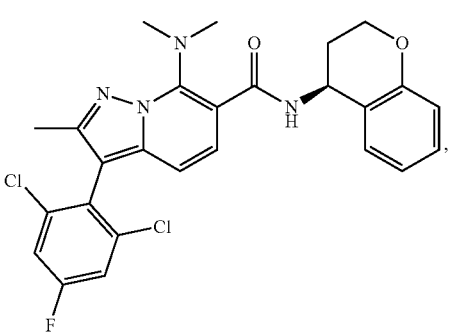
(33)
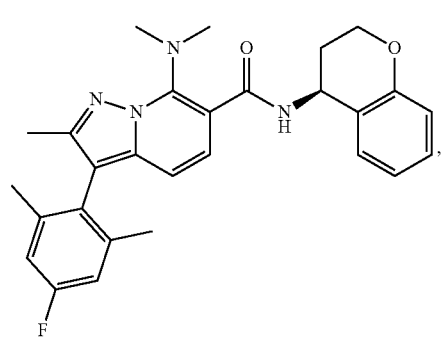
(34)
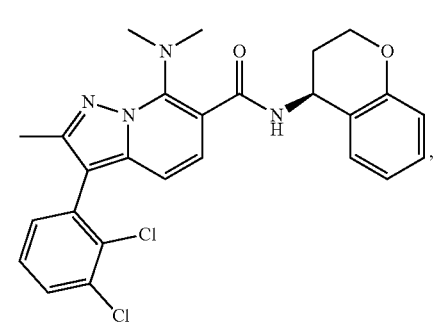
(35)
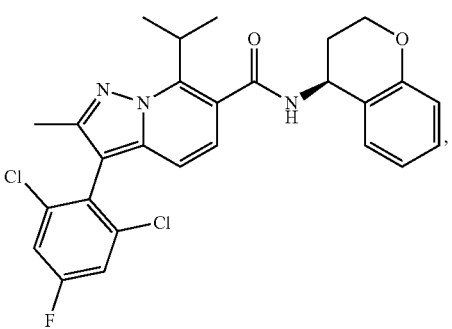
(36)
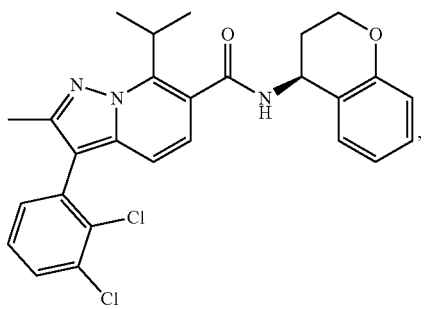
(37)
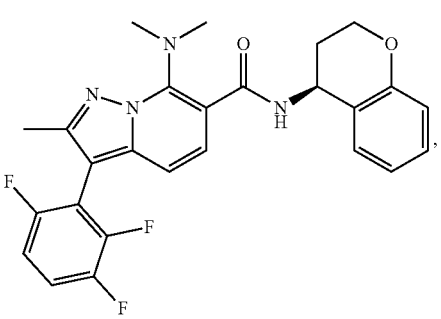
(38)
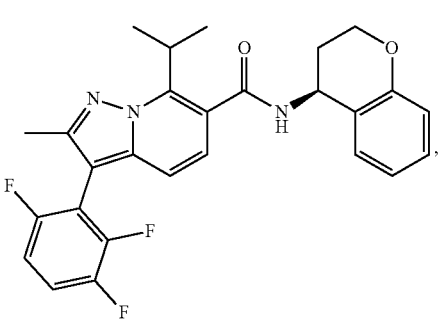
(39)
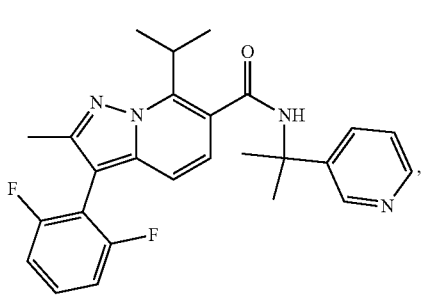
(40)
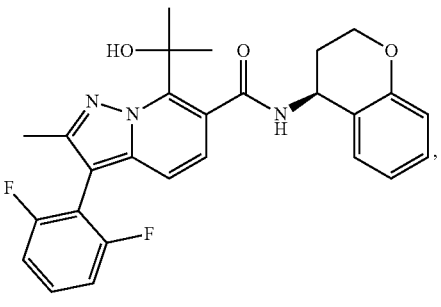
(41)

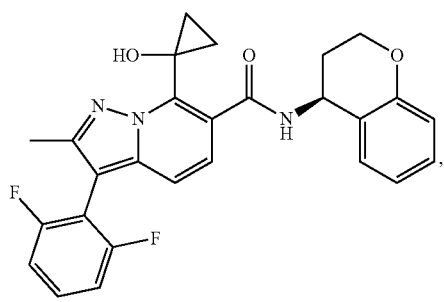
(42)
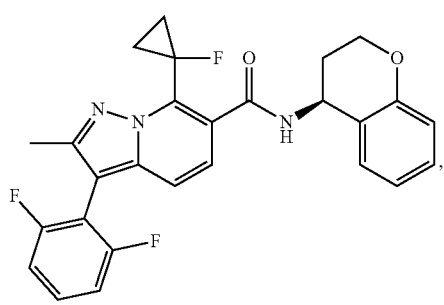
(43)
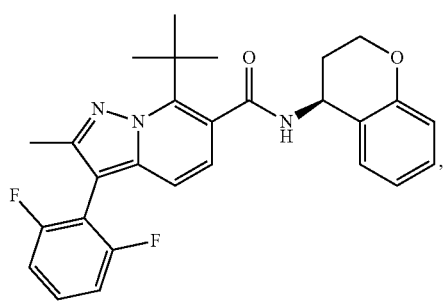
(44)
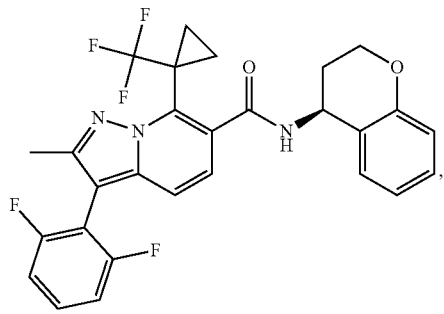
(45)
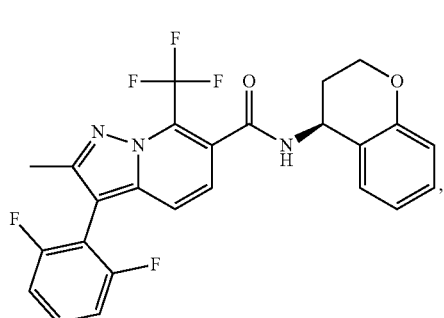
(46)
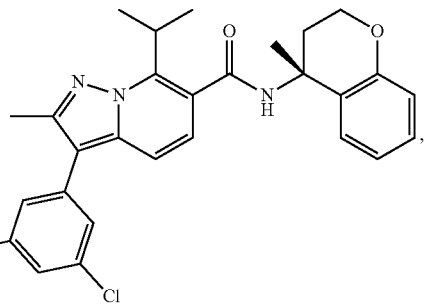
(47)
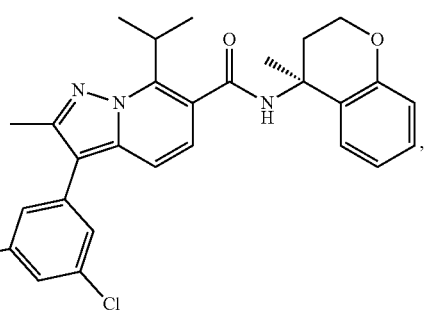
(48)
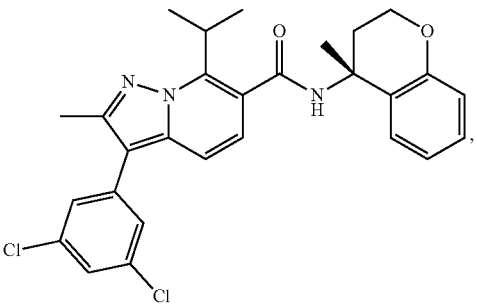
(49)
(50)
(51)

-continued
(52)
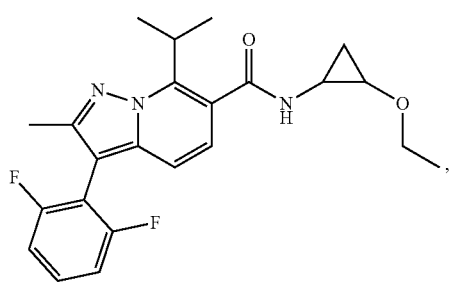
(53)
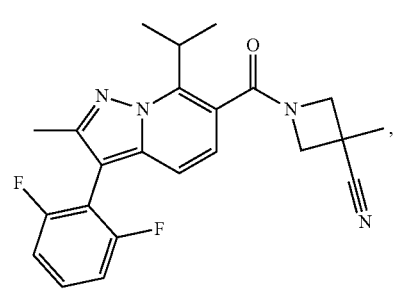
(54)
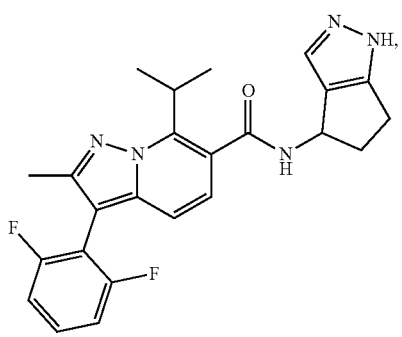
(55)
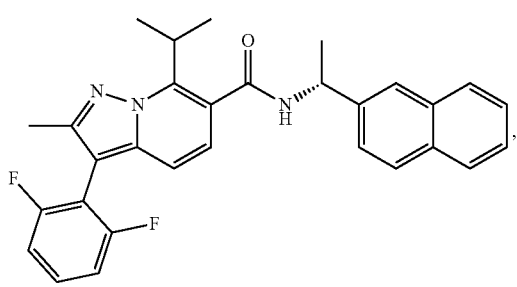
-continued
(56)
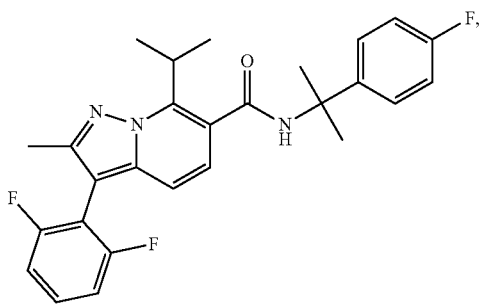
(57)
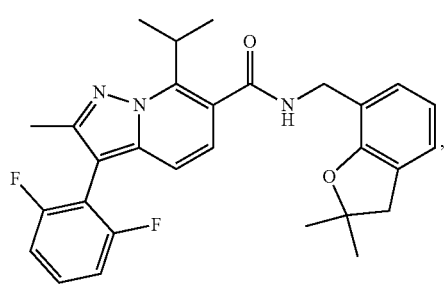
(58)
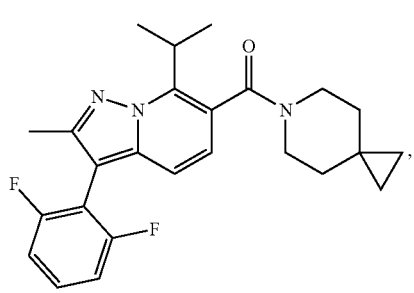
(59)
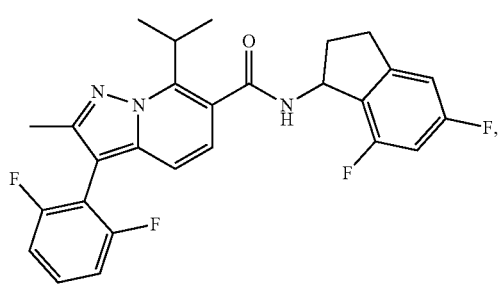

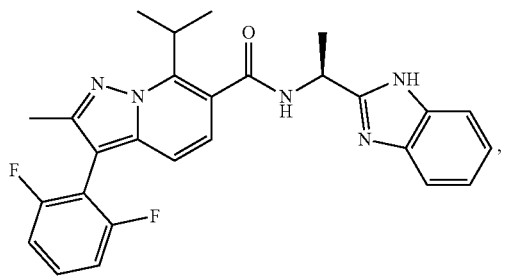
(60)
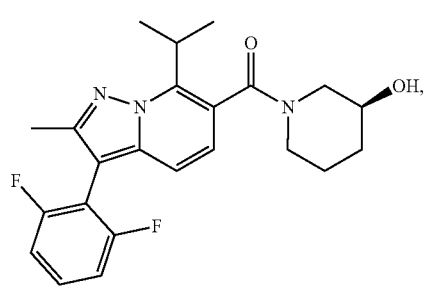
(61)
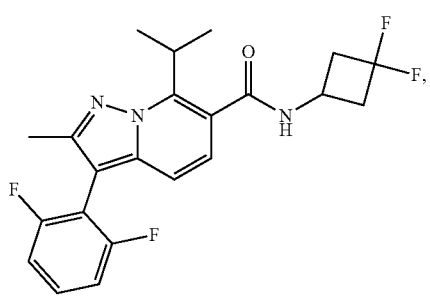
(62)
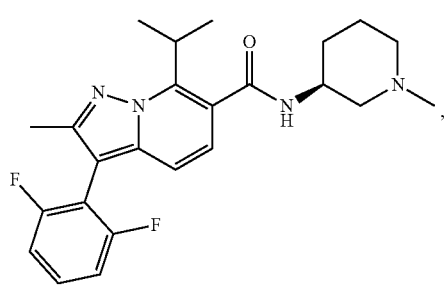
(63)
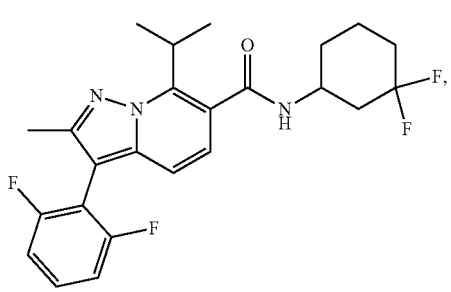
(64)
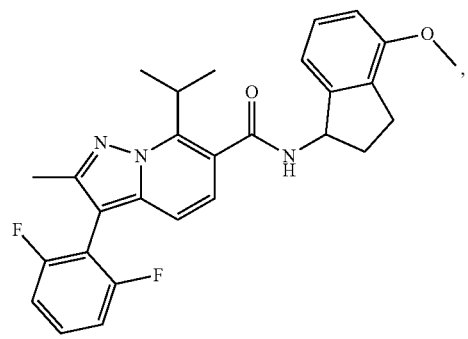
(65)
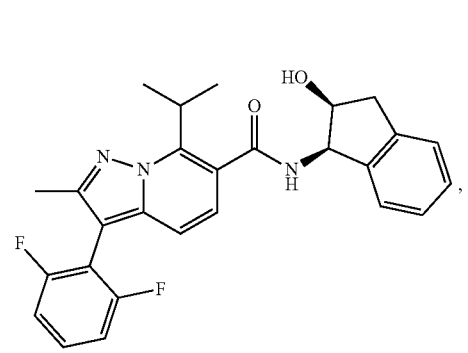
(66)
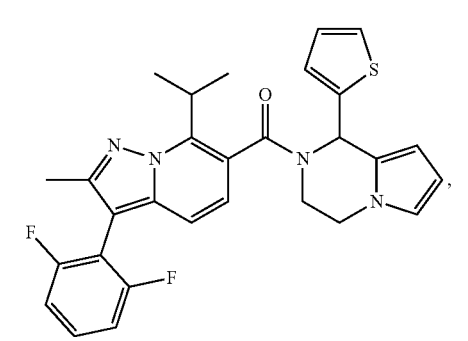
(67)
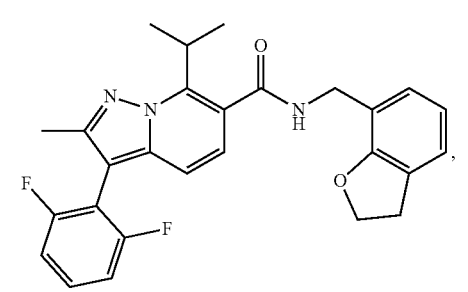
(68)
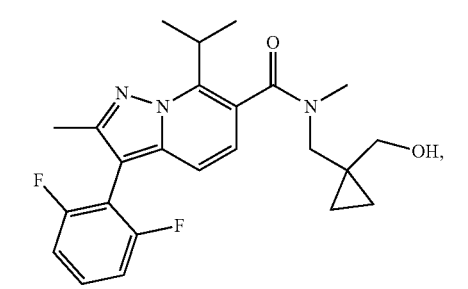
(69)

-continued
(70)
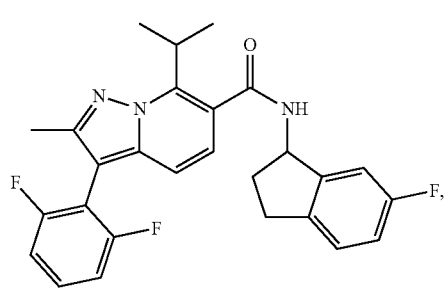
(71)
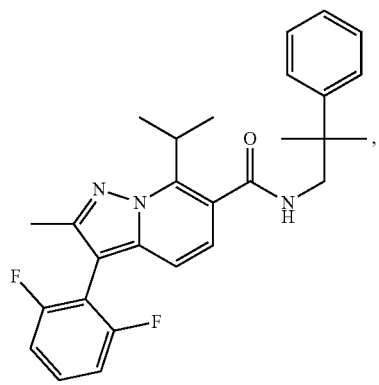
(72)
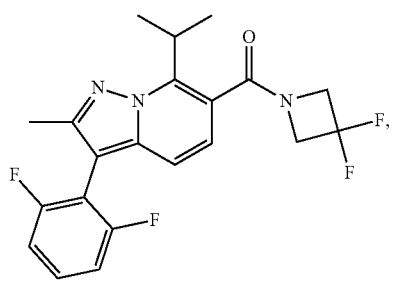
(73)
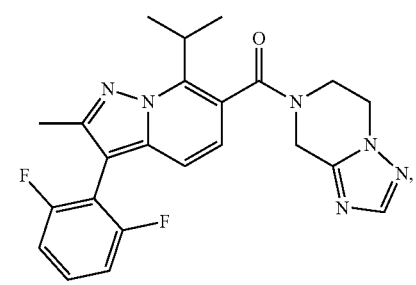
(74)
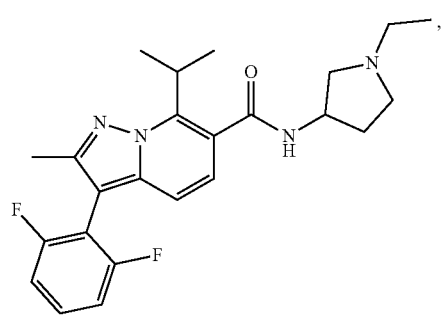
-continued
(75)
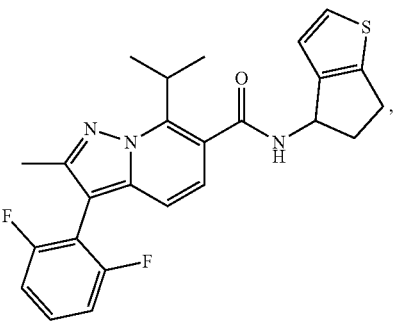
(76)
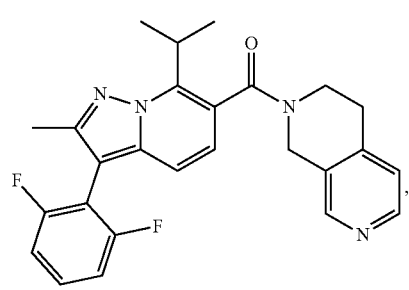
(77)
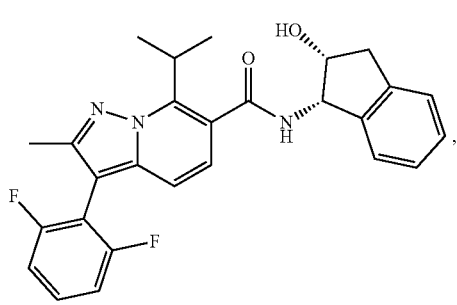
(78)
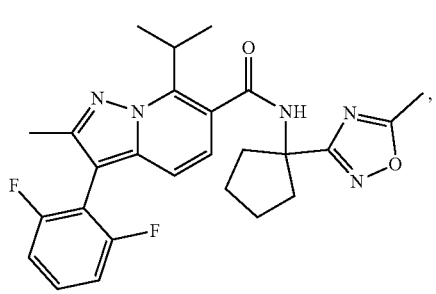
(79)
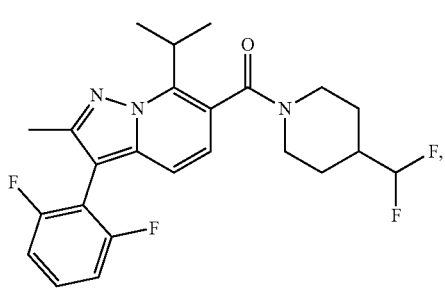

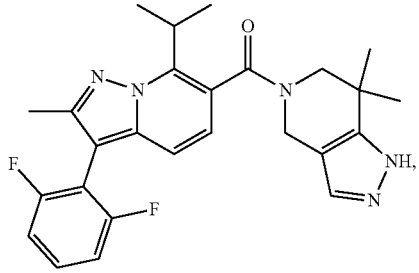
(80)
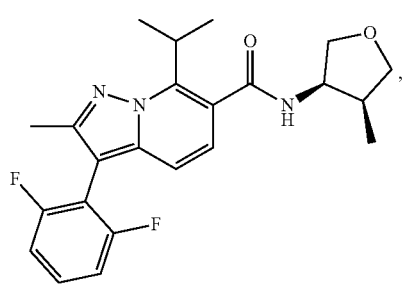
(81)
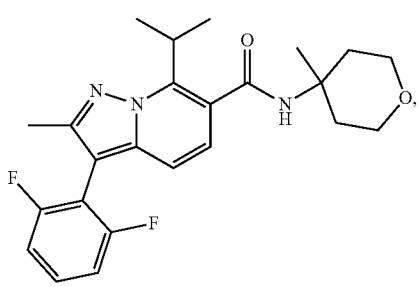
(82)
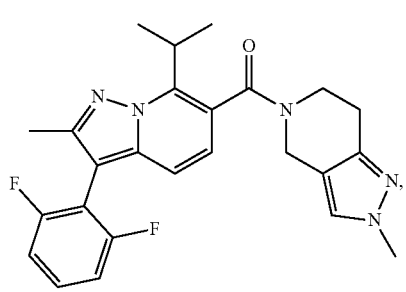
(83)
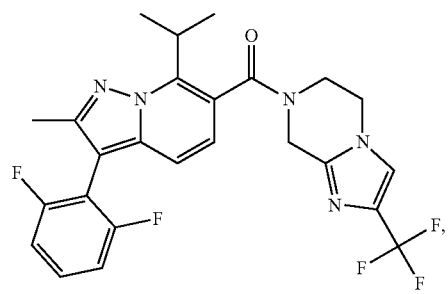
(84)
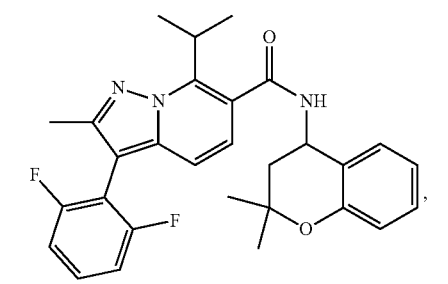
(85)
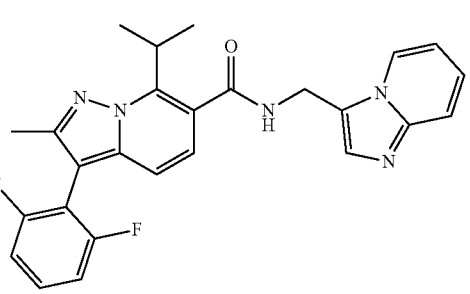
(86)
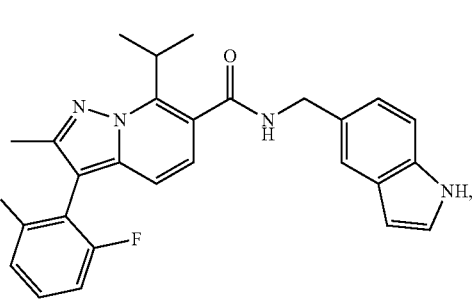
(87)
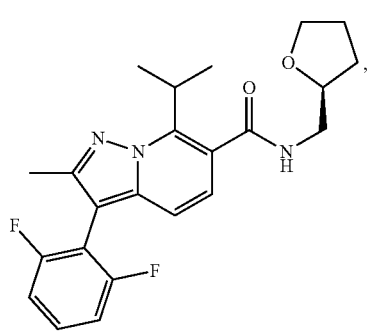
(88)

-continued
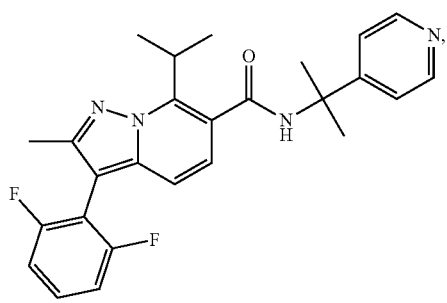
(89)
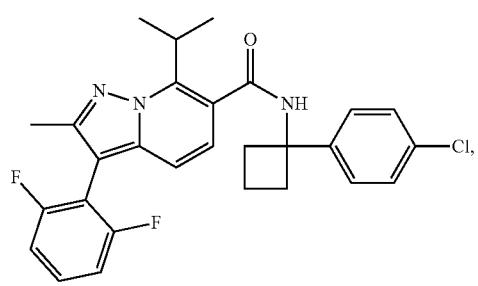
(90)
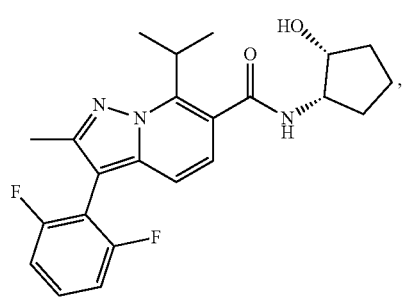
(91)
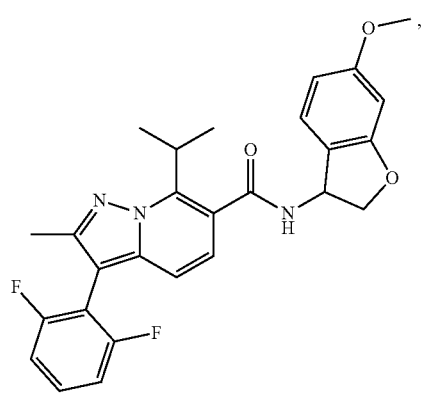
(92)
-continued
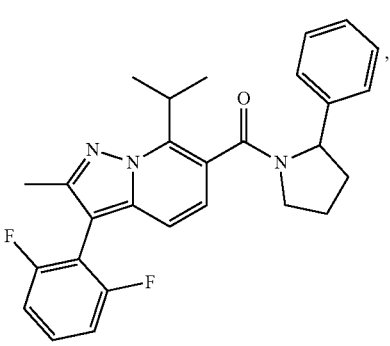
(93)
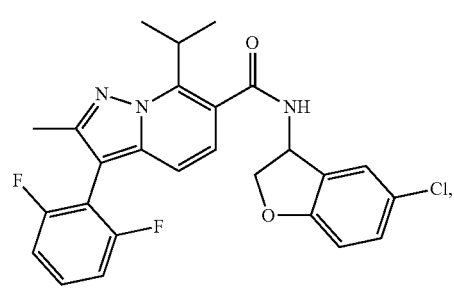
(94)
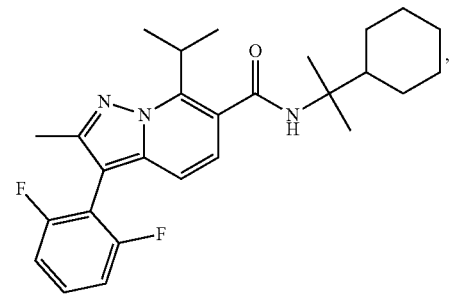
(95)
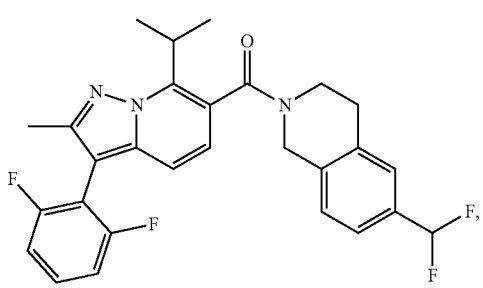
(96)
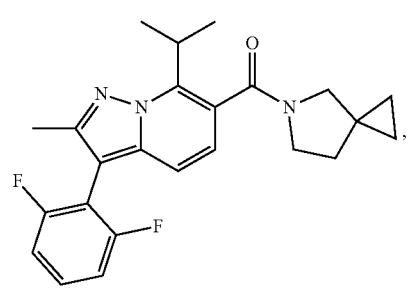
(97)

-continued
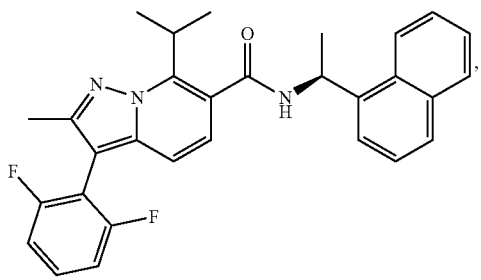(98)
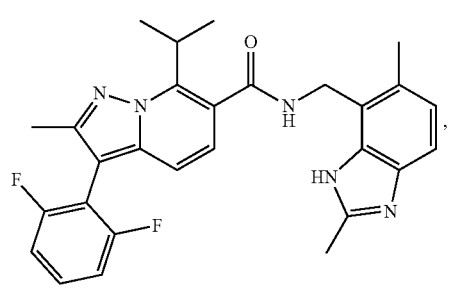(99)
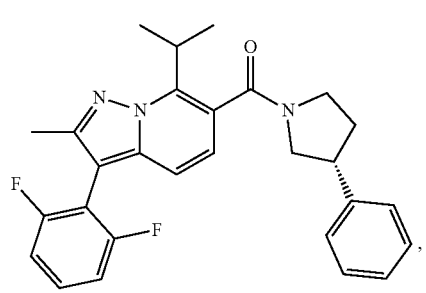(100)
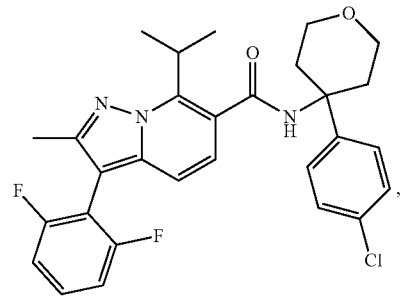(101)
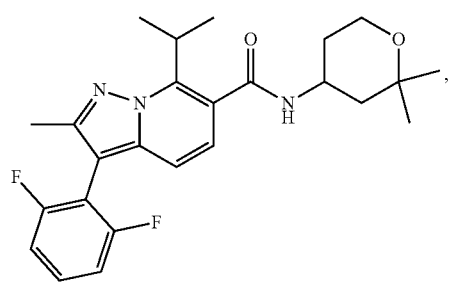(102)
-continued
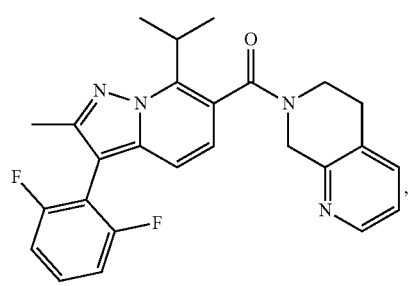(103)
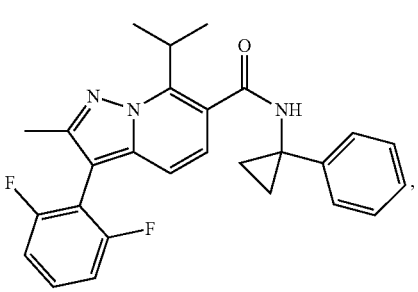(104)
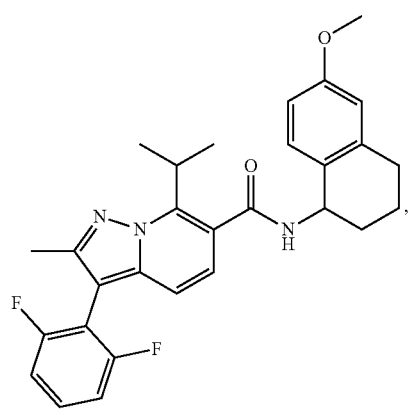(105)
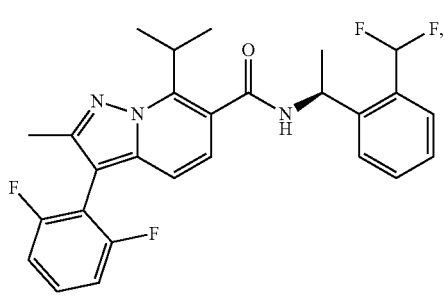(106)
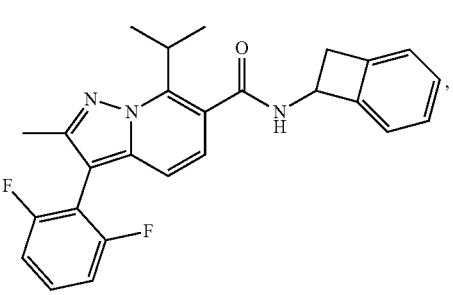(107)

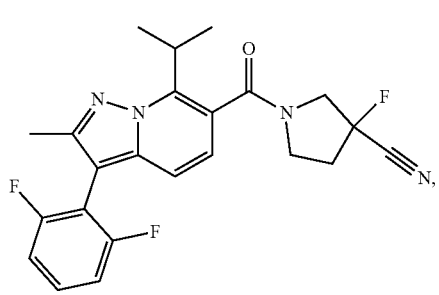
(108)
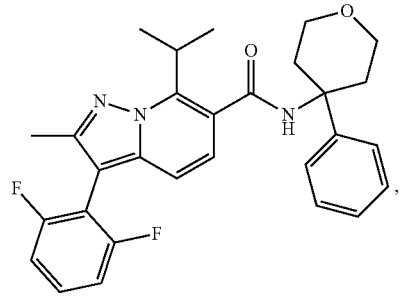
(112)
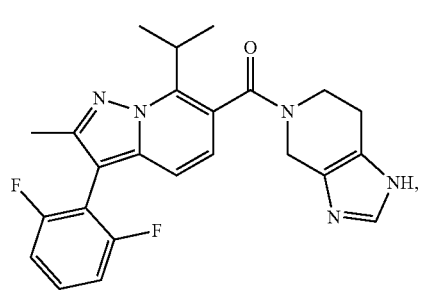
(109)
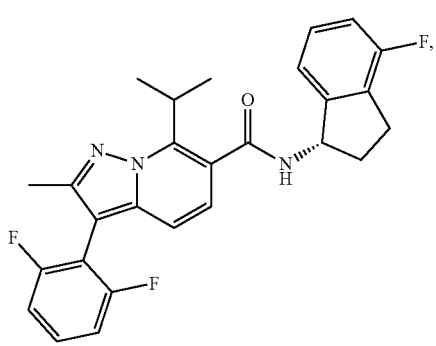
(113)
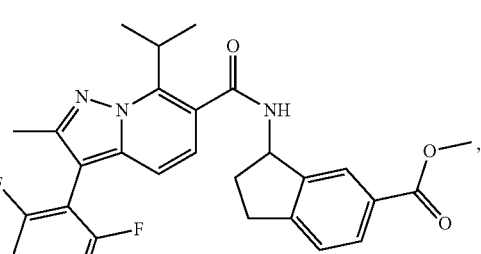
(114)
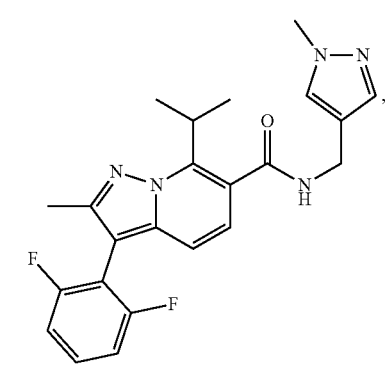
(110)
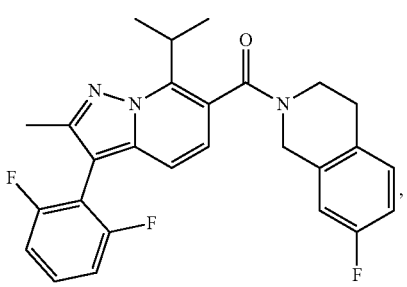
(115)
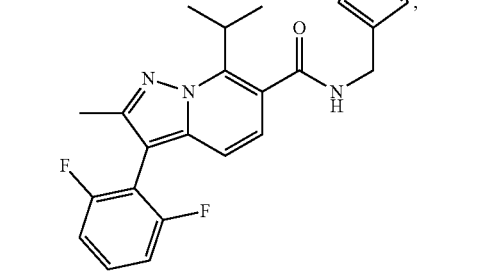
(111)
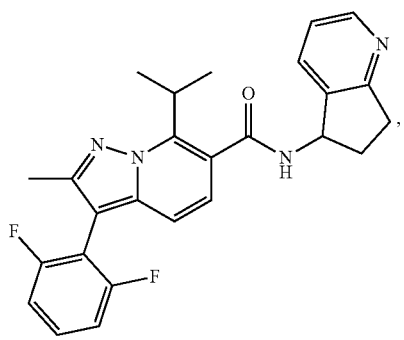
(116)
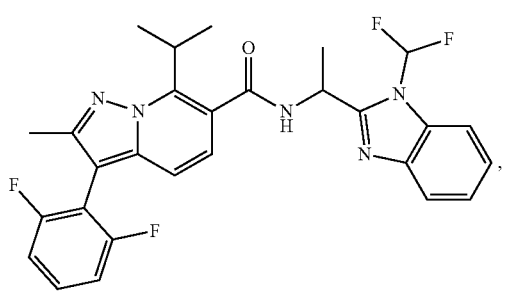

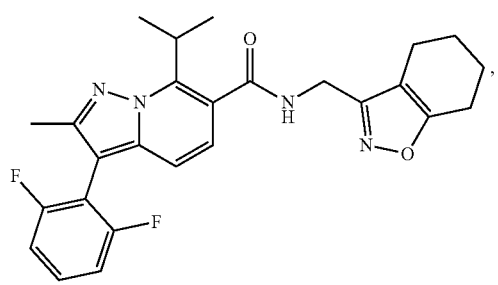
(117)
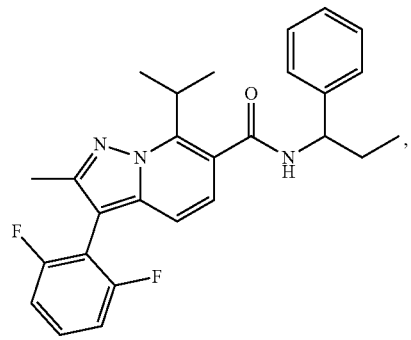
(118)
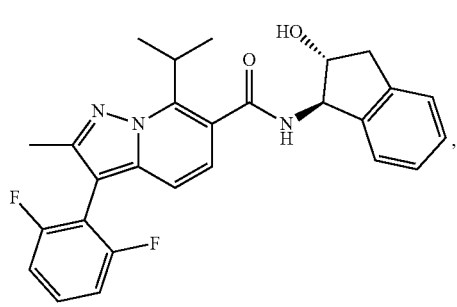
(119)
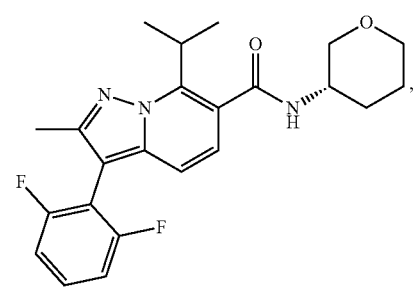
(120)
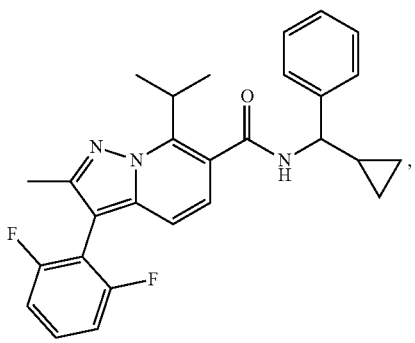
(121)
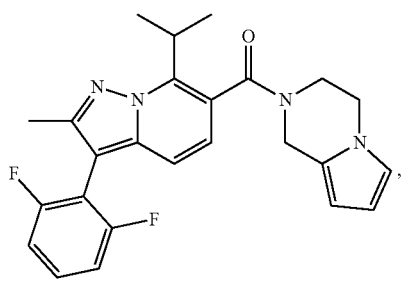
(122)
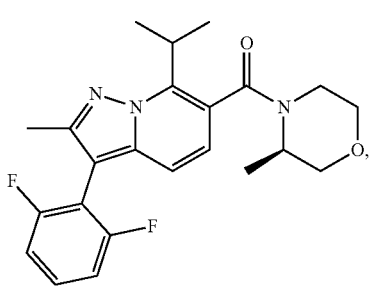
(123)
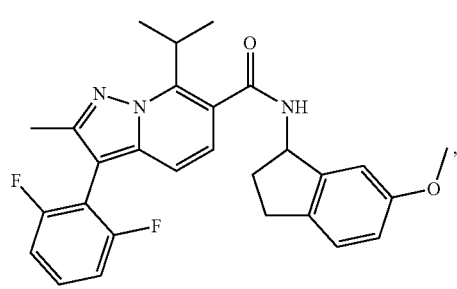
(124)
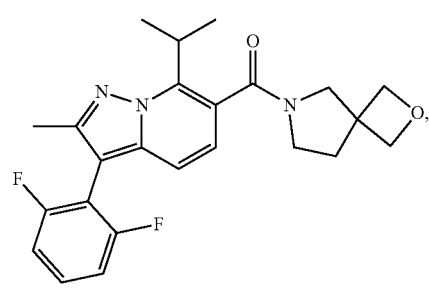
(125)
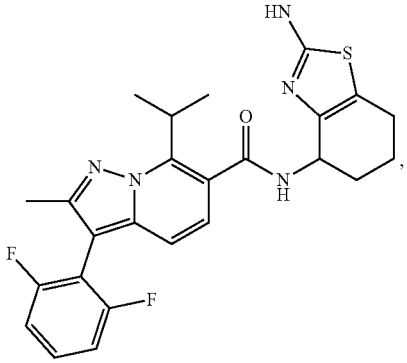
(126)

-continued
(127) 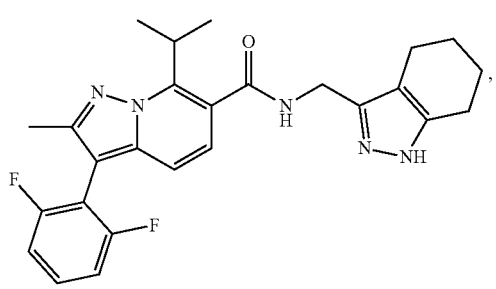
(128) 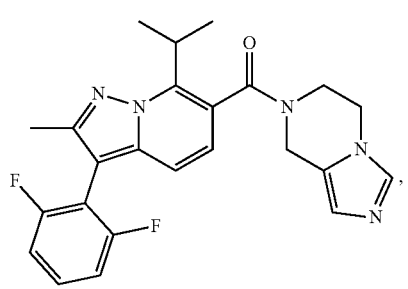
(129) 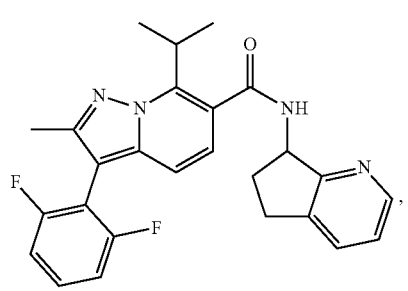
(130)
(131)
-continued
(132) 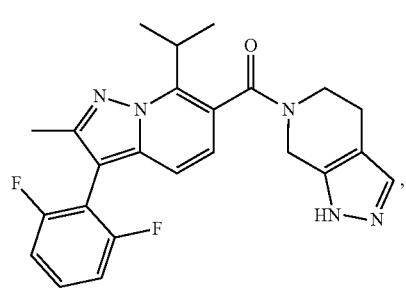
(133) 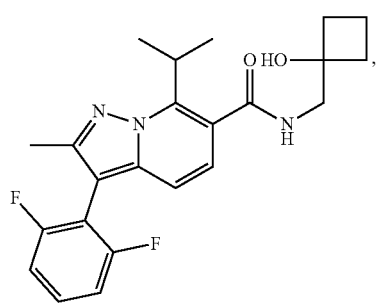
(134) 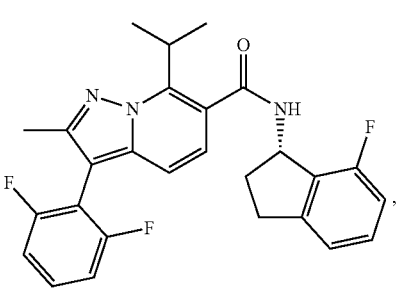
(135) 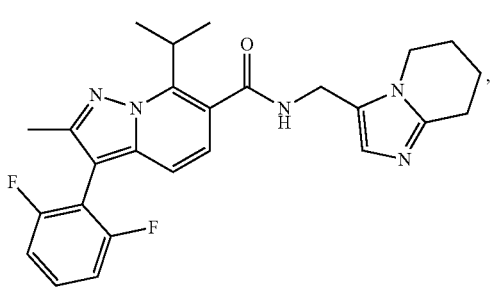
(136) 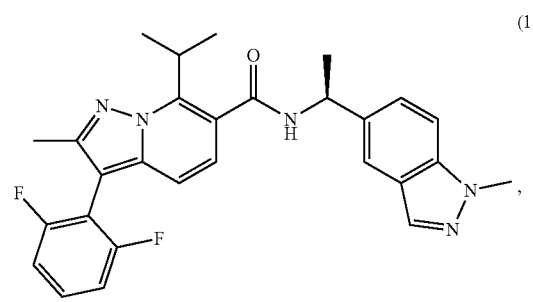

-continued
(137)
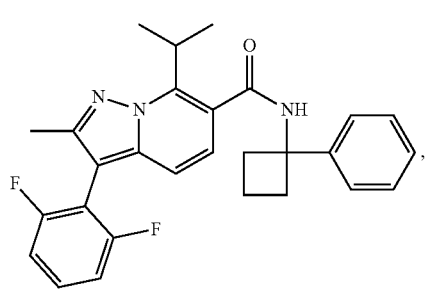
(138)
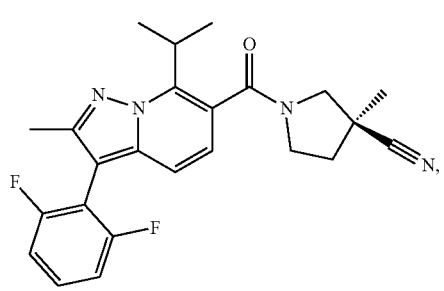
(139)
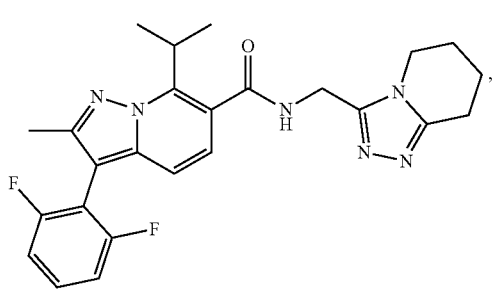
(140)
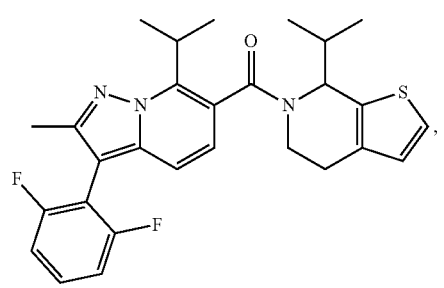
(141)
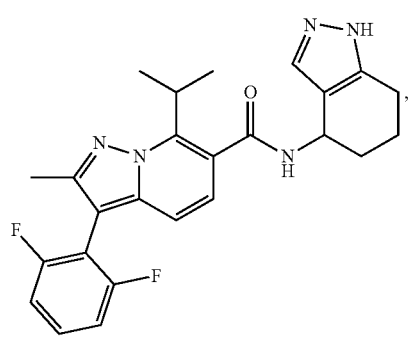
-continued
(142)
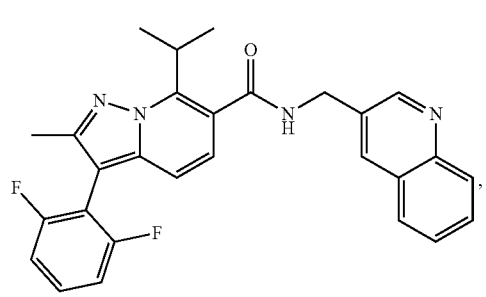
(143)
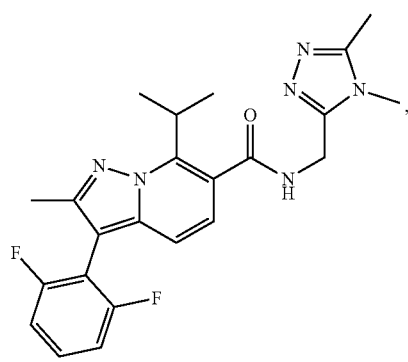
(144)
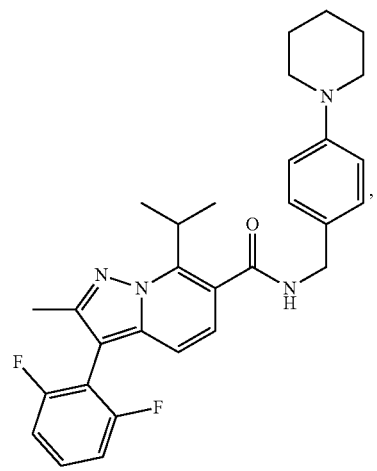
(145)
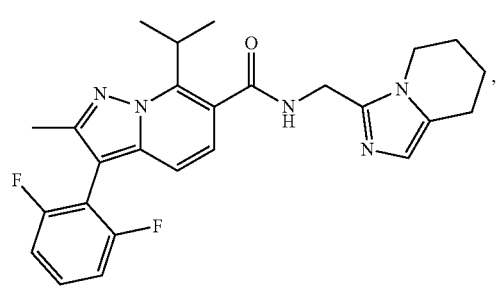

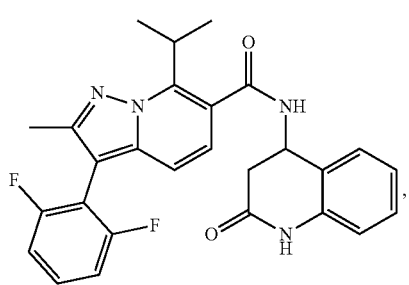 (146)
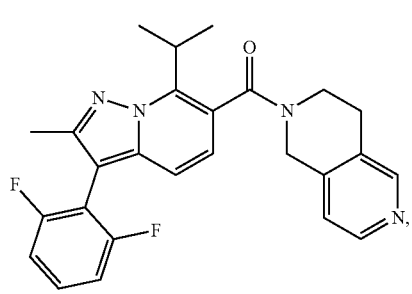 (151)
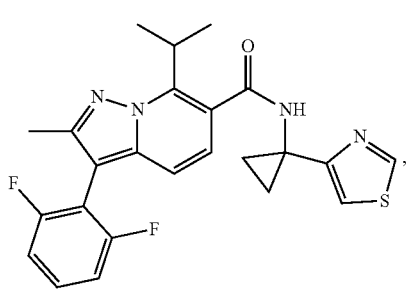 (147)
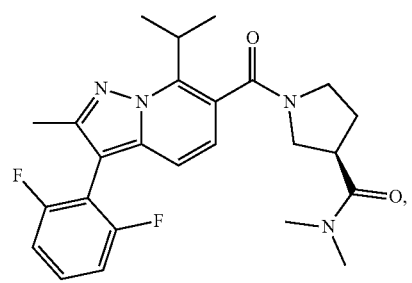 (152)
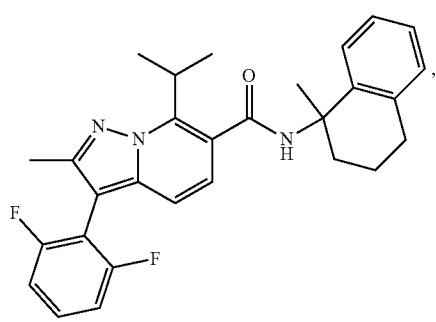 (148)
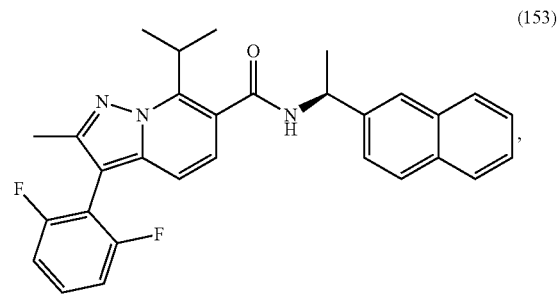 (153)
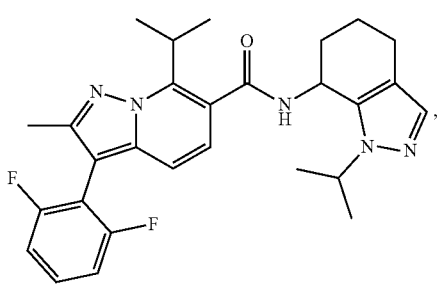 (149)
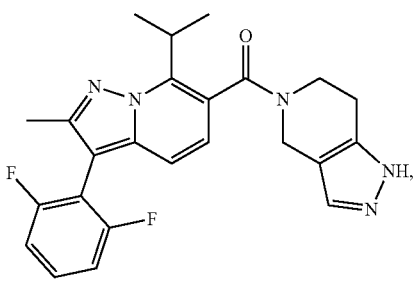 (154)
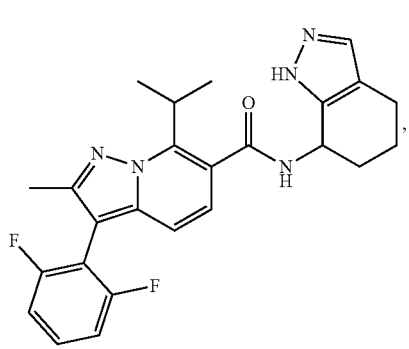 (150)
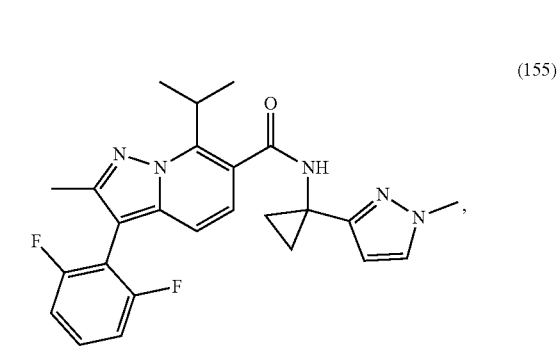 (155)

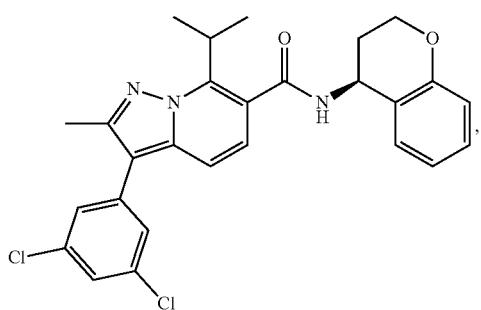
(156)
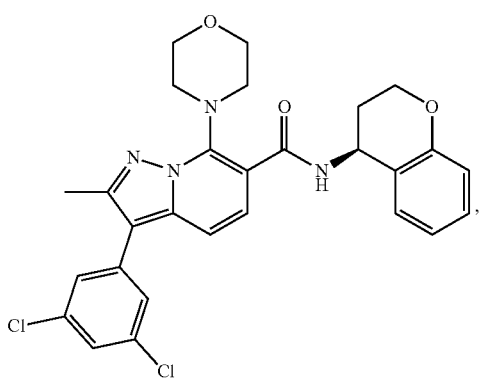
(157)
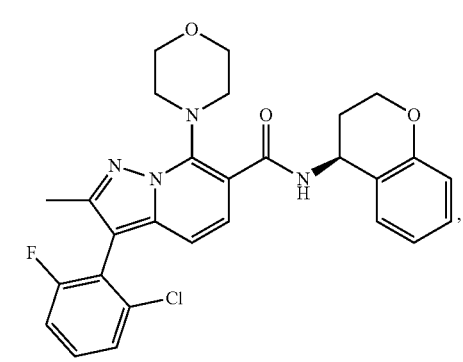
(158)
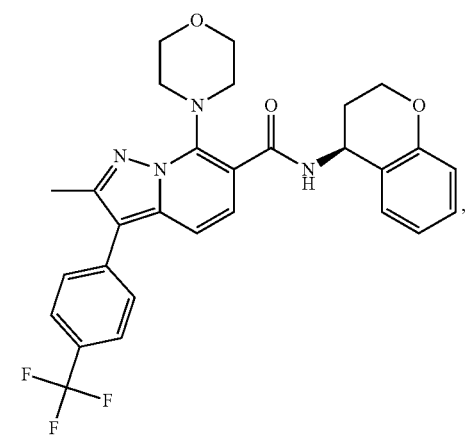
(159)
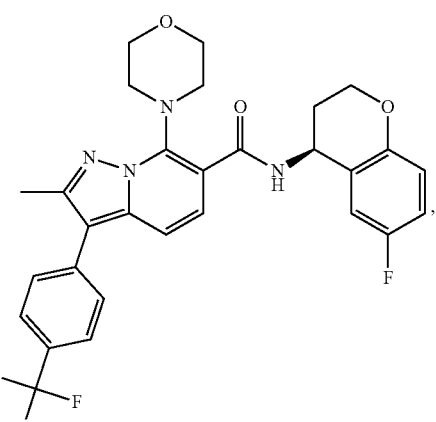
(160)
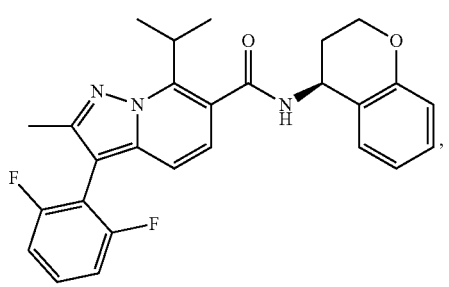
(161)
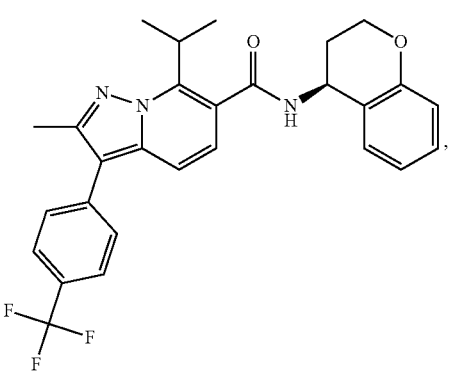
(162)
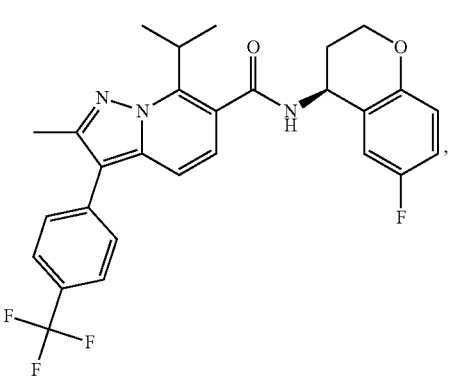
(163)

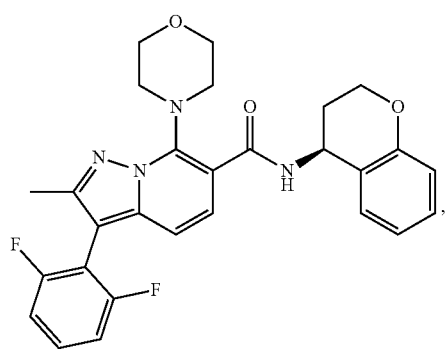
(164)
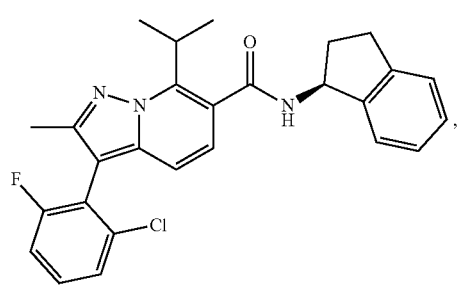
(169)
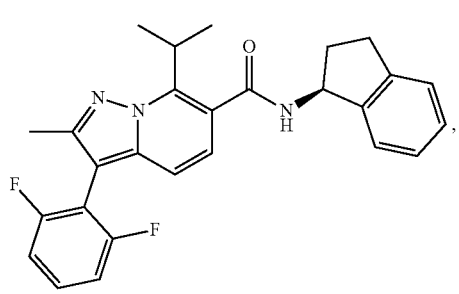
(165)
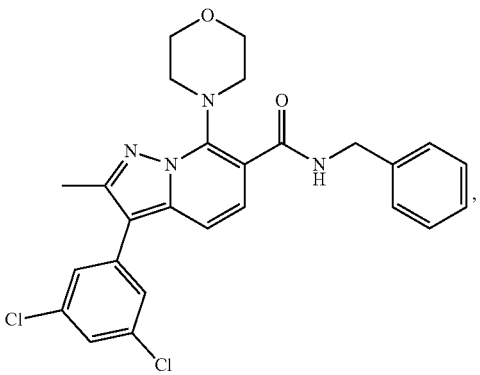
(170)
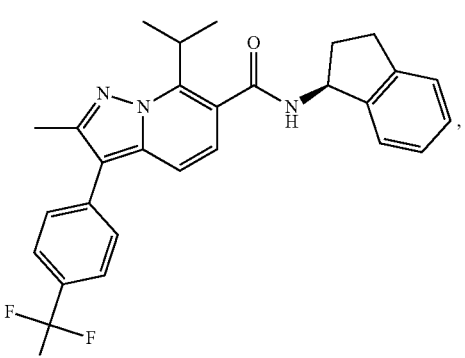
(166)
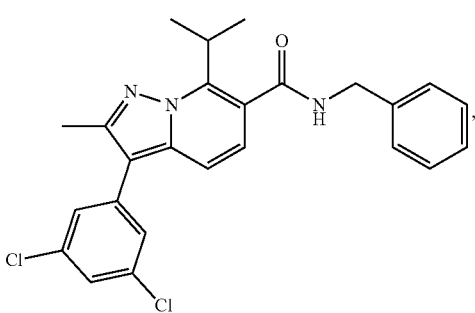
(171)
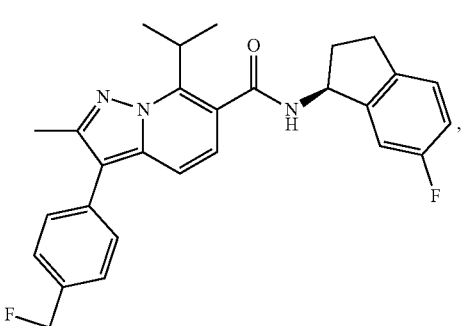
(167)
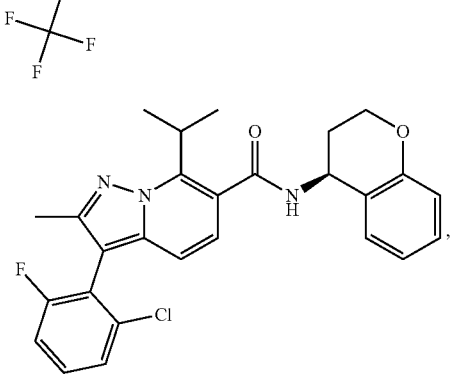
(168)
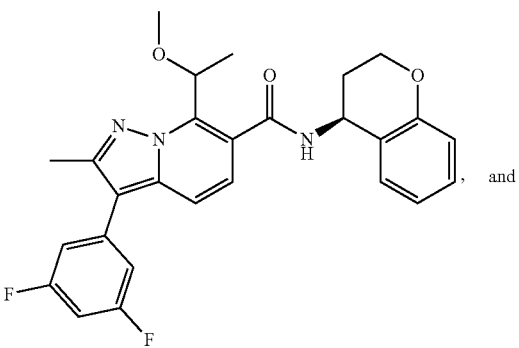
(172)
, and (173)
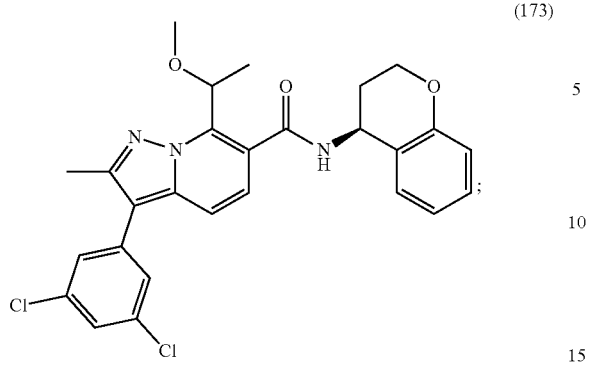
or a pharmaceutically acceptable salt thereof.
* * * * *